US009639657B2

(12) United States Patent
Rabinowitz et al.

(10) Patent No.: US 9,639,657 B2
(45) Date of Patent: May 2, 2017

(54) METHODS FOR ALLELE CALLING AND PLOIDY CALLING

(71) Applicant: Natera, Inc., San Carlos, CA (US)

(72) Inventors: Matthew Rabinowitz, San Francisco, CA (US); George Gemelos, New York, NY (US); Milena Banjevic, Los Altos Hills, CA (US); Allison Ryan, Redwood City, CA (US); Joshua Sweetkind-Singer, San Jose, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

(21) Appl. No.: 13/846,111

(22) Filed: Mar. 18, 2013

(65) Prior Publication Data
US 2013/0225422 A1    Aug. 29, 2013

Related U.S. Application Data

(63) Continuation of application No. 13/057,350, filed as application No. PCT/US2009/052730 on Aug. 4, 2009, now abandoned.

(60) Provisional application No. 61/137,851, filed on Aug. 4, 2008, provisional application No. 61/188,343, filed on Aug. 8, 2008, provisional application No. 61/194,854, filed on Oct. 1, 2008, provisional application No. 61/198,690, filed on Nov. 7, 2008.

(51) Int. Cl.
G01N 33/50 (2006.01)
G06F 19/18 (2011.01)
C12Q 1/68 (2006.01)
G06F 19/24 (2011.01)

(52) U.S. Cl.
CPC ........... *G06F 19/18* (2013.01); *C12Q 1/6883* (2013.01); *C12Q 2600/156* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 5,635,366 A | 6/1997 | Cook | |
| 5,716,776 A | 2/1998 | Bogart | |
| 5,753,467 A | 5/1998 | Jensen et al. | |
| 5,824,467 A | 10/1998 | Mascarenhas | |
| 5,860,917 A | 1/1999 | Comanor | |
| 5,972,602 A | 10/1999 | Hyland et al. | |
| 5,994,148 A | 11/1999 | Stewart | |
| 6,001,611 A | 12/1999 | Will | |
| 6,025,128 A | 2/2000 | Veltri | |
| 6,108,635 A | 8/2000 | Herren | |
| 6,143,496 A | 11/2000 | Brown et al. | |
| 6,180,349 B1 | 1/2001 | Ginzinger et al. | |
| 6,214,558 B1 | 4/2001 | Shuber et al. | |
| 6,258,540 B1 | 7/2001 | Lo et al. | |
| 6,300,077 B1 | 10/2001 | Shuber et al. | |
| 6,440,706 B1 | 8/2002 | Vogelstein et al. | |
| 6,479,235 B1 | 11/2002 | Schumm et al. | |
| 6,489,135 B1 | 12/2002 | Parrott | |
| 6,720,140 B1 | 4/2004 | Hartley | |
| 6,807,491 B2 | 10/2004 | Pavlovic et al. | |
| 6,852,487 B1 | 2/2005 | Barany et al. | |
| 6,958,211 B2 | 10/2005 | Vingerhoets | |
| 7,035,739 B2 | 4/2006 | Schadt | |
| 7,058,517 B1 | 6/2006 | Denton | |
| 7,058,616 B1 | 6/2006 | Larder | |
| 7,218,764 B2 | 5/2007 | Vaisberg | |
| 7,297,485 B2 | 11/2007 | Bornarth | |
| 7,332,277 B2 | 2/2008 | Dhallan | |
| 7,414,118 B1 | 8/2008 | Mullah et al. | |
| 7,442,506 B2 | 10/2008 | Dhallan | |
| 7,459,273 B2 | 12/2008 | Jones et al. | |
| 7,645,576 B2 | 1/2010 | Lo et al. | |

(Continued)

FOREIGN PATENT DOCUMENTS

EP   1 524 321      4/2005
EP   1524321 B1    7/2009
(Continued)

OTHER PUBLICATIONS

Zhao et al., An Integrated View of Copy Number and Allelic Alterations in the Cancer Genome Using Single Nulceotide Polymorphism Arrays, May 2004, Cancer Research, 64, pp. 3060-3071.*
Abidi et al., Leveraging XML-based Electronic Medical Records to Extract Experimental Clinical Knowledge, International Journal of Medical Informatics, 68, pp. 187-203 (Dec. 18, 2002).
Allaire, Mate Selection by Selection Index Theory, Theor. Appl. Genet., 57, pp. 267-272 (Nov. 1980).
Ashoor et al., Chromosome-Selective Sequencing of Maternal Plasma Cell-Free DNA for First-Trimester Detection of Trisomy 21 and Trisomy 18, American Journal of Obstetrics & Gynecology (Jan. 27, 2012).
(Continued)

Primary Examiner — Jason Sims
(74) Attorney, Agent, or Firm — Anton Bokal

(57) ABSTRACT

Disclosed herein is a system and method for making allele calls, and for determining the ploidy state, in one or a small set of cells, or where a limited quantity of genetic data is available. Poorly or incorrectly measured base pairs, missing alleles and missing regions are reconstructed and the haplotypes are determined using expected similarities between the target genome and the knowledge of the genomes of genetically related individuals. In one embodiment, incomplete genetic data from an embryonic cell are reconstructed at a plurality of loci using the genetic data from both parents, and possibly one or more sperm and/or sibling embryos. In another embodiment, the chromosome copy number can be determined using the same input data. In another embodiment, these determinations are made for embryo selection during IVF, for non-invasive prenatal diagnosis, or for making phenotypic predictions.

17 Claims, 13 Drawing Sheets

(56) References Cited

U.S. PATENT DOCUMENTS

| | | | |
|---|---|---|---|
| 7,700,325 B2 | 4/2010 | Cantor et al. |
| 7,718,367 B2 | 5/2010 | Lo et al. |
| 7,718,370 B2 | 5/2010 | Dhallan |
| 7,727,720 B2 | 6/2010 | Dhallan |
| 7,805,282 B2 | 9/2010 | Casey |
| 7,838,647 B2 | 11/2010 | Hahn et al. |
| 7,888,017 B2 | 2/2011 | Quake et al. |
| 8,008,018 B2 | 8/2011 | Quake et al. |
| 8,024,128 B2 | 9/2011 | Rabinowitz et al. |
| 8,137,912 B2 | 3/2012 | Kapur et al. |
| 8,168,389 B2 | 5/2012 | Shoemaker et al. |
| 8,195,415 B2 | 6/2012 | Fan et al. |
| 8,296,076 B2 | 10/2012 | Fan et al. |
| 8,304,187 B2 | 11/2012 | Fernando |
| 8,318,430 B2 | 11/2012 | Chuu et al. |
| 8,467,976 B2 | 6/2013 | Lo et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 8,949,036 B2 | 2/2015 | Rabinowitz et al. |
| 9,163,282 B2 | 10/2015 | Rabinowitz et al. |
| 9,334,541 B2 | 5/2016 | Rabinowitz et al. |
| 9,424,392 B2 | 8/2016 | Rabinowitz et al. |
| 9,430,611 B2 | 8/2016 | Rabinowitz et al. |
| 2001/0053519 A1 | 12/2001 | Fodor et al. |
| 2002/0006622 A1 | 1/2002 | Bradley et al. |
| 2003/0009295 A1 | 1/2003 | Markowitz |
| 2003/0065535 A1 | 4/2003 | Karlov |
| 2003/0077586 A1 | 4/2003 | Pavlovic et al. |
| 2003/0101000 A1 | 5/2003 | Bader |
| 2003/0228613 A1 | 12/2003 | Bornarth |
| 2004/0033596 A1 | 2/2004 | Threadgill |
| 2004/0137470 A1 | 7/2004 | Dhallan |
| 2004/0197797 A1 | 10/2004 | Inoko et al. |
| 2004/0236518 A1 | 11/2004 | Pavlovic |
| 2004/0259100 A1 | 12/2004 | Gunderson |
| 2005/0009069 A1 | 1/2005 | Liu |
| 2005/0049793 A1 | 3/2005 | Paterlini-Brechot |
| 2005/0123914 A1 | 6/2005 | Katz et al. |
| 2005/0142577 A1 | 6/2005 | Jones et al. |
| 2005/0144664 A1 | 6/2005 | Smith |
| 2005/0164241 A1 | 7/2005 | Hahn et al. |
| 2005/0221341 A1 | 10/2005 | Shimkets et al. |
| 2005/0227263 A1 | 10/2005 | Green et al. |
| 2005/0250111 A1 | 11/2005 | Xie |
| 2005/0255508 A1 | 11/2005 | Casey et al. |
| 2005/0272073 A1 | 12/2005 | Vaisberg |
| 2006/0019278 A1 | 1/2006 | Lo et al. |
| 2006/0040300 A1 | 2/2006 | Dapprich et al. |
| 2006/0052945 A1 | 3/2006 | Rabinowitz |
| 2006/0057618 A1 | 3/2006 | Piper |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt |
| 2006/0141499 A1 | 6/2006 | Sher |
| 2006/0210997 A1 | 9/2006 | Myerson et al. |
| 2006/0216738 A1 | 9/2006 | Wada et al. |
| 2006/0229823 A1 | 10/2006 | Liu |
| 2006/0281105 A1 | 12/2006 | Li et al. |
| 2007/0027636 A1 | 2/2007 | Rabinowitz |
| 2007/0059707 A1 | 3/2007 | Cantor |
| 2007/0122805 A1 | 5/2007 | Cantor et al. |
| 2007/0178478 A1 | 8/2007 | Dhallan |
| 2007/0178501 A1 | 8/2007 | Rabinowitz |
| 2007/0184467 A1* | 8/2007 | Rabinowitz et al. ............. 435/6 |
| 2007/0202525 A1 | 8/2007 | Quake et al. |
| 2007/0202536 A1 | 8/2007 | Yamanishi et al. |
| 2007/0207466 A1 | 9/2007 | Cantor |
| 2007/0212689 A1 | 9/2007 | Bianchi |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0102455 A1 | 5/2008 | Poetter |
| 2008/0138809 A1 | 6/2008 | Kapur |
| 2008/0182244 A1 | 7/2008 | Tafas |
| 2008/0193927 A1 | 8/2008 | Mann et al. |
| 2008/0234142 A1 | 9/2008 | Lietz |
| 2008/0243398 A1 | 10/2008 | Rabinowitz |
| 2009/0023190 A1 | 1/2009 | Lao et al. |
| 2009/0029377 A1 | 1/2009 | Lo et al. |
| 2009/0087847 A1* | 4/2009 | Lo et al. ............................ 435/6 |
| 2009/0098534 A1 | 4/2009 | Weier et al. |
| 2009/0099041 A1 | 4/2009 | Church et al. |
| 2009/0176662 A1 | 7/2009 | Rigatti |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler et al. |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0285537 A1 | 11/2010 | Zimmermann |
| 2010/0291572 A1 | 11/2010 | Stoughton et al. |
| 2010/0323352 A1 | 12/2010 | Lo et al. |
| 2011/0033862 A1 | 2/2011 | Rabinowitz |
| 2011/0039724 A1 | 2/2011 | Lo et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0318734 A1 | 12/2011 | Lo et al. |
| 2012/0003635 A1 | 1/2012 | Lo et al. |
| 2012/0034603 A1 | 2/2012 | Oliphant et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2013/0017549 A1 | 1/2013 | Hong |
| 2013/0024127 A1 | 1/2013 | Stuelpnagel et al. |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0123120 A1 | 5/2013 | Zimmermann et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz et al. |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |

(56) References Cited

U.S. PATENT DOCUMENTS

| | | |
|---|---|---|
| 2013/0323731 A1 | 12/2013 | Lo et al. |
| 2014/0032128 A1 | 1/2014 | Rabinowitz et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0162269 A1 | 6/2014 | Rabinowitz et al. |
| 2014/0193816 A1 | 7/2014 | Rabinowitz et al. |
| 2014/0206552 A1 | 7/2014 | Rabinowitz et al. |
| 2014/0256569 A1 | 9/2014 | Rabinowitz et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0072872 A1 | 3/2015 | Rabinowitz et al. |
| 2015/0147815 A1 | 5/2015 | Babiarz et al. |
| 2015/0232938 A1 | 8/2015 | Mhatre et al. |
| 2015/0322507 A1 | 11/2015 | Zimmermann et al. |

FOREIGN PATENT DOCUMENTS

| | | |
|---|---|---|
| EP | 2902500 A1 | 8/2015 |
| GB | 2488358 | 8/2012 |
| JP | 2965699 | 8/1999 |
| JP | 2002-530121 A | 9/2002 |
| JP | 2004502466 A | 1/2004 |
| JP | 2004533243 A | 11/2004 |
| JP | 2005514956 A | 5/2005 |
| JP | 2005160470 A | 6/2005 |
| JP | 2006-254912 A | 9/2006 |
| WO | WO-0179851 | 10/2001 |
| WO | WO-0179851 A1 | 10/2001 |
| WO | WO 01/90419 | 11/2001 |
| WO | WO-0204672 A2 | 1/2002 |
| WO | WO-02055985 | 7/2002 |
| WO | WO-02055985 A2 | 7/2002 |
| WO | WO02076377 | 10/2002 |
| WO | WO03/031646 * | 4/2003 |
| WO | WO 03/031646 | 4/2003 |
| WO | WO-03050532 | 6/2003 |
| WO | WO-03050532 A1 | 6/2003 |
| WO | WO-03062441 A1 | 7/2003 |
| WO | WO-0190419 A9 | 11/2003 |
| WO | WO-03102595 | 12/2003 |
| WO | WO-03102595 A1 | 12/2003 |
| WO | WO-03106623 | 12/2003 |
| WO | WO-03106623 A2 | 12/2003 |
| WO | WO-2004/087863 | 10/2004 |
| WO | WO-2005021793 | 3/2005 |
| WO | WO-2005035725 A2 | 4/2005 |
| WO | WO-2005100401 | 10/2005 |
| WO | WO-2005123779 | 12/2005 |
| WO | WO 2007/057647 | 5/2007 |
| WO | WO 2007/062164 | 5/2007 |
| WO | WO-2007057647 A1 | 5/2007 |
| WO | WO-2007062164 A2 | 5/2007 |
| WO | WO 2007/070482 | 6/2007 |
| WO | WO-2007070482 A2 | 6/2007 |
| WO | WO 2007/132167 | 11/2007 |
| WO | WO-2007132167 A2 | 11/2007 |
| WO | WO2007147074 A2 | 12/2007 |
| WO | WO-2008024473 | 2/2008 |
| WO | WO-2008048931 | 4/2008 |
| WO | WO-2008051928 | 5/2008 |
| WO | WO-2008051928 A2 | 5/2008 |
| WO | WO-2008081451 A2 | 7/2008 |
| WO | WO 2008/115497 | 9/2008 |
| WO | WO-2008115497 A2 | 9/2008 |
| WO | WO-2008135837 | 11/2008 |
| WO | WO-2008157264 | 12/2008 |
| WO | WO 2009/013492 | 1/2009 |
| WO | WO 2009/013496 | 1/2009 |
| WO | WO-2009009769 | 1/2009 |
| WO | WO-2009013492 A1 | 1/2009 |
| WO | WO-2009013496 A1 | 1/2009 |
| WO | WO 2009/019455 | 2/2009 |
| WO | WO-2009019215 | 2/2009 |
| WO | WO-2009019455 A2 | 2/2009 |
| WO | WO-2009030100 | 3/2009 |
| WO | WO-2009032779 | 3/2009 |
| WO | WO-2009032781 | 3/2009 |
| WO | WO-2009033178 | 3/2009 |
| WO | WO-2009091934 | 7/2009 |
| WO | WO-2009092035 | 7/2009 |
| WO | WO 2009/105531 | 8/2009 |
| WO | WO-2009105531 A1 | 8/2009 |
| WO | WO 2009/146335 | 12/2009 |
| WO | WO-2009146335 A1 | 12/2009 |
| WO | WO 2010/017214 | 2/2010 |
| WO | WO-2010017214 A1 | 2/2010 |
| WO | WO2010075459 | 7/2010 |
| WO | WO 2011/041485 | 4/2011 |
| WO | WO-2011041485 A1 | 4/2011 |
| WO | WO2011057094 | 5/2011 |
| WO | WO2011087760 | 7/2011 |
| WO | WO 2011/146632 | 11/2011 |
| WO | WO-2011146632 A1 | 11/2011 |
| WO | WO 2012/088456 | 6/2012 |
| WO | WO2012071621 | 6/2012 |
| WO | WO2012083250 | 6/2012 |
| WO | WO-2012088456 A2 | 6/2012 |
| WO | WO 2012/108920 | 8/2012 |
| WO | WO-2012108920 A1 | 8/2012 |
| WO | WO2013030577 | 3/2013 |
| WO | WO-2013052557 | 4/2013 |
| WO | WO2013130848 | 9/2013 |
| WO | WO2014018080 | 1/2014 |

OTHER PUBLICATIONS

Bada et al., Computational Modeling of Structural Experimental Data, Methods in Enzymology, 317, pp. 470-491 (May 2000).
Beaumont et al., The Bayesian Revolution in Genetics, Nature Reviews Genetics, 5(4), pp. 251-261 (Apr. 2004).
Beer et al., The Biological Basis of Passage of Fetal Cellular Material into the Maternal Circulation, Annals New York Academy of Sciences, 731, pp. 21-35 (Sep. 7, 1994).
Beerenwinkel et al., Geno2pheno: Estimating Phenotypic Drug Resistance from HIV-1 Genotypes, Nucleic Acids Research, 31(13), pp. 3850-3855 (Jul. 2003).
Beerenwinkel et al., Methods for Optimizing Antiviral Combination Therapies, Bioinformatics, 19(3), pp. i16-i25 (Jul. 2003).
Bisignano et al., PGD and Aneuploidy Screening for 24 Chromosomes: Advantages and Disadvantages of Competing Platforms, Reproductive BioMedicine Online, 23(6), pp. 677-685 (Dec. 2011).
Bodenreider, The Unified Medical Language System (UMLS): Integrating Biomedical Terminology, Nucleic Acids Research, 32, pp. D267-D270 (Jan. 2004).
Breithaupt, The Future of Medicine, European Molecular Biology Organization, 2(6), pp. 465-467 (Jun. 2001).
Carnevale, "Attitudes of Mexican Geneticists Towards Prenatal Diagnosis and Selective Abortion," Am. J. Med. Genetics, vol. 75, pp. 426-431, 1998.
Chen et al., Noninvasive Prenatal Diagnosis of Fetal Trisomy 18 and Trisomy 13 by Maternal Plasma DNA Sequencing, PLoS ONE, 6(7), pp. 1-7 (Jul. 2011).
Chiu et al., Noninvasive Prenatal Diagnosis of Fetal Chromosomal Aneuploidy by Massively Parallel Genomic Sequencing of DNA in Maternal Plasma, PNAS, 105(51), pp. 20458-20463 (Dec. 23, 2008).
Chiu et al., Supporting Information, PNAS, 105(51), pp. 1-17 (Dec. 23, 2008).
Chiu et al., Non-Invasive Prenatal Diagnosis by Single Molecule Counting Technologies, Trends in Genetics, 25(7), pp. 324-331 (Jul. 2009).
Chiu et al., Maternal Plasma DNA Analysis with Massively Parallel Sequencing by Litigation for Noninvasive Prenatal Diagnosis of Trisomy 21, Clinical Chemistry, 56(3), pp. 459-463 (Mar. 2010).

(56) References Cited

OTHER PUBLICATIONS

Chiu et al., Non-Invasive Prenatal Assessment of Trisomy 21 by Multiplexed Maternal Plasma DNA Sequencing: Large Scale Validity Study, BMJ, 342(7790), pp. 1-9 (Jan. 2011).
Chu et al., Statistical Model for Whole Genome Sequencing and its Application to Minimally Invasive Diagnosis of Fetal Genetic Disease, Bioinformatics, 25(10), pp. 1244-1250 (May 15, 2009).
Chu et al., Statistical Considerations for Digital Approaches to Non-Invasive Fetal Genotyping, Bioinformatics, 26(22), pp. 2863-2866 (Sep. 23, 2010).
Chu et al., A Novel Approach Toward the Challenge of Accurately Quantifying Fetal DNA in Maternal Plasma, Prenatal diagnosis, 30, pp. 1226-1229 (Nov. 11, 2010).
Colella et al., QuantiSNP: an Objectives Bayes Hidden-Markov Model to Detect and Accurately Map Copy Number Variation Using SNP Genotyping Data, Nucleic Acids Research, 35(6), pp. 2013-2025 (Mar. 2007).
Cossu et al., Rh D/d Genotyping by Quantitative Polymerase Chain Reaction and Capillary Zone Electrophoresis, Electrophoresis, 17(12), pp. 1911-1915 (Dec. 1996).
Coyle et al., Standards for Detailed Clinical Models as the Basis for Medical Data Exchange and Decision Support, International Journal of Medical Informatics, 69(2), pp. 157-174 (Mar. 2003).
Daruwala et al., A Versatile Statistical Analysis Algorithm to Detect Genome Copy Number Variation, PNAS, 101(46), pp. 16292-16297(Nov. 16, 2004).
DeAngelis et al., Solid-phase Reversible Immobilization for the Isolation of PCR Products, Nucleic Acids Research, 23(22), pp. 4742-4743 (Nov. 25, 1995).
Devaney et al., Noninvasive Fetal Sex Determination Using Cell-Free Fetal DNA: A Systematic Review and Meta-analysis, JAMA, 306(6), pp. 627-636 (Aug. 10, 2011).
Dhallan et al., Methods to Increase the Percentage of Free Fetal DNA Recovered from the Maternal Circulation, JAMA, 291(9), pp. 1114-1119 (Mar. 3, 2004).
Dhallan et al., A Non-Invasive Test for Prenatal Diagnosis Based on Fetal DNA Present in Maternal Blood: A Preliminary Study, Lancet, 369(9560), pp. 474-481 (Feb. 2007).
Donoso et al., Current Value of Preimplantation Genetic Aneuploidy Screening in IVF, Hum. Reprod. Update, 13(1), pp. 15-25 (Jan./Feb. 2007).
Ehrich et al., Noninvasive Detection of Fetal Trisomy 21 by Sequencing of DNA in Maternal Blood: A Study in a Clinical Setting, AJOG, 204(3), pp. 205.e1-205.e11 (Mar. 2011).
Eichler et al., Mild Course of Fetal RhD Haemolytic Disease due to Maternal Alloimmunisation to Paternal HLA Class I and II Antigens, Vox Sang, 68(4), pp. 243-247 (1995).
Ellonen, "Development of SNP microarray for supplementary paternity testing," Int'l Congress Series, vol. 1261, pp. 12-14, 2004.
Fan et al., Noninvasive Diagnosis of Fetal Aneuploidy by Shotgun Sequencing DNA from Maternal Blood, PNAS, 105(42), pp. 16266-16271 (Oct. 2008).
Fiorentino et al., Development and Clinical Application of a Strategy for Preimplantation Genetic Diagnosis of Single Gene Disorders Combined with HLA Matching, Molecular Human Reproduction, 10(6), pp. 445-460 (Jun. 2004).
Fiorentino et al., Short Tandem Repeats Haplotyping of the HLA Region in Preimplantation HLA Matching, European J. Human Genetics, 13(8), pp. 953-958 (Aug. 2005).
Fiorentino et al., Strategies and Clinical Outcome of 250 Cycles of Preimplantation Genetic Diagnosis for Single Gene Disorders, Human Reproduction, 21(3), pp. 670-684 (Mar. 2006).
Fixed Medium, Academic Press Dictionary of Science and Technology, Retrieved from www.credoreference.com/entry/apdst/fixed_medium (Sep. 1992, Accessed on Nov. 18, 2009).
Freeman et al., Copy Number Variation: New Insights in Genome Diversity, Genome Research, 16(8), pp. 949-961 (Aug. 2006).
Ganshirt-Ahlert et al., Three Cases of 45,X/46,XYnf Mosaicism, Hum Genet, 76(2), pp. 153-156 (Jun. 1987).
Ganshirt-Ahlert et al., Ratio of Fetal to Maternal DNA is Less Than 1 in 5000 at different Gestational Ages in Maternal Blood, Clinical Genetics, 38(1), pp. 38-43 (Jul. 1990).
Ganshirt-Ahlert et al., Fetal DNA in Uterine Vein Blood, Obstetrics & Gynecology, 80(4), pp. 601-603 (Oct. 1992).
Gardina et al., Ploidy Status and Copy Number Aberrations in Primary Glioblastomas Defined by Integrated Analysis of Allelic Ratios, Signal Ratios and Loss of Heterozygosity Using 500K SNP Mapping Arrays, BMC Genomics, 9(489), pp. 1-16 (Oct. 2008).
Ghanta et al., Non-Invasive Prenatal Detection of Trisomy 21 Using Tandem Single Nucleotide Polymorphisms, PLoS ONE, 5(10), pp. 1-10 (Oct. 2010).
Gjertson, "Assessing probability of paternity and the product rule in DNA systems," Genetica, vol. 96, pp. 89-98, 1995.
Greenwalt et al., The Quantification of Fetomaternal Hemorrhage by an Enzyme-Linked Antibody Test with Glutaraldehyde Fixation, Vox Sang, 63(4), pp. 238-271 (1992).
Guetta, "Analysis of Fetal Blood Cells in the Maternal Circulation: Challenges, Ongoing Efforts, and Potential Solutions," Stem Cells and Development, vol. 13, pp. 93-99, 2004.
Harper et al., Recent Advances and Future Developments in PGD, Prenatal Diagnosis, 19, pp. 1193-1199 (Dec. 1999).
Harton et al., "Preimplantation Genetic Testing for Marfan Syndrome", Molecular Human Reproduction, vol. 2, No. 9, pp. 713-715 (Sep. 1996).
Hellani et al., Clinical Application of Multiple Displacement Amplification in Preimplantation Genetic Diagnosis, Reproductive BioMedicine Online, 10(3), pp. 376-380 (Jan. 13, 2005).
Hojsgaard et al., BIFROST—Block Recursive Models Induced from Relevant Knowledge, Observations, and Statistical Techniques, Computational Statistics & Data Analysis, 19(2), pp. 155-175 (Feb. 1995).
Hollox et al., Extensive Normal Copy Number Variation of a β-Defensin Antimicrobial-Gene Cluster, Am. J. Hum. Genet., 73(3), pp. 591-600 (Sep. 2003).
Homer et al., Resolving Individuals Contributing Trace Amounts of DNA to Highly Complex Mixtures Using High-Density SNP Genotyping Microarrays, PLOS Genetics, 4(8), pp. 1-9 (Aug. 2008).
Hu et al., Aneuploidy Detection in Single Cells Using DNA Array-Based Comparative Genomic Hybridiation, Molecular Human Reproduction, 10(4), pp. 283-289 (Apr. 2004).
Kazakov et al., Extracellular DNA in the Blood of Pregnant Women, Tsitologia, 37(3), pp. 1-8 (1995).
Kijak et al., Discrepant Results in the Interpretation of HIV-1 Drug-Resistance Genotypic Data Among Widely Used Algorithms, HIV Medicine, 4(1), pp. 72-78 (Jan. 2003).
Kuliev et al., Thirteen Years' Experience on Preimplantation Diagnosis: Report of the Fifth International Symposium on Preimplantation Genetics, Reproductive BioMedicine Online, 8(2), pp. 229-235 (Dec. 22, 2003).
Lambert-Messerlian et al., Adjustment of Serum Markers in First Trimester Screening, Journal of Medical Screening, 16(2), pp. 102-103 (2009).
Li et al., Non-Invasive Prenatal Diagnosis Using Cell-Free Fetal DNA in Maternal Plasma from PGD Pregnancies, Reproductive BioMedicine Online, 19(5), pp. 714-720 (Nov. 2009).
Liao et al., Targeted Massively Parallel Sequencing of Maternal Plasma DNA Permits Efficient and Unbiased Detection of Fetal Alleles, Clin Chem, 57(1), pp. 92-101 (Jan. 2011).
Lindroos et al., Genotyping SNPs by Minisequencing Primer Extension Using Oligonucleotide Microarrays, Methods in Molecular Biology, (2003) vol. 212 pp. 149-165.
Lo et al., Prenatal Sex Determination by DNA Amplification from Maternal Peripheral Blood, The Lancet, 2(8676), pp. 1363-1365 (Dec. 9, 1989).
Lo et al., Detection of Single-Copy Fetal DNA Sequence from Maternal Blood, The Lancet, 335, pp. 1463-1464 (Jun. 16, 1990).
Lo et al., Letters to the Editor: Prenatal Determination of Fetal RhD Status by Analysis of Peripheral Blood of Rhesus Negative Mothers, The Lancet, 341, pp. 1147-1148 (May 1, 1993).

(56) References Cited

OTHER PUBLICATIONS

Lo et al., Detection of Fetal RhD Sequence from Peripheral Blood of Sensitized RhD-Negative Pregnant Women, British Journal of Haematology, 87, pp. 658-660 (Apr. 22, 1994).
Lo et al., Prenatal Determination of Fetal Rhesus D Status by DNA Amplification of Peripheral Blood of Rhesus-Negative Mothers, Annals New York Academy of Sciences, 731, pp. 229-236 (Sep. 7, 1994).
Lo et al., Strategies for the Detection of Autosomal Fetal DNA Sequence from Maternal Peripheral Blood, Annals New York Academy of Sciences, 731, pp. 204-213 (Sep. 7, 1994).
Lo et al., Rapid Clearance of Fetal DNA from Maternal Plasma, Am. J. Hum. Genet., 64(1), pp. 218-224 (Jan. 1999).
Lo et al., Letter to the Editor: Free Fetal DNA in Maternal Circulation, JAMA, 292(23), pp. 2835-2836 (Dec. 15, 2004).
Lo et al., Plasma Placental RNA Allelic Ratio Permits Noninvasive Prenatal Chromosomal Aneuploidy Detection, Nature Medicine, 13(2), pp. 218-223 (Feb. 2007).
Lo et al., Digital PCR for the Molecular Detection of Fetal Chromosomal Aneuploidy, PNAS, 104(32), pp. 13116-13121 (Aug. 7, 2007).
Lo, Fetal Nucleic Acids in Maternal Plasma: Toward the Development of Noninvasive Prenatal Diagnosis of Fetal Chromosomal Aneuploidies, Ann. N.Y. Acad. Sci., 1137, pp. 140-143 (Aug. 2008).
Lo et al., Maternal Plasma DNA Sequencing Reveals the Genome-Wide Genetic and Mutational Profile of the Fetus, Science Translational Medicine, 2(61), pp. 1-13 (Dec. 2010).
Lun et al., Noninvasive Prenatal Diagnosis of Monogenic Diseases by Digital Size Selection and Relative Mutation Dosage on DNA in Maternal Plasma, PNAS, 105(50), pp. 19920-19925 (Dec. 16, 2008).
Maniatis et al., Molecular Cloning: A Laboratory Manual, Cold Spring Harbor Laboratory, pp. 458-459 (Jul. 1982).
Mansfield, Diagnosis of Down Syndrome and Other Aneuploidies Using Quantitative Polymerase Chain Reaction and Small Tandem Repeat Polymorphisms, Human Molecular Genetics, 2(1), pp. 43-50 (Jan. 1993).
May, Robert M., "How Many Species are There on Earth?," Science (241) pp. 1441-1449 (Sep. 16, 1988).
McCray et al., Aggregating UMLS Semantic Types for Reducing Conceptual Complexity, Medinfo2001, 84, pp. 216-220 (Jun. 2001).
Munne et al., Chromosome Abnormalities in Human Embryos, Textbook of Assisted Reproductive Techniques, pp. 355-377 (Jul. 2004).
Myers et al., "Accurate Detection of Aneuploidies in Array CGH and Gene Expression Microarray Data", Bioinformatics, 2004, 20(18), 3533-3543 (2004).
Nannya et al., A Robust Algorithm for Copy Number Detection Using High-density Oligonucleotide Single Nucleotide Polymorphism Genotyping Arrays, Cancer Res, 65(14), pp. 6071-6079 (Jul. 15, 2005).
Ogino et al., Bayesian Analysis and Risk Assessment in Genetic Counseling and Testing, Journal of Molecular Diagnostics, 6(1), pp. 1-9 (Feb. 2004).
Orozco et al., Placental Release of Distinct DNA-Associated Micro-Particles into Maternal Circulation: Reflective of Gestation Time and Preeclampsia, Placenta, 30(10), pp. 891-897 (Oct. 2009).
Ozawa et al., Two Families with Fukuyama Congenital Muscular Dystrophy that Underwent In Utero Diagnosis Based on Polymorphism Analysis, Clinical Muscular Dystrophy: Research in Immunology and Genetic Counseling—FY 1994/1995, pp. 13-15 (Mar. 28, 1996).
Page et al., Chromosome Choreography: The Meiotic Ballet, Science, 301, pp. 785-789 (Aug. 8, 2003).
Palomaki et al., DNA Sequencing of Maternal Plasma to Detect Down Syndrome: An International Clinical Validation Study, Genetics in Medicine, 13(11), pp. 913-920 (Nov. 2011).
Papageorgiou et al., Fetal-Specific DNA Methylation Ratio Permits Noninvasive Prenatal Diagnosis of Trisomy 21, Nature Medicine, 17, pp. 510-513 (Mar. 6, 2011).

Pena et al., Reviews: Paternity Testing in the DNA Era, TIG, 10(6), pp. 204-209 (Jun. 1994).
Perry et al., The Fine-Scale and Complex Architecture of Human Copy-Number Variation, The American Journal of Human Genetics, 82, pp. 685-695 (Mar. 2008).
Peters et al., Noninvasive Prenatal Diagnosis of a Fetal Microdeletion Syndrome, The New England Journal of Medicine, 365(19), pp. 1847-1848 (Nov. 10, 2011).
Pfaffl, Relative Expression Software Tool (REST © ) for Group-Wise Comparison and Statistical Analysis of Relative Expression Results in real-Time PCR, Nucleic Acids Research, 30(9), pp. 1-10 (May 1, 2002).
Phillips et al., Resolving Relationship Tests that Show Ambiguous STR Results Using Autosomal SNPs as Supplementary Markers, Forensic Science International: Genetics 2, 2(3), pp. 198-204 (Jun. 2008).
Porreca et al., Multiplex Amplification of Large Sets of Human Exons, Nature Methods, 4(11), pp. 931-936 (Oct. 2007).
Rabinowitz et al., Accurate Prediction of HIV-1 Drug Response from the Reverse Transcriptase and Protease Amino Acid Sequences Using Sparse Models Created by Convex Optimization, Bioinformatics, 22(5), pp. 541-549 (Mar. 2006).
Rechitsky et al., Preimplantation Genetic Diagnosis with HLA Matching, Reproductive BioMedicine Online, 9(2), pp. 210-221 (Jun. 23, 2004).
Renwick et al., Proof of Principle and First Cases Using Preimplantation Genetic Haplotyping—A Paradigm Shift for Embryo Diagnosis, Reproductive BioMedicine Online, 13(1), pp. 110-119 (Apr. 28, 2006).
Roper et al., Forensic Aspects of DNA-Based Human Identity Testing, Journal of Forensic Nursing 4(4), pp. 150-156 (2008).
Sander, Genetic Medicine and the Future of Health Care, Science, 287(5460), pp. 1977-1978 (Mar. 17, 2000).
Sebat et al., Strong Association of De Novo Copy Number Mutations with Autism, Science, 316, pp. 445-449 (Apr. 20, 2007).
Sehnert et al., Optimal Detection of Fetal Chromosomal Abnormalities by Massively Parallel DNA Sequencing of Cell-Free Fetal DNA from Maternal Blood, Clinical Chemistry, 57(7), pp. 1-8 (Apr. 25, 2011).
Shaw-Smith et al. "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., Issue 41, pp. 241-248 (Apr. 2004).
Simpson et al., Fetal Cells in Maternal Blood: Overview and Historical Perspective, Annals New York Academy of Sciences, 731, pp. 1-8 (Sep. 1994).
Slater et al., High-Resolution Identification of Chromosomal Abnormalities Using Oligonucleotide Arrays Containing 116,204 SNPs, Am. J. Human Genetics, 77(5), pp. 709-726 (Nov. 2005).
Sparks et al., Selective Analysis of Cell-Free DNA in Maternal Blood for Evaluation of Fetal Trisomy, Prenatal Diagnosis, 32, pp. 1-7 (Jan. 6, 2012).
Sparks et al., Non-Invasive Prenatal Detection and Selective Analysis of Cell-Free DNA Obtained from Maternal Blood: Evaluation for Trisomy 21 and Trisomy 18, American Journal of Obstetrics & Gynecology (Jan. 27, 2012).
Stephens, et al., A Comparison of Bayesian Methods for Haplotype Reconstruction from Population Genotype Data, Am. J. Human Genetics, 73(5), pp. 1162-1169 (Nov. 1, 2003).
Stevens et al., Ontology-Based Knowledge Representation for Bioinformatics, Briefings in Bioinformatics, 1(4), pp. 398-414 (Nov. 2000).
Steyerberg et al., Application of Shrinkage Techniques in Logistic Regression Analysis: A Case Study, Statistical Neerlandica, 55(1), pp. 76-88 (Mar. 2001).
Strom et al., Neonatal Outcome of Preimplantation Genetic Diagnosis by Polar Body Removal: the first 109 infants, Pediatrics, 4, pp. 650-653 (Oct. 2000).
Stroun et al., Prehistory of the Notion of Circulating Nucleic Acids in Plasma/Serum (CNAPS): Birth of a Hypothesis, Ann. N.Y. Acad. Sci., 1075, pp. 10-20 (Sep. 2006).

(56) References Cited

OTHER PUBLICATIONS

Sweetkind-Singer, Log-Penalized Linear Regression, International Symposium on Information Theory, pp. 286 (Jun. 29-Jul. 4, 2003).
Thomas et al., The Time of Appearance and Disappearance of Fetal DNA from the Maternal Circulation, Prenatal Diagnosis, 15(7), pp. 641-646 (Jul. 1995).
Tong et al., Noninvasive Prenatal Detection of Trisomy 21 by an Epigenetic-Genetic Chromosome-Dosage Approach, Clinical Chemistry, 56(1), pp. 90-98 (Jan. 2010).
Troyanskaya et al., A Bayesian Framework for Combining Heterogeneous Data Sources for Gene Function Prediction, Proc. Nat. Academy of Sci., 100(14), pp. 8348-8353 (Jul. 8, 2003).
Tsui et al., Non-Invasive Prenatal Detection of Fetal Trisomy 18 by RNA-SNP Allelic Ratio Analysis Using Maternal Plasma SERPINB2 mRNA: A Feasibility Study, Prenatal Diagnosis, 29(11), pp. 1031-1037 (Nov. 2009).
Turner et al., Massively Parallel Exon Capture and Library-Free Resequencing Across 16 Genomes, Nature Methods, 6(5), pp. 315-316 (May 2009).
Verlinsky et al., Over a Decade of Experience with Preimplantation Genetic Diagnosis, Fertility and Sterility, 82(2), pp. 302-303 (Aug. 2004).
Wagner et al, "Non-Invasive Prenatal Paternity Testing from Maternal Blood", Int. J. Legal Med. 123: 75-79 (Oct. 24, 2008).
Wells, Advances in Preimplantation Genetic Diagnosis, European J. of Obstetrics and Gynecology and Reproductive Biology, 115S, pp. S97-S101 (Jul. 1, 2004).
Wells, Microarray for Analysis and Diagnosis of Human Embryos, 12th International Congress on Prenatal Diagnosis and Therapy, pp. 9-17 (Jun. 24-27, 2004).
Wilton, Preimplantation Genetic Diagnosis and Chromosome Analysis of Blastomeres Using Comparative Genomic Hybridization, Hum. Record. Update, (11)1, pp. 33-41 (Jan./Feb. 2005).
Wilton et al. Birth of a Health Infant After Preimplantation Confirmation of Euploidy by Comparative Genomic Hybridization, N. Engl. J. Med., 345(21), pp. 1537-1541(Nov. 22, 2001).
Yeh et al., Knowledge Acquisition, Consistency Checking and Concurrency Control for Gene Ontology (GO), Bioinformatics, 19(2), pp. 241-248 (Jan. 2003).
Zhao et al., An Integrated View of Copy Number and Allelic Alterations in the Cancer Genome Using Single Nucleotide Polymorphism Arrays, Cancer Research, 64, pp. 3060-3071 (May 1, 2004).
European Examination Report in 08 742 125.1 dated Feb. 12, 2010.
Extended European Search Report in 06 838 311.6 dated Dec. 30, 2008.
PCT International Preliminary Report on Patentability based on PCT/US2006/045281 dated May 27, 2008.
PCT International Search Report based on PCT/US2006/045281 dated Sep. 28, 2007.
PCT International Search Report based on PCT/US2008/003547 dated Apr. 15, 2009.
PCT International Search Report based on PCT/US2009/034506 dated Jul. 8, 2009.
PCT International Search Report based on PCT/US2009/045335 dated Jul. 27, 2009.
PCT International Search Report based on PCT/US2009/052730 dated Sep. 28, 2009.
PCT International Search Report based on PCT/US2010/050824 dated Nov. 15, 2010.
PCT International Search Report based on PCT/US2011/037018 dated Sep. 27, 2011.
PCT International Search Report based on PCT/US2011/061506 dated Mar. 16, 2012.
PCT International Search Report in PCT/US2011/066938 dated Jun. 20, 2012.
PCT International Search Report in PCT/US2012/066339 dated Mar. 5, 2013.
PCT International Search Report in PCT/US2013/028378 dated May 28, 2013.
Office Action in U.S. Appl. No. 11/004,274 mailed May 13, 2008.
Office Action in U.S. Appl. No. 11/004,274 mailed Feb. 4, 2009.
Office Action in U.S. Appl. No. 11/004,274 mailed Nov. 24, 2009.
Office Action in U.S. Appl. No. 11/004,274 mailed Mar. 2, 2011.
Office Action in U.S. Appl. No. 11/496,982 mailed May 27, 2010.
Office Action in U.S. Appl. No. 11/496,982 mailed Jan. 21, 2011.
Office Action in U.S. Appl. No. 11/634,550 mailed Aug. 4, 2010.
Office Action in U.S. Appl. No. 11/634,550 mailed Jan. 24, 2011.
Office Action in U.S. Appl. No. 11/603,406 mailed Aug. 19, 2010.
Office Action in U.S. Appl. No. 11/603,406 mailed Feb. 18, 2011.
Office Action in U.S. Appl. No. 12/076,348 mailed Aug. 20, 2010.
Office Action in U.S. Appl. No. 12/076,348 mailed Mar. 4, 2011.
Office Action in U.S. Appl. No. 12/076,348 mailed Feb. 8, 2013.
Office Action in U.S. Appl. No. 11/603,406 mailed Mar. 14, 2013.
International Application No. PCT/US2013/028378, International Search Report and Written Opinion mailed May 28, 2013, 11 pgs.
"Competitive PCR Guide", TaKaRa Biomedicals, Lit. # L0126 Rev. 8/99, 9 pgs.
"Ion AmpliSeq Comprehensive Cancer Panel", product brochure, Life Technologies Corporation. Retrieved from the Internet <URL: https://tools.lifetechnologies.com/content/sfs/brochures/Ion_CompCancerPanel_Flyer.pdf>, (2012),2 pgs.
"Ion AmpliSeq Designer Provides Full Flexibility to Sequence Genes of Your Choice", product brochure, Life Technologies Corporation. Retrieved from the Internet <URL: http://tools.lifetechnologies.com/content/sfs/brochures/IonAmpliSeq_CustomPanels_AppNote_CO111038_06042012.pdf>, (2012),4 pgs.
"Primer3", information sheet, Sourceforge.net. [retrieved on Nov. 12, 2012]. Retrieved from the Internet: <URL: http://primer3.sourceforge.net/>, (Oct. 26, 2009),1 pg.
Agarwal, et al., "Commercial Landscape of Noninvasive Prenatal Testing in the United States", Prenatal Diagnosis, 33, (2013),521-531.
Alkan, et al., "Personalized Copy Number and Segmental Duplication Maps Using Next-Generation Sequencing", Nature Genetics, vol. 41, No. 10, (Oct. 2009),1061-1068.
Allawi, et al., "Thermodynamics of internal C•T Mismatches in DNA", Nucleic Acids Research, vol. 26, No. 11, (1998),2694-2701.
Benn, et al., "Non-Invasive prenatal Diagnosis for Down Syndrome: the Paradigm Will Shift, but Slowly", Ultrasound Obstet. Gynecol., 39, (2012),127-130.
Benn, et al., "Non-Invasive Prenatal Testing for Aneuploidy: Current Status and Future Prospects", Ultrasound Obstet. Gynecol., 42, (2013),15-33.
Bermudez, et al., "Single-cell sequencing and mini-sequencing for preimplantation genetic diagnosis", Prenatal Diagnosis, 23 (2003), 669-677.
Birch, et al., "Accurate and Robust Quantification of Circulating Fetal and Total DNA in Maternal Plasma from 5 to 41 Weeks of Gestation", Clinical Chemistry, vol. 51, No. 2, (2005),312-320.
Chetty, et al., "Uptake of Noninvasive Prenatal Testing (NIPT) in Women Following Positive Aneuploidy Screening", Prenatal Diagnosis, 33, (2013),542-546.
Dohm, et al., "Substantial Biases in Ultra-Short Read Data Sets From High-Throughput DNA Sequencing", Nucleic Acids Research, vol. 36, No. 16, e105, (2008),10 pgs.
Fan, et al., "Non-Invasive Prenatal Measurement of the Fetal Genome", Nature, doi:10.1038/nature11251 (with Supplemental Information), (2012),26 pgs.
Guerra, et al., "Terminal Contributions for Duplex Oligonucleotide Thermodynamic Properties in the Context of Nearest Neighbor Models", Biopolymers, vol. 95, No. 3, (2011),194-201.
Guichoux, et al., "Current Trends in Microsatellite Genotyping", Molecular Ecology Resources, 11, (2011),591-611.
Hellani, et al., "Multiple displacement amplification on single cell and possible PGD applications", Molecular Human Reproduction, vol. 10, No. 11, advance access publication (Oct. 1, 2004),847-852.
Johnson, et al., "Comprehensive Analysis of Karyotypic Mosaicism Between Trophectoderm and Inner Cell Mass", Molecular Human Reproduction, vol. 16, No. 12, (2010),944-949.

(56) References Cited

OTHER PUBLICATIONS

Johnson, et al., "Preclinical Validation of a Microarray Method for Full Molecular Karyotyping of Blastomeres in a 24-h Protocol", Human Reproduction, vol. 25, No. 4, (2010),1066-1075.
Kaplinski, et al., "MultiPLX: Automatic Grouping and Evaluation of PCR Primers", Bioinformatics (Advance Access publication), vol. 21, No. 8, (2005),1701-1702.
Konfortov, et al., "An Efficient Method for Multi-Locus Molecular Haplotyping", Nucleic Acids Research, vol. 35, No. 1, e6, (2007),8 pgs.
Lathi, et al., "Informatics Enhanced Snp Microarray Analysis of 30 Miscarriage Samples Compared to Routine Cytogenetics", PLoS ONE, vol. 7, Issue 3, e31282, (Mar. 2012),5 pgs.
Leary, et al., "Detection of Chromosomal Alterations in the Circulation of Cancer Patients with Whole-Genome Sequencing", Science Translational Medicine, vol. 4, Issue 162, (Nov. 28, 2012),12 pgs.
Li, et al., "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, (2012),1 pg.
Li, et al., "Size Separation of Circulatory DNA in Maternal Plasma Permits Ready Detection of Fetal DNA Polymorphisms", Clinical Chemistry, vol. 50, No. 6, (2004),1002-1011.
Lo, et al., "Fetal Nucleic Acids in Maternal Blood: the Promises", Clin. Chem. Lab. Med., vol. 50, No. 6, (2012),995-998.
Lo, et al., "Presence of Fetal DNA in Maternal Plasma and Serum", The Lancet, vol. 350, (Aug. 16, 1997),485-487.
Lo, et al., "Quantitative Analysis of Fetal DNA in Maternal Plasma and Serum: Implications for Noninvasive Prenatal Diagnosis", Am. J. Hum. Genet. 62, (1998),768-775.
Lo, et al., "Two-way cell traffic between mother and fetus: biologic and clinical implications", Blood, vol. 88, No. 11, (Dec. 1, 1996),4390-4395.
Lo, "Non-Invasive Prenatal Diagnosis by Massively parallel Sequencing of Maternal Plasma DNA", Open Biol 2: 120086, (2012),1-5.
Mennuti, et al., "Is It Time to Sound an Alarm About False-Positive Cell-Free Dna Testing for Fetal Aneuploidy?", American Journal of Obstetrics, (2013),5 pgs.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, vol. 19, No. 4, (2013),318-329.
Murtaza, et al., "Non-Invasive Analysis of Acquired Resistance to Cancer Therapy by Sequencing of Plasma DNA", Nature (doi:10.1038/nature12065), (2013),6 pgs.
Nicolaides, et al., "Noninvasive Prenatal Testing for Fetal Trisomies in a Routinely Screened First-Trimester Population", American Journal of Obstetrics (article in press), 207, (2012),1.e1—1.e6.
Nicolaides, et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, (Apr. 26, 2013),575-579.
Nicolaides, et al., "Prenatal Detection of Fetal Triploidy from Cell-Free DNA Testing in Maternal Blood", Fetal Diagnosis and Therapy, (Oct. 10, 2013),1-6.
Paez, et al., "Genome coverage and sequence fidelity of Φ29 polymerase-based multiple strand displacement whole genome amplification", Nucleic Acids Research, vol. 32, No. 9, (May 18, 2004),1-11.
Palomaki, et al., "DNA Sequencing of Maternal Plasma Reliably Identifies Trisomy 18 and Trisomy 13 as Well as Down Syndrome: an International Collaborative Study", Genetics in Medicine, (2012),10 pgs.

Pertl, et al., "Detection of Male and Female Fetal DNA in Maternal Plasma by Multiplex Fluorescent Polymerase Chain Reaction Amplification of Short Tandem Repeats", Hum. Genet., 106, (2000),45-49.
Rabinowitz, et al., "Non-Invasive Prenatal Aneuploidy Testing of Chromosomes 13, 18, 21, X, and Y Using Targeted Sequencing of Polymorphic Loci", The American Society of Human Genetics, meeting poster, (2012).
Rabinowitz, et al., "Origins and Rates of Aneuploidy in Human Blastomeres", Fertility and Sterility, vol. 97, No. 2, (Feb. 2012),395-401.
Rava, et al., "Circulating Fetal Cell-Free DNA Fraction Differ in Autosomal Aneuploidies and Monosomy X", Clinical Chemistry (papers in press), vol. 60, No. 1, (Sep. 17, 2013),8 pgs.
Ryan, et al., "Informatics-Based, Highly Accurate, Noninvasive Prenatal Paternity Testing", Genetics in Medicine (advance online publication), (Dec. 20, 2012),5 pgs.
Samango-Sprouse, et al., "SNP-Based Non-Invasive Prenatal Testing Detects Sex Chromosome Aneuploidies with High Accuracy", Prenatal Diagnosis, vol. 33, (2013),1-7.
Santalucia, Jr., et al., "Improved Nearest-Neighbor Parameters for Predicting DNA Duplex Stability", Biochemistry, 35, (1996),3555-3562.
Santalucia, Jr., et al., "The Thermodynamics of DNA Structural Motifs", Annu. Rev. Biophys. Biomol. Struct., 33, (2004),415-440.
Spits, et al., "Optimization and Evaluation of Single-Cell Whole Genome Multiple Displacement Amplification", Human Mutation, vol. 27, No. 5, (2006),496-503.
Strom, et al., "Three births after preimplantation genetic diagnosis for cystic fibrosis with sequential first and second polar body analysis", American Journal of Obstetrics and Gynecology, vol. 178, No. 6, (1998),1298-1306.
Tang, et al., "Detection of Fetal-Derived Paternally Inherited X-Chromosome Polymorphisms in Maternal Plasma", Clinical Chemistry vol. 45, No. 11, (1999),2033-2035.
Wang, et al., "Gestational Age and Maternal Weight Effects on Fetal Cell-Free DNA in Maternal Plasma", Prenatal Diagnosis, vol. 33, (2013),662-666.
Wapner, et al., "Chromosomal Microarray Versus Karyotyping for Prenatal Diagnosis", The New England Journal of Medicine, vol. 367, No. 23, (Dec. 6, 2012),2175-2184.
Watkins, Jr., et al., "Thermodynamic contributions of single internal rA •dA, rC • dC, rG • dG and rU • dT mismatches in Rna/Dna duplexes", Nucleic Acids Research, vol. 39, No. 5, (Nov. 10, 2010),1894-1902.
Xia, et al., "Thermodynamic Parameters for an Expanded Nearest-Neighbor Model for Formation of RNA Duplexes with Watson-Crick Base Pairs", Biochemistry, 37, (1998),14719-14735.
Zhou, et al., "Counting Alleles Reveals a Connection Between Chromosome 18q Loss and Vascular Invasion", Nature Biotechnology, vol. 19, (Jan. 2001),78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, (2012),1-9.
"Finishing the Euchromatic Sequence of the Human Genome", Nature vol. 431, (Oct. 21, 2004),931-945.
"Nucleic Acids, Linkers and Primers: Random Primers" New England BioLabs 1998/99 Catalog, (1998), 121 and 284.
"Genetics Home Reference", http://ghr.nlm.nih.gov/handbook/genomicresearch/snp, (Feb. 28, 2014),1-2.
Ashoor, et al., "Fetal Fraction in Maternal Plasma Cell-Free DNA at 11-13 Weeks' Gestation: Effect of Maternal and Fetal Factors", Fetal Diagnosis Therapy, (May 4, 2012),1-7.
Cairns, "Homozygous Deletions of 9p21 in Primary Human Bladder Tumors Detected by Comparative Multiplex Polymerase Chain Reaction", Cancer Research vol. 54, (1994), 1422-1424.
Caliendo, "Multiplex PCR and Emerging Technologies for the Detection of Respiratory Pathogens", Clinical Infection Diseases vol. 52, Suppl. 4, (2011), S326-S330.
Dieffenbach, "General Concepts for PCR Primer Design", PCR Methods Appl. vol. 3, (1993), 30-37.

(56) References Cited

OTHER PUBLICATIONS

Dolganov, et al., "A Novel Method of Gene Transcript Profiling in Airway Biopsy Homogenates Reveals Increased Expression of a Na +-K+-CL-Contransporter (NKCC1) in Asthmatic Subjects", Genome Res. 2001, vol. 11, (2001), 1473-1483.

Guichoux E., "Current Trends in Microsatellite Genotyping", Molecular Ecology Resources, vol. 11, (2011), 591-611.

Hardenbol, et al., "Highly multiplexed molecular inversion probe genotyping: Over 10,000 targeted SNP's genotyped in a singled tube assay", Genome Research, 15, (2005), 269-275.

Hoogendoorn, et al., "Genotyping Single Nucleotide Polymorphisms by Primer Extension and High Performance Liquid Chromatography", Hum Genet vol. 104, (1999), 89-93.

"Multiplexing with RainDrop Digital PCR", RainDance Technologies Application Note, (2013), 1-2.

Perkel, "Overcoming the Challenges of Multiplex PCR", Biocompare Editorial Article, Oct. 23, 2012, 1-5.

Renwick, et al., "Proof of Principle and First Cases Using Preimplantation Genetic Haplotyping—A Paradigm Shift for Embryo Diagnosis", Reproductive BioMedicine Online, vol. 13, No. 1, (2006), 110-119.

Roux, "Optimization and Troubleshooting in PCR", PCR Methods Appl. vol. 4, (1995), 185-194.

Sint, "Advances in Multiplex PCR: Balancing Primer Efficiencies and Improving Detection Success", Methods in Ecology and Evolution vol. 3, (2012), 898-905.

Spiro, "A Bead-Based Method for Multiplexed Identification and Quantitation of DNA Sequences Using Flow Cytometry", Applied and Environmental Microbiology, Oct. 2000, vol. 66, No. 10, 4258-4265.

Wang, "Allele quantification using molecular inversion probes (MIP)", Nucleic Acids Research, vol. 33, No. 21 , (Nov. 28, 2005), 14 pgs.

Wang, et al., "A Genotyping System Capable of Simultaneously Analyzing >1000 Single Nucleotide Polymorphisms in a Haploid Genome", Genome Res., vol. 15, (2005) 276-283.

Wells, "Detailed Chromosomal and Molecular Genetic Analysis of Single Cells by Whole Genome Amplification and Comparative Genomic Hybridisation", Nucleic Acids Research, 1999, vol. 27, No. 4, 1214-1218.

Wen, "Universal Multiples PCR: A Novel Method of Simultaneous Amplification of Multiple DNA Fragments", Plant Methods vol. 8, No. 32, (2012), 1-9.

Zhang, "Quantifying RNA Allelic Ratios by Microfluidic Multiplex PCR and Sequencing", Nature Methods, vol. 11, No. 1, Jan. 2014, 51-56.

A Bead-Based Method for Multiplexed Identification and Quantitation of DNA Sequences Using Flow Cytometry, Applied and Environmental Microbiology, Oct. 2000, vol. 66, No. 10, 4258-4265.

Abidi, et al., "Leveraging XML-based Electronic Medical Records to Extract Experimental Clinical Knowledge: An Automated approach to generate cases for medical case-based reasoning systems", International Journal of Medical Informatics, 68, (2002), 187-203.

Allaire, "Mate Selection by Selection Index Theory", Theor. Appl. Genet., 57, (1980), 267-272.

Ashoor, et al., "Chromosome-Selective Sequencing of Maternal Plasma Cell-Free DNA for First-Trimester Detection of Trisomy 21 and Trisomy 18", American Journal of Obstetrics & Gynecology, 206, (Apr. 2012),322.e1-322.e5.

Ashoor, et al., "Fetal Fraction in Maternal Plasma Cell-Free DNA at 11-13 Weeks' Gestation: Effect of Maternal and Fetal Factors", Fetal Diagnosis Therapy, (May 4, 2012), 1-7.

Bada, et al., "Computational Modeling of Structural Experimental Data", Methods in Enzymology, vol. 317, (2000), 470-491.

Beaumont, et al., "The Bayesian Revolution in Genetics", Nature Reviews Genetics, vol. 5, (Apr. 2004), 251-261.

Beer, et al., "The Biological Basis of Passage of Fetal Cellular Material into the Maternal Circulation", Annals New York Academy of Sciences, 731, (1994), 21-35.

Beerenwinkel, et al., "Geno2pheno: Estimating Phenotypic Drug Resistance from HIV-1 Genotypes", Nucleic Acids Research, vol. 31, No. 13, (2003), 3850-3855.

Beerenwinkel, et al., "Methods for Optimizing Antiviral Combination Therapies", Bioinformatics, vol. 19, Suppl. 1, (2003), i16-i25.

Bisignano, et al., "PGD and Aneuploidy Screening for 24 Chromosomes: Advantages and Disadvantages of Competing Platforms", Reproductive BioMedicine Online, 23, (2011), 677-685.

Bodenreider, "The Unified Medical Language System (UMLS): Integrating Biomedical Terminology", Nucleic Acids Research, vol. 32 (Database issue), (2004), D267-D270.

Breithaupt, "The Future of Medicine", EMBO Reports, vol. 2, No. 61, (2001), 465-467.

Brownie, et al., "The Elimination of Primer-Dimer Accumulation in PCR", Nucleic Acids Research, vol. 25, No. 16, (1997), 3235-3241.

Cairns Paul, "Homozygous Deletions of 9p21 in Primary Human Bladder Tumors Detected by Comparative Multiplex Polymerase Chain Reaction", Cancer Research vol. 54, (1994), 1422-1424.

Caliendo Angela, "Multiplex PCR and Emerging Technologies for the Detection of Respiratory Pathogens", Clinical Infection Diseases vol. 52, Suppl. 4, (2011), S326-S330.

Carnevale, et al., "Attitudes of Mexican Geneticists Towards Prenatal Diagnosis and Selective Abortion", American Journal of Medical Genetics, 75, (1998), 426-431.

Chen, et al., "Noninvasive Prenatal Diagnosis of Fetal Trisomy 18 and Trisomy 13 by Maternal Plasma DNA Sequencing", PLoS ONE, vol. 6, Issue 7, e21791, (Jul. 2011), 7 pgs.

Chiu, et al., "Maternal Plasma DNA Analysis with Massively Parallel Sequencing by Litigation for Noninvasive Prenatal Diagnosis of Trisomy 21", Clinical Chemistry, vol. 56, No. 3, (2010), 459-463.

Chiu, et al., "Non-Invasive Prenatal Assessment of Trisomy 21 by Multiplexed Maternal Plasma DNA Sequencing: Large Scale Validity Study", BMJ, vol. 342, c7401, (2011), 9 pgs.

Chiu, et al., "Non-Invasive Prenatal Diagnosis by Single Molecule Counting Technologies", Trends in Genetics, vol. 25, No. 7, (2009), 324-331.

Chiu, et al., "Noninvasive Prenatal Diagnosis of Fetal Chromosomal Aneuploidy by Massively Parallel Genomic Sequencing of DNA in Maternal Plasma", PNAS, vol. 105, No. 51 (with Supporting Information), (Dec. 23, 2008), 23 pgs.

Chiu, Rossa W.K., "Effects of Blood-Processing Protocols on Fetal and Total DNA Quantification in Maternal Plasma", Clinical Chemistry, 47(9), (Jan. 1, 2001), 1607-1613.

Chu, et al., "A Novel Approach Toward the Challenge of Accurately Quantifying Fetal DNA in Maternal Plasma", Prenatal Diagnosis, 30, (2010), 1226-1229.

Chu, et al., "Statistical Considerations for Digital Approaches to Non-Invasive Fetal Genotyping", Bioinformatics (Advance Access publication), vol. 26, No. 22, (2010), 2863-2866.

Chu, et al., "Statistical Model for Whole Genome Sequencing and its Application to Minimally Invasive Diagnosis of Fetal Genetic Disease", Bioinformatics, vol. 25, No. 10, (2009), 1244-1250.

Cole Neal, "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, vol. 150, (2008), 338-343.

Colella, et al., "QuantiSNP: an Objectives Bayes Hidden-Markov Model to Detect and Accurately Map Copy Number Variation Using SNP Genotyping Data", Nucleic Acids Research, vol. 35, No. 6, (2007), 2013-2025.

Cossu, et al., "Rh D/d Genotyping by Quantitative Polymerase Chain Reaction and Capillary Zone Electrophoresis", Electrophoresis, 17, (1996), 1911-1915.

Coyle, et al., "Standards for Detailed Clinical Models as the Basis for Medical Data Exchange and Decision Support", International Journal of Medical Informatics, 69, (2003), 157-174.

D'Aquila, et al., "Maximizing Sensitivity and Specificity of PCR by Pre-Amplification Heating", Nucleic Acids Research, vol. 19, No. 13, (1991), 3749.

(56) References Cited

OTHER PUBLICATIONS

Daruwala, et al., "A Versatile Statistical Analysis Algorithm to Detect Genome Copy Number Variation", PNAS, vol. 101, No. 46, (Nov. 16, 2004), 16292-16297.
De Vries et al., "Diagnostic genome profiling in mental retardation", Am J Hum Genet, 77, p. 606-616, published online Aug. 30, 2005.
Deangelis, et al., "Solid-phase Reversible Immobilization for the Isolation of PCR Products", Nucleic Acids Research, vol. 23, No. 22, (Nov. 25, 1995), 4742-4743.
Devaney, et al., "Noninvasive Fetal Sex Determination Using Cell-Free Fetal DNA: A Systematic Review and Meta-analysis", JAMA, vol. 306, No. 6, (Aug. 10, 2011), 627-636.
Dhallan, et al., "A Non-Invasive Test for Prenatal Diagnosis Based on Fetal DNA Present in Maternal Blood: A Preliminary Study", Lancet, vol. 369, (Feb. 10, 2007), 474-481.
Dhallan, et al., "Methods to Increase the Percentage of Free Fetal DNA Recovered from the Maternal Circulation", JAMA, vol. 291, No. 9, (Mar. 3, 2004), 1114-1119.
Dieffenbach C, "General Concepts for PCR Primer Design", PCR Methods Appl. vol. 3, (1993), 30-37.
Dolganov, et al., "A Novel Method of Gene Transcript Profiling in Airway Biopsy Homogenates Reveals Increased Expression of a Na +-K+-CL-Contransporter (NKCC1) in Asthmatic Subjects", Genome Res. 2001, vol. 11, (2001),1473-1483.
Donohoe G, et al., "Rapid Single-Tube Screening of the C282Y Hemochromatosis Mutation by Real-Time Multiplex Allele-specific PCR without Fluorescent Probes", Clinical Chemistry, 2000, 46: 1540-1547.
Donoso, et al., "Current Value of Preimplantation Genetic Aneuploidy Screening in IVF", Human Reproduction Update, vol. 13, No. 1, (2007),15-25.
Enrich, et al., "Noninvasive Detection of Fetal Trisomy 21 by Sequencing of DNA in Maternal Blood: A Study in a Clinical Setting", American Journal of Obstetrics & Gynecology, 204, (2011), 205.e1-205.e11.
Eichler, et al., "Mild Course of Fetal Rh D Haemolytic Disease due to Maternal Alloimmunisation to Paternal HLA Class I and II Antigens", Vox Sang, 68, (1995), 243-247.
Ellonen, et al., "Development of SNP Microarray for Supplementary Paternity Testing", International Congress Series, vol. 1261, (2004), 12-14.
European Application No. 06838311.6, Communication and Extended European Search Report mailed Dec. 30, 2008, 8 pgs.
European Application No. 08742125.1, Communication pursuant to Article 94(3) EPC and Examination Report mailed Feb. 12, 2010, 5 pgs.
Fan, et al., "Non-Invasive Prenatal Measurement of the Fetal Genome", Nature, doi: 10.1038/nature11251 (with Supplemental Information), (2012), 26 pgs.
Fan, "Highly Parallel Genomic Assay", Nature Reviews, vol. 7, Aug. 2006, 632-644.
Fazio, et al., "Identification of Rapd Markers Linked to Fusarium Crown and Root Rot Resistance (Frl) in Tomato", Euphytica 105, (Mar. 1, 1999), 205-210.
Finishing the Euchromatic Sequence of the Human Genome, Nature vol. 431, (Oct. 21, 2004), 931-945.
Fiorentino, et al., "Development and Clinical Application of a Strategy for Preimplantation Genetic Diagnosis of Single Gene Disorders Combined with HLA Matching", Molecular Human Reproduction (Advance Access publication), vol. 10, No. 6, (2004), 445-460.
Fiorentino, et al., "Short Tandem Repeats Haplotyping of the HLA Region in Preimplantation HLA Matching", European Journal of Human Genetics, 13, (2005), 953-958.
Fiorentino, et al., "Strategies and Clinical Outcome of 250 Cycles of Preimplantation Genetic Diagnosis for Single Gene Disorders", Human Reproduction, vol. 21, No. 3, (2006), 670-684.
Fixed Medium, dictionary definition, Academic Press Dictionary of Science and Technology [retrieved on Nov. 18, 2009]. Retrieved from the Internet: <URL: www.credoreference.com/entry/apdst/fixed_medium>, (1996),1 pg.
Forejt et al., "Segmental trisomy of mouse chromosome 17: introducing an alternative model of Down's syndrome", Genomics, 4(6), p. 647-652, 2003 (2003).
Freeman, et al., "Copy Number Variation: New Insights in Genome Diversity", Genome Research, 16, (2006), 949-961.
Frost Mackenzie, "Differential Effects of Chronic Pulsatile Versus Chronic Constant Maternal Hyperglycemia on Fetal Pancreatic B-Cells", Journal of Pregnancy, vol. 2012, Article ID 812094, 8 pgs.
Ganshirt-Ahlert, et al., "Fetal DNA in Uterine Vein Blood", Obstetrics & Gynecology, 80, (1992), 601-603.
Ganshirt-Ahlert, et al., "Ratio of Fetal to Maternal DNA is Less Than 1 in 5000 at different Gestational Ages in Maternal Blood", Clinical Genetics, 38, (1990), 38-43.
Ganshirt-Ahlert, et al., "Three Cases of 45,X/46,XYnf Mosaicism", Human Genetics, 76, (1987), 153-156.
Gardina, et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, vol. 9, No. 489 (doi:10.1186/1471-2164-9-489), (2008), 16 pgs.
Genetics Home Reference, http://ghr.nlm.nih.gov/handbook/genomicresearch/snp, (Feb. 28, 2014), 1-2.
Ghanta, et al., "Non-Invasive Prenatal Detection of Trisomy 21 Using Tandem Single Nucleotide Polymorphisms", PLoS ONE, vol. 5, Issue 10, e13184, (Oct. 2010), 10 pgs.
Gjertson, et al., "Assessing Probability of Paternity and the Product Rule in DNA Systems", Genetica, 96, (1995), 89-98.
Greenwalt, et al., "The Quantification of Fetomaternal Hemorrhage by an Enzyme-Linked Antibody Test with Glutaraldehyde Fixation", Vox Sang, 63, (1992), 268-271.
Guetta, et al., "Analysis of Fetal Blood Cells in the Maternal Circulation: Challenges, Ongoing Efforts, and Potential Solutions", Stem Cells and Development, 13, (2004), 93-99.
Hara, et al., "Subtractive cDNA Cloning Using Oligo(dT)30-latex and PCR: Isolation of cDNA Clones Specific to Undifferentiated Human Embryonal Carcinoma Cells", Nucleic Acids Research, vol. 19, No. 25, (1991), 7097-7104.
Hardenbol, et al., "Multiplexed Genotyping With Sequence-Tagged Molecular Inversion Probes", Nature Biotechnology vol. 21, No. 6, (Jun. 2003), 673-678.
Hardenbol, et al., "Highly multiplexed molecular inversion probe genotyping: Over 10,000 targeted SNP's genotyped in a singled tube assay", Genome Research, 15, (Jan. 1, 2005), 269-275.
Harper, et al., "Recent Advances and Future Developments in PGD", Prenatal Diagnosis, 19, (1999), 1193-1199.
Harton, et al., "Preimplantation Genetic Testing for Marfan Syndrome", Molecular Human Reproduction, vol. 2, No. 9, (1996), 713-715.
Hellani, et al., "Clinical Application of Multiple Displacement Amplification in Preimplantation Genetic Diagnosis", Reproductive BioMedicine Online, vol. 10, No. 3, (2005), 376-380.
Hojsgaard, et al., "BIFROST—Block Recursive Models Induced from Relevant Knowledge, Observations, and Statistical Techniques", Computational Statistics & Data Analysis, 19, (1995), 155-175.
Hollox, et al., "Extensive Normal Copy Number Variation of a β-Defensin Antimicrobial-Gene Cluster", Am. J. Hum. Genet., 73, (2003), 591-600.
Homer, et al., "Resolving Individuals Contributing Trace Amounts of DNA to Highly Complex Mixtures Using High-Density SNP Genotyping Microarrays", PLOS Genetics, vol. 4, Issue 8, e1000167, (Aug. 2008), 9 pgs.
Hoogendoorn Bastiaan, "Genotyping Single Nucleotide Polymorphisms by Primer Extension and High Performance Liquid Chromatography", Hum Genet vol. 104, (1999), 89-93.
How Many Carbs in a Potato?, [Online]. Retrieved from the Internet :<http://www.healthguide.org/How-Many-Carbs-In-A-Potato.html>, (Nov. 1, 2014), 3 pgs.

(56) References Cited

OTHER PUBLICATIONS

Hu, et al., "Aneuploidy Detection in Single Cells Using DNA Array-Based Comparative Genomic Hybridization", Molecular Human Reproduction, vol. 10, No. 4, (2004), 283-289.
Ido, Yasuo, "Hyperglycemia-Induced Apoptosis in Human Umbilical Vein Endothelial Cells: Inhibition by the AMP-Activated Protein Kinase Activation", Diabetes, vol. 51, Jan. 2002, 159-167.
International Application No. PCT/US2006/045281, International Preliminary Report on Patentability mailed May 27, 2008, 1 pg.
International Application No. PCT/US2006/045281, International Search Report and Written Opinion mailed Sep. 28, 2007, 7 pgs.
International Application No. PCT/US2008/003547, International Search Report mailed Apr. 15, 2009, 5 pgs.
International Application No. PCT/US2009/034506, International Search Report mailed Jul. 8, 2009, 2 pgs.
International Application No. PCT/US2009/045335, International Search Report mailed Jul. 27, 2009, 1 pg.
International Application No. PCT/US2009/052730, International Search Report mailed Sep. 28, 2009, 1 pg.
International Application No. PCT/US2010/050824, International Search Report mailed Nov. 15, 2010, 2 pgs.
International Application No. PCT/US2011/037018, International Search Report mailed Sep. 27, 2011, 2 pgs.
International Application No. PCT/US2011/061506, International Search Report mailed Mar. 16, 2012, 1 pg.
International Application No. PCT/US2011/066938, International Search Report mailed Jun. 20, 2012, 1 pg.
International Application No. PCT/US2012066339, International Search Report mailed Mar. 5, 2013, 1 pg.
International Application No. PCT/US2013/57924, International Search Report and Written Opinion mailed Feb. 18, 2014, 8 pgs.
Kazakov, et al., "Extracellular DNA in the Blood of Pregnant Women", Tsitologia, vol. 37, No. 3, (1995), 8 pgs.
Kijak, et al., "Discrepant Results in the Interpretation of HIV-1 Drug-Resistance Genotypic Data Among Widely Used Algorithms", HIV Medicine, 4, (2003), 72-78.
Kuliev, et al., "Thirteen Years' Experience on Preimplantation Diagnosis: Report of the Fifth International Symposium on Preimplantation Genetics", Reproductive BioMedicine Online, vol. 8, No. 2, (2004), 229-235.
Lambert-Messerlian, et al., "Adjustment of Serum Markers in First Trimester Screening", Journal of Medical Screening, vol. 16, No. 2, (2009), 102-103.
Li, et al., "Non-Invasive Prenatal Diagnosis Using Cell-Free Fetal DNA in Maternal Plasma from PGD Pregnancies", Reproductive BioMedicine Online, vol. 19, No. 5, (2009), 714-720.
Liao, et al., "Targeted Massively Parallel Sequencing of Maternal Plasma DNA Permits Efficient and Unbiased Detection of Fetal Alleles", Clinical Chemistry, vol. 57, No. 1, (2011), 92-101.
Liew et al. (Clinical Chemistry, 2004, 50(7), 1156-1164.
Lindroos, et al., "Genotyping SNPs by Minisequencing Primer Extension Using Oligonucleotide Microarrays", Methods in Molecular Biology, vol. 212—Single Nucleotide Polymorphisms: Methods and Protocols, P-K Kwok (ed.), Humana Press, Inc., Totowa, NJ, (2003), 149-165.
Lo, et al., "Detection of Fetal RhD Sequence from Peripheral Blood of Sensitized RhD-Negative Pregnant Women", British Journal of Haematology, 87, (1994), 658-660.
Lo, et al., "Detection of Single-Copy Fetal DNA Sequence from Maternal Blood", The Lancet, vol. 335, (Jun. 16, 1990), 1463-1464.
Lo, et al., "Digital PCR for the Molecular Detection of Fetal Chromosomal Aneuploidy", PNAS, vol. 104, No. 32, (Aug. 7, 2007), 13116-13121.
Lo, et al., "Free Fetal DNA in Maternal Circulation", JAMA, vol. 292, No. 23 (Letters to the Editor), (Dec. 15, 2004), 2835-2836.
Lo, et al., "Maternal Plasma DNA Sequencing Reveals the Genome-Wide Genetic and Mutational Profile of the Fetus", Science Translational Medicine, vol. 2, Issue 61, (Dec. 8, 2010), 13 pgs.
Lo, et al., "Plasma Placental RNA Allelic Ratio Permits Noninvasive Prenatal Chromosomal Aneuploidy Detection", Nature Medicine, vol. 13, No. 2, (Feb. 2007), 218-223.
Lo, et al., "Prenatal Determination of Fetal RhD Status by Analysis of Peripheral Blood of Rhesus Negative Mothers", The Lancet, vol. 341, (Letters to the Editor), (May 1, 1993), 1147-1148.
Lo, et al., "Prenatal Determination of Fetal Rhesus D Status by DNA Amplification of Peripheral Blood of Rhesus-Negative Mothers", Annals New York Academy of Sciences, 731, (Sep. 7, 1994), 229-236.
Lo, et al., "Prenatal Sex Determination by DNA Amplification from Maternal Peripheral Blood", The Lancet, vol. 2, No. 8676, (Dec. 9, 1989), 1363-1365.
Lo, et al., "Rapid Clearance of Fetal DNA from Maternal Plasma", Am. J. Hum. Genet., 64, (1999), 218-224.
Lo, et al., "Strategies for the Detection of Autosomal Fetal DNA Sequence from Maternal Peripheral Blood", Annals New York Academy of Sciences, 731, (1994), 204-213.
Lo, "Fetal Nucleic Acids in Maternal Plasma: Toward the Development of Noninvasive Prenatal Diagnosis of Fetal Chromosomal Aneuploidies", Ann. N.Y. Acad. Sci., 1137, (2008), 140-143.
Lun, et al., "Noninvasive Prenatal Diagnosis of Monogenic Diseases by Digital Size Selection and Relative Mutation Dosage on DNA in Maternal Plasma", PNAS, vol. 105, No. 50, (Dec. 16, 2008), 19920-19925.
Maniatis, et al., In: Molecular Cloning: A Laboratory Manual, Cold Spring Harbor Laboratory, New York, Thirteenth Printing, (Sep. 1986), 458-459.
Mansfield, "Diagnosis of Down Syndrome and Other Aneuploidies Using Quantitative Polymerase Chain Reaction and Small Tandem Repeat Polymorphisms", Human Molecular Genetics, vol. 2, No. 1, (1993), 43-50.
May, "How Many Species Are There on Earth?", Science vol. 241, (Sep. 16, 1988), 1441-1449.
McCray, et al., "Aggregating UMLS Semantic Types for Reducing Conceptual Complexity", MEDINFO 2001: Proceedings of the 10th World Congress on Medical Informatics (Studies in Health Technology and Informatics, 84), V. Patel et al. (eds.), IOS Press, Amsterdam, (2001), 216-220.
Miller Robert, "Homocysteine-Induced Changes in Brain Membrane Composition Correlate with Increased Brain Caspase-3 Activities and Reduced Chick Embryo Viability", Comparative Biochemistry and Physiology, Part B, vol. 136 (2003), 521-532.
Miller Robert, "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, vol. 141 (2005), 323-330.
Multiplexing with RainDrop Digital PCR, RainDance Technologies Application Note, (2013), 1-2.
Munne, et al., "Chromosome Abnormalities in Human Embryos", Textbook of Assisted Reproductive Techniques, (2004), 355-377.
Myers, et al., "Accurate Detection of Aneuploidies in Array CGH and Gene Expression Microarray Data", Bioinformatics, vol. 20, No. 18, (2004), 3533-3543.
Nannya, et al., "A Robust Algorithm for Copy Number Detection Using High-density Oligonucleotide Single Nucleotide Polymorphism Genotyping Arrays", Cancer Res., 65, (Jul. 15, 2005), 6071-6079.
Nucleic Acids, Linkers and Primers: Random Primers, New England BioLabs 1998/99 Catalog, (1998), 121 and 284.
Ogino, et al., "Bayesian Analysis and Risk Assessment in Genetic Counseling and Testing", Journal of Molecular Diagnostics, vol. 6, No. 1, (Feb. 2004), 9 pgs.
Orozco, et al., "Placental Release of Distinct DNA-Associated Micro-Particles into Maternal Circulation: Reflective of Gestation Time and Preeclampsia", Placenta, 30, (2009), 891-897.
Ozawa, et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report (including text in Japanese), (1994), 8 pgs.
Page, et al., "Chromosome Choreography: The Meiotic Ballet", Science, vol. 301, (Aug. 8, 2003), 785-789.

(56) References Cited

OTHER PUBLICATIONS

Palomaki, et al., "DNA Sequencing of Maternal Plasma Reliably Identifies Trisomy 18 and Trisomy 13 as Well as Down Syndrome: an International Collaborative Study", Genetics in Medicine, (2012), 10 pgs.
Papageorgiou, et al., "Fetal-Specific DNA Methylation Ratio Permits Noninvasive Prenatal Diagnosis of Trisomy 21", Nature Medicine (advance online publication), 17, (Mar. 6, 2011), 5 pgs.
Pena, et al., "Paternity Testing in the DNA Era", Trends in Genetics, vol. 10, No. 6, (Jun. 1994), 204-209.
Perkel Jeffrey, "Overcoming the Challenges of Multiplex PCR", Biocompare Editorial Article, Oct. 23, 2012, 1-5.
Perry, et al., "The Fine-Scale and Complex Architecture of Human Copy-Number Variation", The American Journal of Human Genetics, 82, (Mar. 2008), 685-695.
Peters, et al., "Noninvasive Prenatal Diagnosis of a Fetal Microdeletion Syndrome", New England Journal of Medicine, vol. 365, No. 19, (Nov. 10, 2011), 1847-1848.
Pfaffl, "Relative Expression Software Tool (REST © ) for Group-Wise Comparison and Statistical Analysis of Relative Expression Results in real-Time PCR", Nucleic Acids Research, vol. 30, No. 9, e36, (2002), 10 pgs.
Phillips, et al., "Resolving Relationship Tests that Show Ambiguous STR Results Using Autosomal SNPs as Supplementary Markers", Forensic Science International: Genetics 2, (2008), 198-204.
Podder et al. (BMC Med Genom, 2008, vol. 1, No. 5, p. 1 of 15).
Porreca, et al., "Multiplex Amplification of Large Sets of Human Exons", Nature Methods (advance online publication), 4, (Oct. 14, 2007), 6 pgs.
Rabinowitz, et al., "Accurate Prediction of HIV-1 Drug Response from the Reverse Transcriptase and Protease Amino Acid Sequences Using Sparse Models Created by Convex Optimization", Bioinformatics, vol. 22, No. 5, (2006), 541-549.
Rahmann, et al., "Mean and Variance of the Gibbs Free Energy of Oligonucleotides in the Nearest neighbor Model Under Varying Conditions", Bioinformatics, vol. 20, No. 17, (2004), 2928-2933.
Rechitsky, et al., "Preimplantation Genetic Diagnosis with HLA Matching", Reproductive BioMedicine Online, vol. 9, No. 2, (2004), 210-221.
Ricciotti Hope, "Eating by Trimester", [Online]. Retrieved from Internet :< http://www.youandyourfamily.com/article.php?story=Eating+by+Trimester>, (Oct. 7, 2014), 3 pgs.
Roper, et al., "Forensic Aspects of DNA-Based Human Identity Testing", Journal of Forensic Nursing, 4, (2008), 150-156.
Roux K, "Optimization and Troubleshooting in PCR", PCR Methods Appl. vol. 4, (1995), 185-194.
Rozen, et al., "Primer3 on the WWW for General Users and for Biologist Programmers", Methods in Molecular Biology, vol. 132: Bioinformatics Methods and Protocols, (1999), 365-386.
Russell, et al., "X Chromosome Loss and Ageing", Cytogenet Genome Res, vol. 116, (2007), 181-185.
Sander, et al., "Genetic Medicine and the Future of Health Care", Science, vol. 287, (3/17/200), 1977-1978.
Schoumans et al., "Detection of chromosomal imbalances in children with idiopathic mental retardation by array based comparative genomic hybridisation (array-CGH)", JMed Genet, 42, p. 699-705, Sep. 2005.
Sebat, et al., "Strong Association of De Novo Copy Number Mutations with Autism", Science, vol. 316, (Apr. 20, 2007), 445-449.
Sehnert, et al., "Optimal Detection of Fetal Chromosomal Abnormalities by Massively Parallel DNA Sequencing of Cell-Free Fetal DNA from Maternal Blood", Clinical Chemistry (papers in press), vol. 57, No. 7, (2011), 8 pgs.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, (2004), 241-248.
Simpson, et al., "Fetal Cells in Maternal Blood: Overview and Historical Perspective", Annals New York Academy of Sciences, 731, (1994), 1-8.
Sint Daniela, "Advances in Multiplex PCR: Balancing Primer Efficiencies and Improving Detection Success", Methods in Ecology and Evolution vol. 3, (2012), 898-905.
Slater, et al., "High-Resolution Identification of Chromosomal Abnormalities Using Oligonucleotide Arrays Containing 116,204 SNPs", Am. J. Hum. Genet., vol. 77, No. 5, (2005), 709-726.
Snijders, et al., "Assembly of Microarrays for Genome-Wide Measurement of DNA Copy Number", Nature Genetics vol. 29, (Nov. 2001), 263-264.
Sparks, et al., "Selective Analysis of Cell-Free DNA in Maternal Blood for Evaluation of Fetal Trisomy", Prenatal Diagnosis, 32, (2012), 1-7.
Sparks, et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology, 206, (Apr. 2012), 319.e1-319.e9.
Spiro Alexander, "A Bead-Based Method for Multiplexed Identification and Quantitation of DNA Sequences Using Flow Cytometry", Applied and Environmental Microbiology, Oct. 2000, vol. 66, No. 10, 4258-4265.
Stephens, et al., "A Comparison of Bayesian Methods for Haplotype Reconstruction from Population Genotype Data", Am. J. Hum. Genet., 73, (2003),1162-1169.
Stevens, et al., "Ontology-Based Knowledge Representation for Bioinformatics", Briefings in Bioinformatics, vol. 1, No. 4, (Nov. 2000), 398-414.
Steyerberg, et al., "Application of Shrinkage Techniques in Logistic Regression Analysis: A Case Study", Statistica Neerlandica, vol. 55, No. 1, (2001), 76-88.
Strom, et al., "Neonatal Outcome of Preimplantation Genetic Diagnosis by Polar Body Removal: The First 109 Infants", Pediatrics, vol. 106, No. 4, (Oct. 4, 2000), 650-653.
Stroun, et al., "Prehistory of the Notion of Circulating Nucleic Acids in Plasma/Serum (CNAPS): Birth of a Hypothesis", Ann. N.Y. Acad. Sci., 1075, (2006), 10-20.
Sweetkind-Singer, et al., "Log-Penalized Linear Regression", International Symposium on Information Theory, Yokahama, Japan, (Jun. 29, 2013-Jul. 4, 2003), p. 286.
Tang, et al., "Detection of Fetal-Derived Paternally Inherited X-Chromosome Polymorphisms in Maternal Plasma", Clinical Chemistry vol. 45, No. 11, (1999), 2033-2035.
Thomas, et al., "The Time of Appearance and Disappearance of Fetal DNA from the Maternal Circulation", Prenatal Diagnosis, vol. 15, (1995), 641-646.
Tong, et al., "Noninvasive Prenatal Detection of Trisomy 21 by an Epigenetic-Genetic Chromosome-Dosage Approach", Clinical Chemistry, vol. 56, No. 1, (2010), 90-98.
Tong, "Noninvasive Prenatal Detection of Fetal Trisomy 18 by Epigenetic Allelic Ratio Analysis in Maternal Plasma: Theoretical and Empirical Considerations", Clinical Chemistry vol. 52, No. 12, (2006), 2194-2202.
Troyanskaya, et al., "A Bayesian Framework for Combining Heterogeneous Data Sources for Gene Function Prediction (in *Saccharomyces cerevisiae*)", PNAS, vol. 100, No. 14, (Jul. 8, 2003), 8348-8353.
Tsui, et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, (2009), 1031-1037.
Turner, et al., "Massively Parallel Exon Capture and Library-Free Resequencing Across 16 Genomes", Nature Methods, vol. 6, No. 5, (May 2009), 315-316.
U.S. Appl. No. 11/004,274, Office Action mailed Nov. 24, 2009, 31 pgs.
U.S. Appl. No. 11/004,274, Office Action mailed Feb. 4, 2009, 26 pgs.
U.S. Appl. No. 11/004,274, Office Action mailed Mar. 2, 2011, 50 pgs.
U.S. Appl. No. 11/004,274, Office Action mailed May 13, 2008, 25 pgs.

(56) References Cited

OTHER PUBLICATIONS

U.S. Appl. No. 11/496,982, Office Action mailed Jan. 21, 2011, 25 pgs.
U.S. Appl. No. 11/496,982, Office Action mailed May 27, 2010, 8 pgs.
U.S. Appl. No. 11/603,406, Office Action mailed Feb. 18, 2011, 26 pgs.
U.S. Appl. No. 11/603,406, Office Action mailed Mar. 14, 2013, 15 pgs.
U.S. Appl. No. 11/603,406, Office Action mailed Aug. 19, 2010, 20 pgs.
U.S. Appl. No. 11/634,550, Office Action mailed Jan. 24, 2011, 13 pgs.
U.S. Appl. No. 11/634,550, Office Action mailed Aug. 4, 2010, 7 pgs.
U.S. Appl. No. 12/076,348, Office Action mailed Feb. 8, 2013, 9 pgs.
U.S. Appl. No. 12/076,348, Office Action mailed Mar. 4, 2011, 26 pgs.
U.S. Appl. No. 12/076,348, Office Action mailed Aug. 20, 2010, 22 pgs.
U.S. Appl. No. 13/683,604, Office Action mailed Nov. 22, 2013, 81pages.
Vallone, et al., "AutoDimer: a Screening Tool for Primer-Dimer and Hairpin Structures", BioTechniques vol. 37, (Aug. 2004), 226-231.
Verlinsky, et al., "Over a Decade of Experience with Preimplantation Genetic Diagnosis", Fertility and Sterility, vol. 82, No. 2, (Aug. 2004), 302-303.
Wagner, et al., "Non-Invasive Prenatal Paternity Testing from Maternal Blood", Int. J. Legal Med., 123, (2009), 75-79.
Wagner, Jasenka et al. "Non-invasive prenatal paternity testing from maternal blood", International Journal of Legal Medicine, Springer, Berlin, DE, vol. 123, No. 1, Oct. 24, 2008, pp. 75-79.
Wang, et al., "A Genotyping System Capable of Simultaneously Analyzing >1000 Single Nucleotide Polymorphisms in a Haploid Genome", Genome Res., vol. 15, 2005, 276-283.
Wang, Yuker et al., "Allele quantification using molecular inversion probes (MIP)", Nucleic Acids Research, vol. 33, No. 21 , (Nov. 28, 2005), 1-14.
Wells, "Advances in Preimplantation Genetic Diagnosis", European Journal of Obstetrics and Gynecology and Reproductive Biology, 115S, (2004), S97-S101.
Wells Dagan, "Detailed Chromosomal and Molecular Genetic Analysis of Single Cells by Whole Genome Amplification and Comparative Genomic Hybridisation", Nucleic Acids Research, 1999, vol. 27, No. 4, 1214-1218.
Wells, "Microarray for Analysis and Diagnosis of Human Embryos", 12th International Congress on Prenatal Diagnosis and Therapy, Budapest, Hungary, (Jun. 24-27, 2004), 9-17.
Wen Daxing, "Universal Multiples PCR: A Novel Method of Simultaneous Amplification of Multiple DNA Fragments", Plant Methods vol. 8, No. 32, (2012), 1-9.
Wilton, et al., "Birth of a Healthy Infant After Preimplantation Confirmation of Euploidy by Comparative Genomic Hybridization", N. Engl. J. Med., vol. 345, No. 21, (Nov. 22, 2001), 1537-1541.
Wilton, "Preimplantation Genetic Diagnosis and Chromosome Analysis of Blastomeres Using Comparative Genomic Hybridization", Human Reproduction Update, vol. 11, No. 1, (2005), 33-41.
Yeh, et al., "Knowledge Acquisition, Consistency Checking and Concurrency Control for Gene Ontology (GO)", Bioinformatics, vol. 19, No. 2, (2003), 241-248.
Zhang Rui, "Quantifying RNA Allelic Ratios by Microfluidic Multiplex PCR and Sequencing", Nature Methods, vol. 11, No. 1, Jan. 2014, 51-56.
European Application No. 014198110, European Search Report Mailed Apr. 28, 2015, 3 pages.
"Blast of AAAAAAAAATTTAAAAAAAAATTT(http://blast.ncbi.nlm.nih.gov/Blast.cgi, downloaded May 4, 2015)", May 4, 2015.
"db SNP rs2056688 (http://www.ncbi.nlm.nih.gov/projects/SNP/snp_ref.cgi?rs=2056688, downloaded May 4, 2015", 2015.
"Declaration by Dr. Zimmerman of Oct. 30, 2014 filed in U.S. Appl. No. 14/044,434", Oct. 30, 2014.
"Merriam-Webster.com (http://vvww.merriam-webster.com/dictionary/universal, downloaded Jul. 23, 2014)", Jul. 23, 2014.
"www.fatsecret.com (printed from internet Nov. 1, 2014)", Nov. 1, 2014.
Bentley, David R et al., "Accurate Whole Human Genome Sequencing Using Reversible Terminator Chemistry", Nature, 456, 6, 2008, 53-59.
Bianchi, D W. et al., "Fetal gender and aneuploidy detection using fetal cells maternal blood: analysis of NIFTY I data", Prenat Diagn 2002; 22, 2002, 609-615.
Cross, Jillian et al., "Resolution of trisomic mosaicism in prenatal diagnosis: estimated performance of a 50K SNP microarray", Prenat Diagn 2007; 27, 2007, 1197-1204.
Ding, C et al., "Direct molecular haplotyping of long-range genomic DNA with M1-PCR", PNAS 100(13), 2003, 7449-7453.
Fan, et al., "Whole-genome molecular haplotyping of single cells", Nature Biotechnology, vol. 29, No. 1, Jan. 1, 2011, 51-57.
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Harismendy, O et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Howie, et al., "Fast and accurate genotype imputation in genome-wide association studies through pre-phasing", Nature Genetics, voi. 44, No. 8, Jul. 22, 2012, 955-959.
Lllumina Catalog, "Paired-End Sample Preparation Guide, Illumina Catalog# PE-930-1 001, Part# 1005063 Rev. E", 2011, 1-40.
PCT/US2014/051926 International Search Report mailed, Dec. 9, 2014, 3 pgs.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005, pp. 3455-3464.
Ryan, et al., "The importance of phase information for human genomics", Nature Reviews Genetics, voi. 12, No. 3, Mar. 1, 2011.
Rychlik, et al., "Optimization of the annealing temperature for DNA amplification in vitro", Nucleic Acids Research, 18(21), 1990, 6409-6412.
Su, S.Y. et al., ""Inferring combined CNV/SNP haplotypes from genotype data"", Bioinformatics, vol. 26, No. 11,1, Jun. 1, 2010, 1437-1445.
Sun, Guihua et al., "SNPs in human miRNA genes affect biogenesis and function", RNA, 15(9), 2009, 1640-1651.
Varley, Katherine Elena et al., "Nested Patch PCR Enables Highly Multiplexed Mutation Discovery in Candidate Genes", Genome Res., 18(11), 2008, 1844-1850.
"Guideline related to genetic examination", Societies Related to Genetic Medicine, Japanese Society for Genetic Counseling, Japanese Society for Gene Diagnosis and Therapy, Japan Society of Obstetrics an, 2003, 2-15.
Aoki, Yasuhiro , "Statistical and Probabilistic Bases of Forensic DNA Testing", The Journal of the Iwate Medical Association, 2002, vol. 54, p. 81-94.
Ellison, Aaron M. , "Bayesian Inference in Ecology", Ecology Letters, 2004, vol. 7, p. 509-520.
Fredriksson, et al., "Multiplex amplification of all coding sequences within 10 cancer genes by Gene-Collector", Nucleic Acids Research, 2007, vol. 35, No. 7 e47, 1-6.
Holleley, et al., "Multiplex Manager 1.0: a Cross-Platform Computer Program that Plans and Optimizes Multiplex PCR", BioTechniques46:511-517 (Jun. 2009), 511-517.
Hospital, F et al., "A General Algorithm to Compute Multilocus Genotype Frequencies Under Various Mating Systems" vol. 12, No. 6, Jan. 1, 1996, pp. 455-462.

(56) References Cited

OTHER PUBLICATIONS

Krjutskov, K et al., "Development of a single tube 640-plex genotyping method for detection of nucleic acid variations on microarrays", Nucleic Acids Research, vol. 36, No. 12, May 23, 2008, pp. e75-e75.
Markoulatos, P et al., "Multiplex Polymerase Chain Reaction: A Practical Approach", 2002 Wiley-Liss, Inc. DOI 10.1002/jcla.2058 Journal of Clinical Laboratory Analysis 16:47-51 (2002).
Muse, Spencer V. , "Examining rates and patterns of nucleotide substitution in plants", Plant Molecular Biology 42: 25-43, 2000.
Sasabe, Yutaka, "Genetic Diagnosis of Gametes and Embryos Resulting from ART", Japanese Journal of Fertility and Sterility, 2001, vol. 46, No. 1, p. 43-46.
Servin, B et al., "MOM: A Program to Compute Fully Informative Genotype Frequencies in Complex Breeding Schemes", Journal of Heredity, vol. 93, No. 3, Jan. 1, 2002, pp. 227-228.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011, pp. 6549-6554.
Shen, Zhiyong, "MPprimer: a program for reliable multiplex PCR primer design", BMC Bioinformatics 2010, 11:143, 1-7.
Tamura, et al., "Sibling Incest and formulation of paternity probability: case report", Legal Medicine, 2000, vol. 2, p. 189-196.
Tang, et al., Multiplex fluorescent PCR for noninvasive prenatal detection of fetal-derived paternally inherited diseases using circulatory fetal DNA in materna plasma, Eur J Obstet Gynecol Reprod Biol, 2009, v.144, No. 1, p. 35-39.
You, Frank M. et al., "BatchPrimer3: A high throughput web application for PCR and sequencing primer design", BMC Bioinformatics, Biomed Central, London, GB, vol. 9, No. 1, May 29, 2008, p. 253.
Merriam-Webster (attached, available at http://www.merriam-webster.com/medical/stimulant, accessed Mar. 14, 2016).
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).
The Bump (Panorama Test, attached, Jul. 1, 2013).
What to Expect (Weird Harmony results, attached, May 1, 2015).
Wikipedia (attached, available at https://en.wikipedia.org/wiki/Stimulant, accessed Mar. 14, 2016).
Hall, M., "Panorama Non-Invasive Prenatal Screening for Microdeletion Syndromes", Apr. 1, 2014, XP055157224, Retrieved from the Internet: URL:http://www.panoramatest.com/sites/default/files/files/PanoramaMicrodeletionsWhite Paper-2.pdf [retrieved on Dec. 8, 2014].
Bevinetto, Gina (5 Foods All Pregnant Women Need, American Baby, available at http://www.parents.com/pregnancy/mybody/nutrition/5greatpregnancyfoods/, Apr. 15, 2008).
Echeverri, et al., "Caffeine's Vascular Mechanisms of Action", International Journal of Vascular Medicine vol. 2010(2010), 10 pages, Aug. 25, 2010.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Hayden, et al., "Multiplex-Ready PCR: A new method for multiplexed SSR and SNP genotyping", BMC Genomics 2008, 9(80), 1-12.
Ishii, et al., "Optimization of Annealing Temperature to Reduce Bias Caused by a Primer Mismatch in Multitemplate PCR", Applied and Environmental Microbiology, Aug. 2001, p. 3753-3755.
Liao, J. et al., "An Alternative Linker-Mediated Polymerase Chain Reaction Method Using a Dideoxynucleotide to Reduce Amplification Background", Analytical Biochemistry 253, 137-139 (1997).
Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.
Nygren, et al., "Quantification of Fetal DNA by Use of Methylation-Based DNA Discrimination", Clinical Chemistry 56:10 1627-1635 (2010).
O'Malley, R et al., "An adapter ligation-mediated PCR method for high-throughput mapping of T-DNA inserts in the Arabidopsis genome", Nat. Protoc. 2, 2910-2917 (2007).
Srinivasan, et al., "Noninvasive Detection of Fetal Subchromosome Abnormalities via Deep Sequencing of Maternal Plasma", The American Journal of Human Genetics 92, 167-176, Feb. 7, 2013.
U.S. Appl. No. 13/793,133, filed Mar. 11, 2013, System and Method for Cleaning Noisy Genetic Data from Target Individuals Using Genetic Data from Genetically Related Individuals.
U.S. Appl. No. 13/793,186, filed Mar. 11, 2013, System and Method for Cleaning Noisy Genetic Data from Target Individuals Using Genetic Data from Genetically Related Individuals.
U.S. Appl. No. 13/949,212, filed Jul. 23, 2013, System and Method for Cleaning Noisy Genetic Data and Determining Chromosome Copy Number.
U.S. Appl. No. 14/092,457, filed Nov. 27, 2013, System and Method for Cleaning Noisy Genetic Data from Target Individuals Using Genetic Data from Genetically Related Individuals.
U.S. Appl. No. 14/156,433, filed Jan. 14, 2014, System and Method for Cleaning Noisy Genetic Data from Target Individuals Using Genetic Data from Genetically Related Individuals.
U.S. Appl. No. 14/286,895, filed May 23, 2014, System and Method for Cleaning Noisy Genetic Data from Target Individuals Using Genetic Data from Genetically Related Individuals.
U.S. Appl. No. 12/918,445, filed Oct. 7, 2010, Methods for Cell Genotyping.
U.S. Appl. No. 12/994,260, filed Dec. 20, 2010, Methods for Embryo Characterization and Comparison.
U.S. Appl. No. 13/057,350, filed Mar. 29, 2011, Methods for Allele Calling and Ploidy Calling.
U.S. Appl. No. 13/846,111, filed Mar. 18, 2013, Methods for Allele Calling and Ploidy Calling.
U.S. Appl. No. 13/110,685, filed May 18, 2011, Methods for Non-Invasive Prenatal Ploidy Calling.
U.S. Appl. No. 13/300,235, filed Nov. 18, 2011, Methods for Non-Invasive Prenatal Ploidy Calling.
U.S. Appl. No. 13/335,043, filed Dec. 22, 2011, Methods for Non-Invasive Prenatal Paternity Testing.
U.S. Appl. No. 13/499,086, filed Mar. 29, 2012, Methods for Non-Invasive Prenatal Ploidy Calling.
U.S. Appl. No. 13/683,604, filed Nov. 21, 2012, Highly Multiplex PCR Methods and Compositions.
U.S. Appl. No. 13/780,022, filed Feb. 28, 2013, Informatics Enhanced Analysis of Fetal Samples Subject to Maternal Contamination.
U.S. Appl. No. 13/791,397, filed Mar. 8, 2013, Methods for Non-Invasive Prenatal Ploidy Calling.
U.S. Appl. No. 13/846,160, filed Mar. 18, 2013, Methods for Non-Invasive Prenatal Paternity Testing.
U.S. Appl. No. 13/896,293, filed May 16, 2013, Methods for Non-Invasive Prenatal Ploidy Calling.
U.S. Appl. No. 13/968,302, filed Aug. 15, 2013, Methods and Compositions for Reducing Genetic Library Contamination.
U.S. Appl. No. 14/044,434, filed Oct. 2, 2013, Highly Multiplex PCR Methods and Compositions.
U.S. Appl. No. 14/080,656, filed Nov. 14, 2013, Methods for Non-Invasive Prenatal Ploidy Calling.
U.S. Appl. No. 14/100,928, filed Dec. 9, 2013, Methods for Non-Invasive Prenatal Ploidy Calling.
U.S. Appl. No. 14/171,587, filed Feb. 3, 2014, Highly Multiplex PCR Methods and Compositions.
U.S. Appl. No. 14/179,399, filed Feb. 12, 2014, Methods for Non-Invasive Prenatal Ploidy Calling.
U.S. Appl. No. 14/225,356, filed Mar. 25, 2014, Methods for Preimplantation Genetic Diagnosis by Sequencing.

(56) References Cited

OTHER PUBLICATIONS

U.S. Appl. No. 14/446,232, filed Jul. 29, 2014, Methods for Non-Invasive Prenatal Ploidy Calling.
U.S. Appl. No. 14/532,666, filed Nov. 4, 2014, Methods for Non-Invasive Prenatal Ploidy Calling.
U.S. Appl. No. 14/546,321, filed Nov. 18, 2014, Methods for Non-Invasive Prenatal Ploidy Calling.
U.S. Appl. No. 14/866,223, filed Sep. 25, 2015, Methods for Non-Invasive Prenatal Ploidy Calling.
U.S. Appl. No. 14/877,925, filed Oct. 7, 2015, Highly Multiplex Pcr Methods and Compositions.
U.S. Appl. No. 14/983,128, filed Dec. 29, 2015, Methods for Non-Invasive Prenatal Ploidy Calling.
U.S. Appl. No. 13/970,436, filed Aug. 19, 2013, Method for Non-Invasive Prenatal Testing Using Parental Mosaicism Data.
U.S. Appl. No. 13/793,316, filed Mar. 11, 2013, Methods for Increasing Fetal Fraction in Maternal Blood.
U.S. Appl. No. 14/704,314, filed May 5, 2015, Methods for Increasing Fetal Fraction in Maternal Blood.
U.S. Appl. No. 14/498,629, filed Sep. 26, 2014, Cell Free Dna Diagnostic Testing Standards.
U.S. Appl. No. 14/996,097, filed Jan. 14, 2016, Cell Free Dna Diagnostic Testing Standards.
U.S. Appl. No. 14/732,632, filed Nov. 12, 2014, Systems and Methods for Detection of Aneuploidy.
U.S. Appl. No. 14/538,998, filed Nov. 24, 2014, Methods for Simultaneous Amplification of Target Loci.
U.S. Appl. No. 14/538,982, Nov. 24, 2014, Methods for Simultaneous Amplification of Target Loci.
U.S. Appl. No. 14/692,703, filed Apr. 21, 2015, Detecting Mutations and Ploidy in Chromosomal Segments.
U.S. Appl. No. 14/882,763, filed Oct. 14, 2015, Detecting Cancer Mutations and Aneuploidy in Chromosomal Segments.
U.S. Appl. No. 14/918,544, filed Oct. 20, 2015, Methods for Simultaneous Amplification of Target Loci.
U.S. Appl. No. 15/187,555, filed Jun. 20, 2016, System And Method For Cleaning Noisy Genetic Data From Target Individuals Using Genetic Data From Genetically Related Individuals.
U.S. Appl. No. 15/191,197, filed Jun. 23, 2016, System And Method For Cleaning Noisy Genetic Data From Target Individuals Using Genetic Data From Genetically Related Individuals.
Chakraborty, R. et al., "Paternity Exclusion by DNA Markers: Effects of Paternal Mutations", Journal of Forensic Sciences, vol. 41, No. 4, Jul. 1996, 671-677.
Kinnings, S.L. et al, "Factors affecting levels of circulating cell-free fetal DNA in maternal plasma and their implications for noninvasive prenatal testing", Prenatal Diagnosis, vol. 35, 2015, 816-822.
Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Rachlin, J. et al., "Computational tradeoffs in multiplex PCR assay design for SNP genotyping", BMC Genomics, vol. 6, No. 102, Jul. 25, 2005, 11 pages.
U.S. Appl. No. 15/243,915, filed Aug. 22, 2016, Methods for Non-Invasive Prenatal Ploidy Calling.
U.S. Appl. No. 15/252,795, filed Aug. 31, 2016, Methods for Non-Invasive Prenatal Ploidy Calling.
U.S. Appl. No. 15/273,332, filed Sep. 22, 2016, Methods for Non-Invasive Prenatal Ploidy Calling.
U.S. Appl. No. 15/186,774, filed Jun. 20, 2016, Systems and Methods for Determining Aneuploidy Risk Using Sample Fetal Fraction.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.

\* cited by examiner

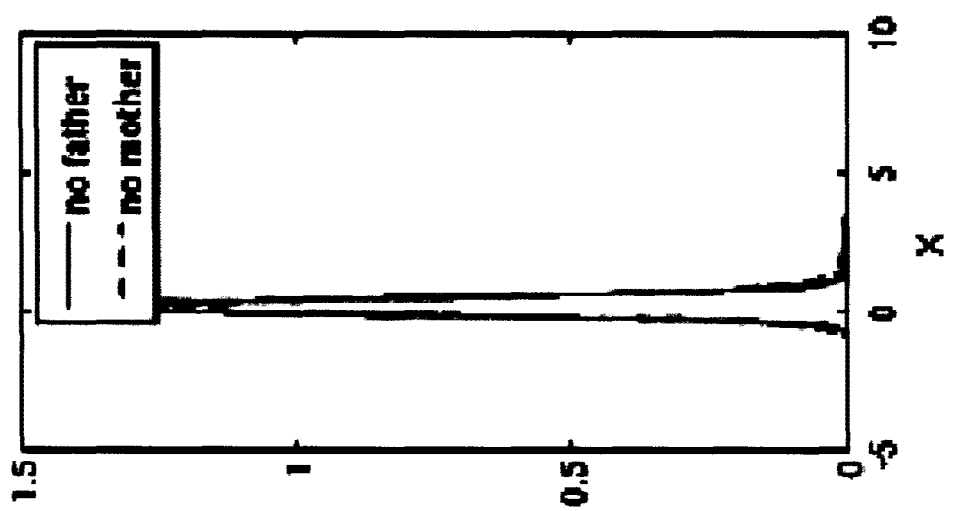
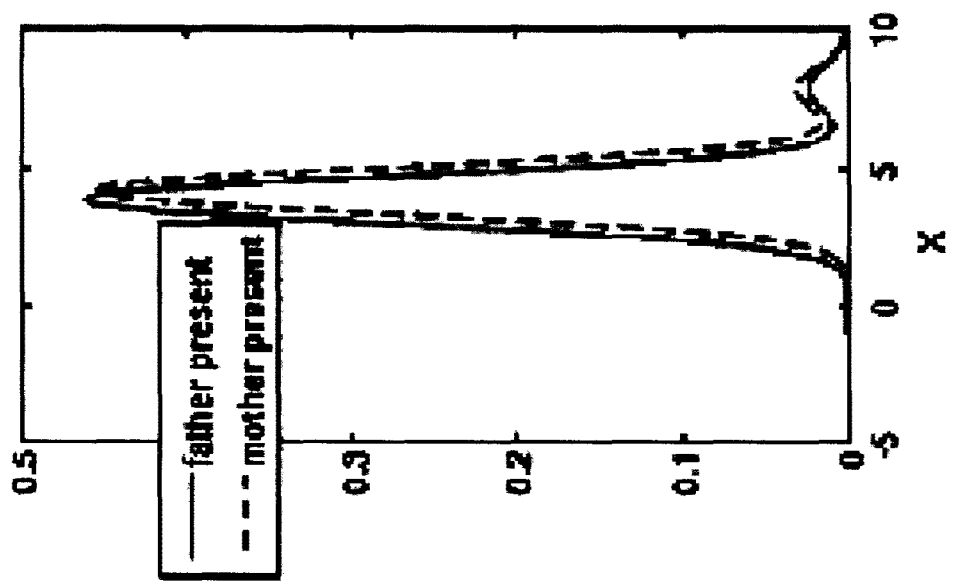
Figure 4A
Figure 4B

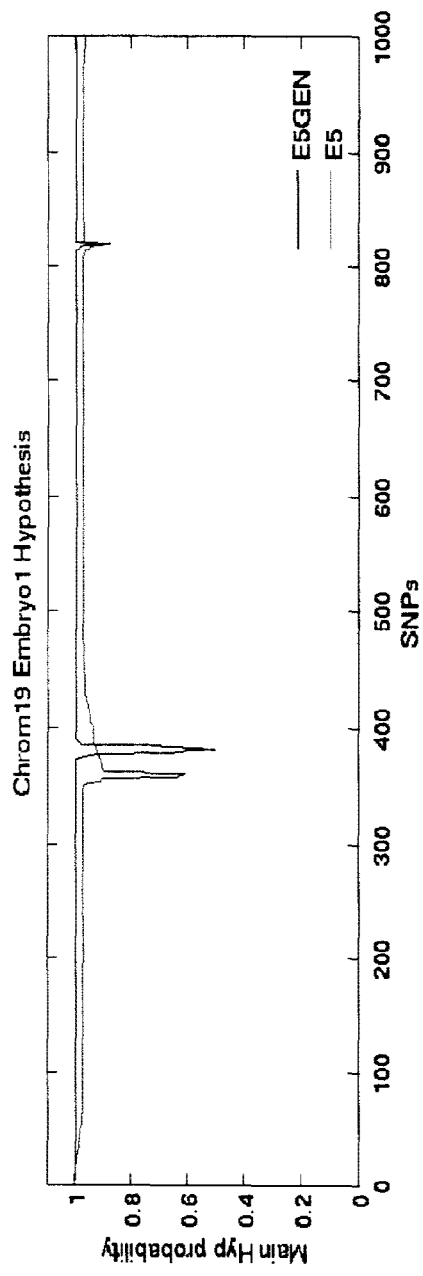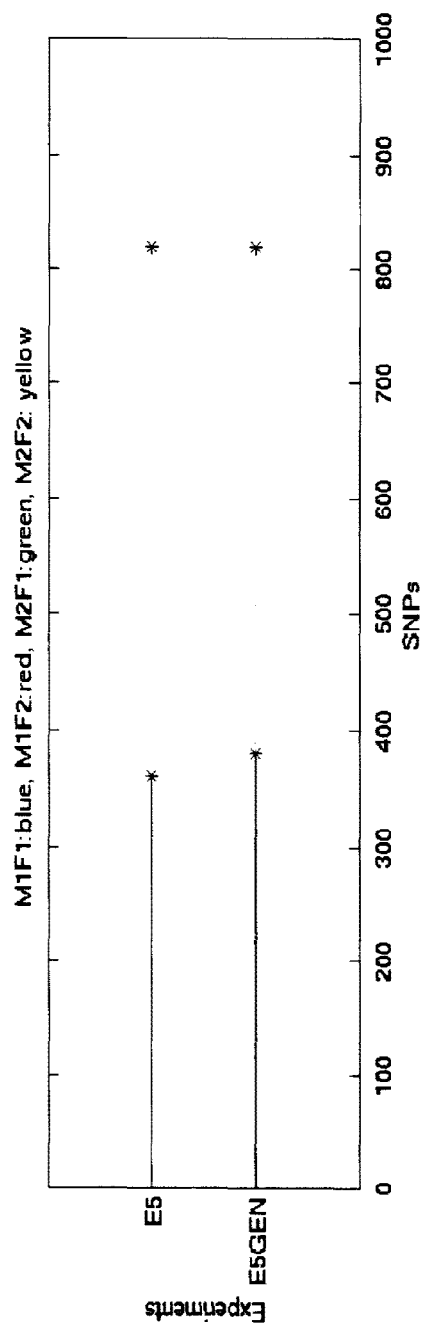
Figure 12A
Figure 12B

METHODS FOR ALLELE CALLING AND PLOIDY CALLING

CROSS-REFERENCE TO RELATED APPLICATIONS

This application is a continuation of U.S. Utility application Ser. No. 13/057,350, filed Feb. 3, 2011, which is a national phase filing under 35 U.S.C. §371 of International Application No. PCT/US2009/052730, filed on Aug. 4, 2009. International Application No. PCT/US2009/052730 claims the benefit of U.S. Provisional Application Ser. No. 61/137,851, filed Aug. 4, 2008, U.S. Provisional Application Ser. No. 61/188,343, filed Aug. 8, 2008, U.S. Provisional Application Ser. No. 61/194,854, filed Oct. 1, 2008, and U.S. Provisional Application Ser. No. 61/198,690, filed Nov. 7, 2008. The entirety of these applications are hereby incorporated herein by reference for the teachings therein.

FIELD

The present disclosure relates generally to the field of acquiring and manipulating high fidelity genetic data for medically predictive purposes.

BACKGROUND

In 2006, across the globe, roughly 800,000 in vitro fertilization (IVF) cycles were run. Of the roughly 150,000 cycles run in the US, about 10,000 involved pre-implantation genetic diagnosis (PGD). Current PGD techniques are unregulated, expensive and highly unreliable: error rates for screening disease-linked loci or aneuploidy are on the order of 10%, each screening test costs roughly $5,000, and a couple is typically forced to choose between testing aneuploidy, which afflicts roughly 50% of IVF embryos, or screening for disease-linked loci, for the single cell. There is a great need for an affordable technology that can reliably determine genetic data from a single cell in order to screen in parallel for aneuploidy, monogenic diseases such as Cystic Fibrosis, and susceptibility to complex disease phenotypes for which the multiple genetic markers are known through whole-genome association studies.

Most PGD today focuses on high-level chromosomal abnormalities such as aneuploidy and balanced translocations with the primary outcomes being successful implantation and a take-home baby. The other main focus of PGD is for genetic disease screening, with the primary outcome being a healthy baby not afflicted with a genetically heritable disease for which one or both parents are carriers. In both cases, the likelihood of the desired outcome is enhanced by excluding genetically suboptimal embryos from transfer and implantation in the mother.

The process of PGD during IVF currently involves extracting a single cell from the roughly eight cells of an early-stage embryo for analysis. Isolation of single cells from human embryos, while highly technical, is now routine in IVF clinics. Both polar bodies and blastomeres have been isolated with success. The most common technique is to remove single blastomeres from day 3 embryos (6 or 8 cell stage). Embryos are transferred to a special cell culture medium (standard culture medium lacking calcium and magnesium), and a hole is introduced into the zona pellucida using an acidic solution, laser, or mechanical techniques. The technician then uses a biopsy pipette to remove a single blastomere with a visible nucleus. Features of the DNA of the single (or occasionally multiple) blastomere are measured using a variety of techniques. Since only a single copy of the DNA is available from one cell, direct measurements of the DNA are highly error-prone, or noisy. There is a great need for a technique that can correct, or make more accurate, these noisy genetic measurements.

Normal humans have two sets of 23 chromosomes in every diploid cell, with one copy coming from each parent. Aneuploidy, the state of a cell with extra or missing chromosome(s), and uniparental disomy, the state of a cell with two of a given chromosome which both originate from one parent, are believed to be responsible for a large percentage of failed implantations and miscarriages, and some genetic diseases. When only certain cells in an individual are aneuploid, the individual is said to exhibit mosaicism. Detection of chromosomal abnormalities can identify individuals or embryos with conditions such as Down syndrome, Klinefelter's syndrome, and Turner syndrome, among others, in addition to increasing the chances of a successful pregnancy. Testing for chromosomal abnormalities is especially important as the age of a potential mother increases: between the ages of 35 and 40 it is estimated that between 40% and 50% of the embryos are abnormal, and above the age of 40, more than half of the embryos are like to be abnormal. The main cause of aneuploidy is nondisjunction during meiosis. Maternal nondisjunction constitutes approximately 88% of all nondisjunction of which about 65% occurs in meiosis I and 23% in meiosis II. Common types of human aneuploidy include trisomy from meiosis I nondisjunction, monosomy, and uniparental disomy. In a particular type of trisomy that arises in meiosis II nondisjunction, or M2 trisomy, an extra chromosome is identical to one of the two normal chromosomes. M2 trisomy is particularly difficult to detect. There is a great need for a better method that can detect many or all types of aneuploidy at most or all of the chromosomes efficiently and with high accuracy, including a method that can differentiate not only euploidy from aneuploidy, but also that can differentiate different types of aneuploidy from one another.

Karyotyping, the traditional method used for the prediction of aneuploidy and mosaicism is giving way to other more high-throughput, more cost effective methods such as Flow Cytometry (FC) and fluorescent in situ hybridization (FISH). Currently, the vast majority of prenatal diagnoses use FISH, which can determine large chromosomal aberrations and PCR/electrophoresis, and which can determine a handful of SNPs or other allele calls. One advantage of FISH is that it is less expensive than karyotyping, but the technique is complex and expensive enough that generally a small selection of chromosomes are tested (usually chromosomes 13, 18, 21, X, Y; also sometimes 8, 9, 15, 16, 17, 22); in addition, FISH has a low level of specificity. Roughly seventy-five percent of PGD today measures high-level chromosomal abnormalities such as aneuploidy using FISH with error rates on the order of 10-15%. There is a great demand for an aneuploidy screening method that has a higher throughput, lower cost, and greater accuracy.

The number of known disease associated genetic alleles is over 380 according to OMIM and steadily climbing. Consequently, it is becoming increasingly relevant to analyze multiple positions on the embryonic DNA, or loci, that are associated with particular phenotypes. A clear advantage of pre-implantation genetic diagnosis over prenatal diagnosis is that it avoids some of the ethical issues regarding possible choices of action once undesirable phenotypes have been detected. A need exists for a method for more extensive genotyping of embryos at the pre-implantation stage.

There are a number of advanced technologies that enable the diagnosis of genetic aberrations at one or a few loci at the single-cell level. These include interphase chromosome conversion, comparative genomic hybridization, fluorescent PCR, mini-sequencing and whole genome amplification. The reliability of the data generated by all of these techniques relies on the quality of the DNA preparation. Better methods for the preparation of single-cell DNA for amplification and PGD are therefore needed and are under study. All genotyping techniques, when used on single cells, small numbers of cells, or fragments of DNA, suffer from integrity issues, most notably allele drop out (ADO). This is exacerbated in the context of in-vitro fertilization since the efficiency of the hybridization reaction is low, and the technique must operate quickly in order to genotype the embryo within the time period of maximal embryo viability. There exists a great need for a method that alleviates the problem of a high ADO rate when measuring genetic data from one or a small number of cells, especially when time constraints exist.

SUMMARY

In one embodiment of the present disclosure, the disclosed method enables the reconstruction of incomplete or noisy genetic data, including the determination of the identity of individual alleles, haplotypes, sequences, insertions, deletions, repeats, and the determination of chromosome copy number on a target individual, all with high fidelity, using secondary genetic data as a source of information. While the disclosure focuses on genetic data from human subjects, and more specifically on as-yet not implanted embryos or developing fetuses, as well as related individuals, it should be noted that the methods disclosed apply to the genetic data of a range of organisms, in a range of contexts. The techniques described for cleaning genetic data are most relevant in the context of pre-implantation diagnosis during in-vitro fertilization, prenatal diagnosis in conjunction with amniocentesis, chorion villus biopsy, fetal tissue sampling, and non-invasive prenatal diagnosis, where a small quantity of fetal genetic material is isolated from maternal blood. The use of this method may facilitate diagnoses focusing on inheritable diseases, chromosome copy number predictions, increased likelihoods of defects or abnormalities, as well as making predictions of susceptibility to various disease- and non-disease phenotypes for individuals to enhance clinical and lifestyle decisions.

In an embodiment of the present disclosure, a method for determining a ploidy state of at least one chromosome in a target individual includes obtaining genetic data from the target individual and from one or more related individuals; creating a set of at least one ploidy state hypothesis for each of the chromosomes of the target individual; using one or more expert techniques to determine a statistical probability for each ploidy state hypothesis in the set, for each expert technique used, given the obtained genetic data; combining, for each ploidy state hypothesis, the statistical probabilities as determined by the one or more expert techniques; and determining the ploidy state for each of the chromosomes in the target individual based on the combined statistical probabilities of each of the ploidy state hypotheses.

In an embodiment of the present disclosure, a method for determining an allelic state in a set of alleles, in a target individual, and from one or both parents of the target individual, and optionally from one or more related individuals includes obtaining genetic data from the target individual, and from the one or both parents, and from any related individuals; creating a set of at least one allelic hypothesis for the target individual, and for the one or both parents, and optionally for the one or more related individuals, where the hypotheses describe possible allelic states in the set of alleles; determining a statistical probability for each allelic hypothesis in the set of hypotheses given the obtained genetic data; and determining the allelic state for each of the alleles in the set of alleles for the target individual, and for the one or both parents, and optionally for the one or more related individuals, based on the statistical probabilities of each of the allelic hypotheses.

In an embodiment of the present disclosure, a method for determining a ploidy state of at least one chromosome in a target individual includes obtaining genetic data from the target individual, and from both parent of the target individual, and from one or more siblings of the target individual, wherein the genetic data includes data relating to at least one chromosome; determining a ploidy state of the at least one chromosome in the target individual and in the one or more siblings of the target individual by using one or more expert techniques, wherein none of the expert techniques requires phased genetic data as input; determining phased genetic data of the target individual, and of the parents of the target individual, and of the one or more siblings of the target individual, using an informatics based method, and the obtained genetic data from the target individual, and from the parents of the target individual, and from the one or more siblings of the target individual that were determined to be euploid at that chromosome; and redetermining the ploidy state of the at least one chromosome of the target individual, using one or more expert techniques, at least one of which requires phased genetic data as input, and the determined phased genetic data of the target individual, and of the parents of the target individual, and of the one or more siblings of the target individual.

In an embodiment of the present disclosure, the method makes use of knowledge of the genetic data of the target embryo, the genetic data from mother and the father such as diploid tissue samples, and possibly genetic data from one or more of the following: sperm from the father, haploid samples from the mother or blastomeres from that same or other embryos derived from the mother's and father's gametes, together with the knowledge of the mechanism of meiosis and the imperfect measurement of the target embryonic DNA, in order to reconstruct, in silico, the embryonic DNA at the location of key loci with a high degree of confidence. In one aspect of the present disclosure, genetic data derived from other related individuals, such as other embryos, brothers and sisters, grandparents or other relatives can also be used to increase the fidelity of the reconstructed embryonic DNA. In one embodiment of the present disclosure, these genetic data may be used to determine the ploidy state at one or more chromosomes on the individual. In one aspect of the present disclosure, each of the set of genetic data measured from a set of related individuals is used to increase the fidelity of the other genetic data. It is important to note that in one aspect of the present disclosure, the parental and other secondary genetic data allows the reconstruction not only of SNPs that were measured poorly, but also of insertions, deletions, repeats, and of SNPs or whole regions of DNA that were not measured at all. In another aspect of the present disclosure, the genetic data of the target individual, along with the secondary genetic data of related individuals, is used to determine the ploidy state, or copy number, at one, several, or all of the chromosomes of the individual.

In an embodiment of the present disclosure, the fetal or embryonic genomic data, with or without the use of genetic data from related individuals, can be used to detect if the cell is aneuploid, that is, where the wrong number of a chromosome is present in a cell, or if the wrong number of sexual chromosomes are present in the cell. The genetic data can also be used to detect for uniparental disomy, a condition in which two of a given chromosome are present, both of which originate from one parent. This is done by creating a set of hypotheses about the potential states of the DNA, and testing to see which hypothesis has the highest probability of being true given the measured data. Note that the use of high throughput genotyping data for screening for aneuploidy enables a single blastomere from each embryo to be used both to measure multiple disease-linked loci as well as to screen for aneuploidy.

In an embodiment of the present disclosure, the direct measurements of the amount of genetic material, amplified or unamplified, present at a plurality of loci, can be used to detect for monosomy, uniparental disomy, matched trisomy, unmatched trisomy, tetrasomy, and other aneuploidy states. One embodiment of the present disclosure takes advantage of the fact that under some conditions, the average level of amplification and measurement signal output is invariant across the chromosomes, and thus the average amount of genetic material measured at a set of neighboring loci will be proportional to the number of homologous chromosomes present, and the ploidy state may be called in a statistically significant fashion. In another embodiment, different alleles have a statistically different characteristic amplification profiles given a certain parent context and a certain ploidy state; these characteristic differences can be used to determine the ploidy state of the chromosome.

In an embodiment of the present disclosure, the ploidy state, as determined by one aspect of the present disclosure, may be used to select the appropriate input for an allele calling embodiment of the present disclosure. In another aspect of the present disclosure, the phased, reconstructed genetic data from the target individual and/or from one or more related individuals may be used as input for a ploidy calling aspect of the present disclosure. In one embodiment of the present disclosure, the output from one aspect of the present disclosure may be used as input for, or to help select appropriate input for other aspects of the present disclosure in an iterative process.

It will be recognized by a person of ordinary skill in the art, given the benefit of this disclosure, that various aspects and embodiments of this disclosure may implemented in combination or separately.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A shows a cumulative distribution function curve for a disomic chromosome. FIG. 2B shows a cumulative distribution function curve for a nullisomic chromosome. FIG. 2C shows a cumulative distribution function curve for a monosomic chromosome. FIG. 2D shows a cumulative distribution function curve for a maternal trisomic chromosome. The relationship between cumulative distribution function curves for different parent contexts vary with the ploidy state.

FIGS. 4A and 4B show a distribution of the genetic data of each of the parents using the Presence of Parents technique disclosed herein. FIG. 4A shows a distribution where genetic data from each parent is present. FIG. 4B shows a distribution where genetic data from each parent is absent.

FIG. 8A shows curve fits for allelic data for five different ploidy hypotheses using the Kernel method disclosed herein. FIG. 8B shows curve fits for allelic data for five different ploidy hypotheses using a Gaussian Fit disclosed herein. FIG. 8C shows a histogram of the measured allelic data from one context, AA|BB-BB|AA.

FIG. 10A shows the average actual hit rate graphed against a predicted confidence. FIG. 10B shows the relative population of the bin.

FIG. 11A shows the average actual hit rate graphed against a predicted confidence. FIG. 11B shows the relative population of the bin.

FIGS. 12A and 12B show allele confidence plotted along a chromosome to determine a location of a crossover. FIG. 12A shows the allele call confidences for a set of alleles located along one chromosome, as averaged over a set of neighboring alleles. The sets or alleles using different methods. FIG. 12B shows a location of a crossover along the chromosome.

Figure 1:
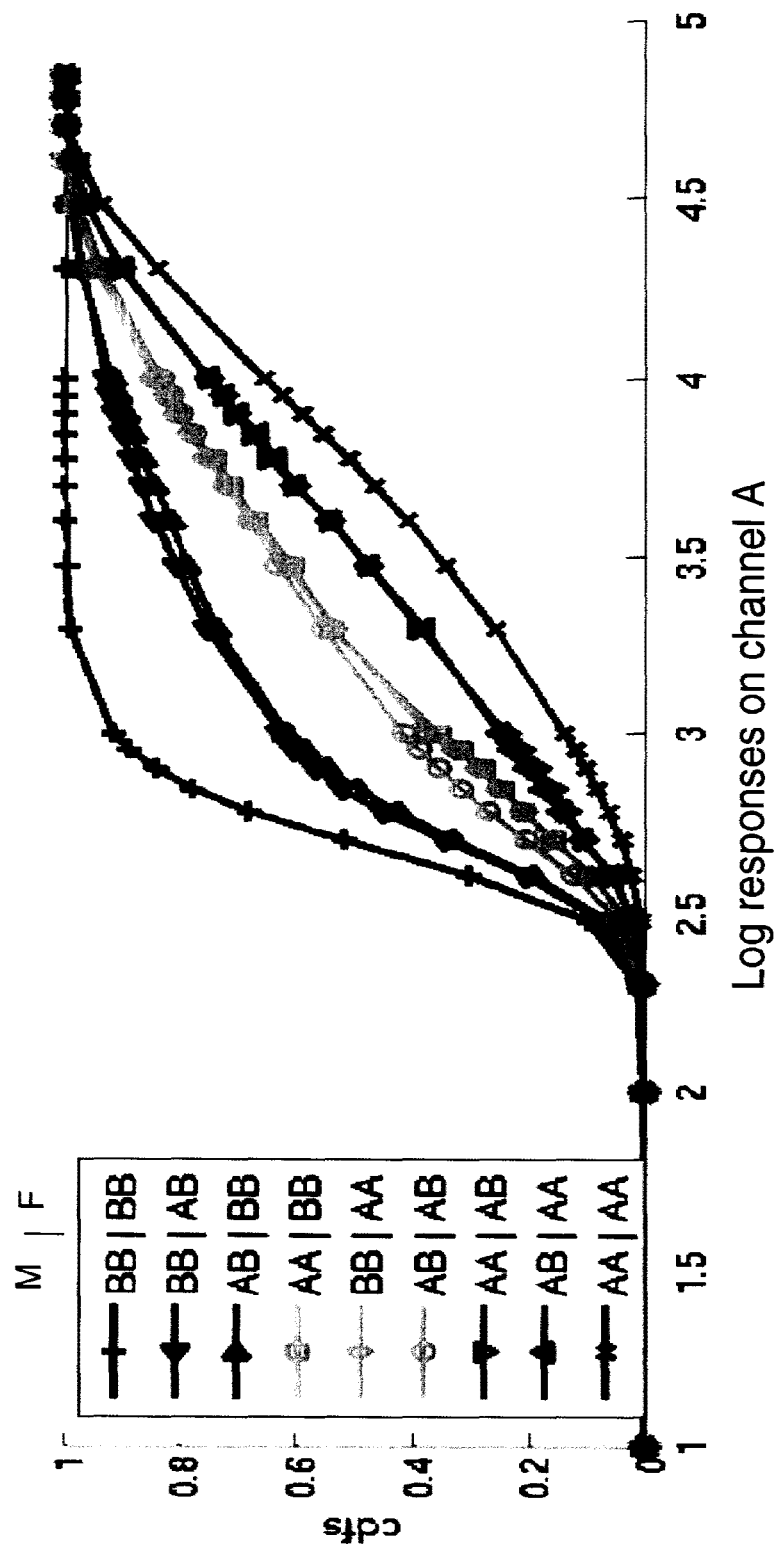
FIG. 1 shows cumulative distribution function curves for a disomic chromosome. The cumulative distribution function curves are shown for each of the parental contexts.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

In an embodiment of the present disclosure, the genetic state of a cell or set of cells can be determined. Copy number calling is the concept of determining the number and identity of chromosomes in a given cell, group of cells, or set of deoxyribonucleic acid (DNA). Allele calling is the concept of determining the allelic state of a given cell, group of cells, or set of DNA, at a set of alleles, including Single Nucleotide Polymorphisms (SNPs), insertions, deletions, repeats, sequences, or other base pair information. The present disclosure allows the determination of aneuploidy, as well as allele calling, from a single cell, or other small set of DNA, provided the genome of at least one or both parents are available. Some aspects of the present disclosure use the concept that within a set of related individuals there will be sets of DNA that are nearly identical, and that using the measurements of the genetic data along with a knowledge of mechanism of meiosis, it is possible to determine the genetic state of the relevant individuals, by inference, with greater accuracy that may be possible using the individual measurements alone. This is done by determining which segments of chromosomes of related individuals were involved in gamete formation and, when necessary, where crossovers may have occurred during meiosis, and therefore which segments of the genomes of related individuals are expected to be nearly identical to sections of the target genome. This may be particularly useful in the case of preimplantation genetic diagnosis, or prenatal diagnosis, wherein a limited amount of DNA is available, and where the determination of the ploidy state of a target, an embryo or fetus in these cases, has a high clinical impact.

There are many possible mathematical techniques to determine the aneuploidy state from a set of target genetic data. Some of these techniques are discussed in this disclosure, but other techniques could be used equally well. In one embodiment of the present disclosure, both qualitative and/or quantitative data may be used. In one embodiment of the present disclosure, parental data may be used to infer target genome data that may have been measured poorly, incorrectly, or not at all. In one embodiment, inferred genetic data from one or more individual can be used to increase the likelihood of the ploidy state being determined correctly. In one embodiment of the present disclosure, a plurality of techniques may be used, each of which are able to rule out certain ploidy states, or determine the relative likelihood of certain ploidy states, and the probabilities of those predictions may be combined to produce a prediction of the ploidy state with higher confidence that is possible when using one technique alone. A confidence can be computed for each chromosomal call made.

DNA measurements, whether obtained by sequencing techniques, genotyping arrays, or any other technique, contain a degree of error. The relative confidence in a given DNA measurement is affected by many factors, including the amplification method, the technology used to measure the DNA, the protocol used, the amount of DNA used, the integrity of the DNA used, the operator, and the freshness of the reagents, just to name a few. One way to increase the accuracy of the measurements is to use informatics based techniques to infer the correct genetic state of the DNA in the target based on the knowledge of the genetic state of related individuals. Since related individuals are expected to share certain aspect of their genetic state, when the genetic data from a plurality of related individuals is considered together, it is possible to identify likely errors in the measurements, and increase the accuracy of the knowledge of the genetic states of all the related individuals. In addition, a confidence may be computed for each call made.

In some aspects of the present disclosure, the target individual is an embryo, and the purpose of applying the disclosed method to the genetic data of the embryo is to allow a doctor or other agent to make an informed choice of which embryo(s) should be implanted during IVF. In another aspect of the present disclosure, the target individual is a fetus, and the purpose of applying the disclosed method to genetic data of the fetus is to allow a doctor or other agent to make an informed choice about possible clinical decisions or other actions to be taken with respect to the fetus.

Definitions

SNP (Single Nucleotide Polymorphism) may refer to a single nucleotide that may differ between the genomes of two members of the same species. The usage of the term should not imply any limit on the frequency with which each variant occurs.

To call a SNP may refer to the act of making a decision about the true state of a particular base pair, taking into account the direct and indirect evidence.

Sequence may refer to a DNA sequence or a genetic sequence. It may refer to the primary, physical structure of the DNA molecule or strand in an individual.

Locus may refer to a particular region of interest on the DNA of an individual, which may refer to a SNP, the site of a possible insertion or deletion, or the site of some other relevant genetic variation. Disease-linked SNPs may also refer to disease-linked loci.

Allele may refer to the genes that occupy a particular locus.

To call an allele may refer to the act of determining the genetic state at a particular locus of DNA. This may involve calling a SNP, a plurality of SNPs, or determining whether or not an insertion or deletion is present at that locus, or determining the number of insertions that may be present at that locus, or determining whether some other genetic variant is present at that locus.

Correct allele call may refer to an allele call that correctly reflects the true state of the actual genetic material of an individual.

To clean genetic data may refer to the act of taking imperfect genetic data and correcting some or all of the errors or fill in missing data at one or more loci. In the context of this disclosure, this may involve using the genetic data of related individuals and the method described herein.

To increase the fidelity of allele calls may refer to the act of cleaning genetic data with respect to a set of alleles.

Imperfect genetic data may refer to genetic data with any of the following: allele dropouts, uncertain base pair measurements, incorrect base pair measurements, missing base pair measurements, uncertain measurements of insertions or deletions, uncertain measurements of chromosome segment copy numbers, spurious signals, missing measurements, other errors, or combinations thereof.

Noisy genetic data may refer to imperfect genetic data, also called incomplete genetic data.

Uncleaned genetic data may refer to genetic data as measured, that is, where no method has been used to correct for the presence of noise or errors in the raw genetic data; also called crude genetic data.

Confidence may refer to the statistical likelihood that the called SNP, allele, set of alleles, or determined number of chromosome segment copies correctly represents the real genetic state of the individual.

Ploidy calling, also "chromosome copy number calling", or "copy number calling" (CNC), may be the act of determining the quantity and chromosomal identity of one or more chromosomes present in a cell.

Aneuploidy may refer to the state where the wrong number of chromosomes are present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. When referring to a single chromosome, it may refer to the case where more or less than two homologous chromosomes are present.

Ploidy State may be the quantity and chromosomal identity of one or more chromosomes in a cell.

Chromosomal identity may refer to the referent chromosome number. Normal humans have 22 types of numbered autosomal chromosomes, and two types of sex chromosomes. It may also refer to the parental origin of the chromosome. It may also refer to a specific chromosome inherited from the parent. It may also refer to other identifying features of a chromosome.

The State of the Genetic Material or simply "genetic state" may refer to the identity of a set of SNPs on the DNA, it may refer to the phased haplotypes of the genetic material, and it may refer to the sequence of the DNA, including insertions, deletions, repeats and mutations. It may also refer to the ploidy state of one or more chromosomes, chromosomal segments, or set of chromosomal segments.

Allelic Data may refer to a set of genotypic data concerning a set of one or more alleles. It may refer to the phased, haplotypic data. It may refer to SNP identities, and it may refer to the sequence data of the DNA, including insertions, deletions, repeats and mutations. It may include the parental origin of each allele.

Allelic State may refer to the actual state of the genes in a set of one or more alleles. It may refer to the actual state of the genes described by the allelic data.

Matched copy error, also 'matching chromosome aneuploidy', or 'MCA' may be a state of aneuploidy where one cell contains two identical or nearly identical chromosomes. This type of aneuploidy may arise during the formation of the gametes in mitosis, and may be referred to as a mitotic non-disjunction error.

Unmatched copy error, also "Unique Chromosome Aneuploidy" or "UCA" may be a state of aneuploidy where one cell contains two chromosomes that are from the same parent, and that may be homologous but not identical. This type of aneuploidy may arise during meiosis, and may be referred to as a meiotic error.

Mosaicism may refer to a set of cells in an embryo, or other individual that are heterogeneous with respect to their ploidy state.

Homologous Chromosomes may be chromosomes that contain the same set of genes that may normally pair up during meiosis.

Identical Chromosomes may be chromosomes that contain the same set of genes, and for each gene they have the same set of alleles that are identical, or nearly identical.

Allele Drop Out or "ADO" may refer to the situation where one of the base pairs in a set of base pairs from homologous chromosomes at a given allele is not detected.

Locus Drop Out or "LDO" may refer to the situation where both base pairs in a set of base pairs from homologous chromosomes at a given allele are not detected.

Homozygous refer to having similar alleles as corresponding chromosomal loci.

Heterozygous may refer to having dissimilar alleles as corresponding chromosomal loci.

Chromosomal Region may refer to a segment of a chromosome, or a full chromosome.

Segment of a Chromosome may refer to a section of a chromosome that can range in size from one base pair to the entire chromosome.

Chromosome may refer to either a full chromosome, or also a segment or section of a chromosome.

Copies may refer to the number of copies of a chromosome segment may refer to identical copies, or it may refer to non-identical, homologous copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotype is a combination of alleles at multiple loci that are transmitted together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated.

Haplotypic Data also called 'phased data' or 'ordered genetic data;' may refer to data from a single chromosome in a diploid or polyploid genome, i.e., either the segregated maternal or paternal copy of a chromosome in a diploid genome.

Phasing may refer to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data may refer to genetic data where the haplotype been determined.

Phased Allele Call Data may refer to allelic data where the allelic state, including the haplotype data, has been determined. In one embodiment, phased parental allele call data, as determined by an informatics based method, may be used as obtained genetic data in a ploidy calling aspect of the present disclosure.

Unordered Genetic Data may refer to pooled data derived from measurements on two or more chromosomes in a diploid or polyploid genome, e.g., both the maternal and paternal copies of a particular chromosome in a diploid genome.

Genetic data 'in', 'of', 'at', 'from' or 'on' an individual may refer to the data describing aspects of the genome of an individual. It may refer to one or a set of loci, partial or entire sequences, partial or entire chromosomes, or the entire genome.

Hypothesis may refer to a set of possible ploidy states at a given set of chromosomes, or a set of possible allelic states at a given set of loci. The set of possibilities may contain one or more elements.

Copy number hypothesis, also 'ploidy state hypothesis,' may refer to a hypothesis concerning how many copies of a particular chromosome are in an individual. It may also refer to a hypothesis concerning the identity of each of the chromosomes, including the parent of origin of each chromosome, and which of the parent's two chromosomes are present in the individual. It may also refer to a hypothesis concerning which chromosomes, or chromosome segments, if any, from a related individual correspond genetically to a given chromosome from an individual.

Allelic Hypothesis may refer to a possible allelic state for a given set of alleles. A set of allelic hypotheses may refer to a set of hypotheses that describe, together, all of the possible allelic states in the set of alleles. It may also refer to a hypothesis concerning which chromosomes, or chromosome segments, if any, from a related individual correspond genetically to a given chromosome from an individual.

Target Individual may refer to the individual whose genetic data is being determined. In one context, only a limited amount of DNA is available from the target individual. In one context, the target individual is an embryo or a fetus. In some embodiments, there may be more than one target individual. In some embodiments, each child, embryo, fetus or sperm that originated from a pair of parents may be considered target individuals.

Related Individual may refer to any individual who is genetically related to, and thus shares haplotype blocks with, the target individual. In one context, the related individual may be a genetic parent of the target individual, or any genetic material derived from a parent, such as a sperm, a polar body, an embryo, a fetus, or a child. It may also refer to a sibling or a grandparent.

Sibling may refer to any individual whose parents are the same as the individual in question. In some embodiments, it may refer to a born child, an embryo, or a fetus, or one or more cells originating from a born child, an embryo, or a fetus. A sibling may also refer to a haploid individual that originates from one of the parents, such as a sperm, a polar body, or any other set of haplotypic genetic matter. An individual may be considered to be a sibling of itself.

Parent may refer to the genetic mother or father of an individual. An individual will typically have two parents, a mother and a father. A parent may be considered to be an individual.

Parental context may refer to the genetic state of a given SNP, on each of the two relevant chromosomes for each of the two parents of the target.

Develop as desired, also 'develop normally,' may refer to a viable embryo implanting in a uterus and resulting in a pregnancy. It may also refer to the pregnancy continuing and resulting in a live birth. It may also refer to the born child being free of chromosomal abnormalities. It may also refer to the born child being free of other undesired genetic conditions such as disease-linked genes. The term 'develop as desired' encompasses anything that may be desired by parents or healthcare facilitators. In some cases, 'develop as desired' may refer to an unviable or viable embryo that is useful for medical research or other purposes.

Insertion into a uterus may refer to the process of transferring an embryo into the uterine cavity in the context of in vitro fertilization.

Clinical Decision may refer to any decision to take an action, or not to take an action, that has an outcome that affects the health or survival of an individual. In the context of IVF, a clinical decision may refer to a decision to implant or not implant one or more embryos. In the context of prenatal diagnosis, a clinical decision may refer to a decision to abort or not abort a fetus. A clinical decision may refer to a decision to conduct further testing.

Platform response may refer to the mathematical characterization of the input/output characteristics of a genetic measurement platform, and may be used as a measure of the statistically predictable measurement differences.

Informatics based method may refer to a method designed to determine the ploidy state at one or more chromosomes or the allelic state at one or more alleles by statistically inferring the most likely state, rather than by directly physically measuring the state. In one embodiment of the present disclosure, the informatics based technique may be one disclosed in this patent. In one embodiment of the present disclosure it may be PARENTAL SUPPORT™.

Expert Technique may refer to a method used to determine a genetic state. In one embodiment it may refer to a method used to determine or aid in the determination of the ploidy state of an individual. It may refer to an algorithm, a quantitative method, a qualitative method, and/or a computer based technique.

Channel Intensity may refer to the strength of the fluorescent or other signal associated with a given allele, base pair or other genetic marker that is output from a method that is used to measure genetic data. It may refer to a set of outputs. In one embodiment, it may refer to the set of outputs from a genotyping array.

Cumulative Distribution Function (CDF) curve may refer to a monotone increasing, right continuous probability distribution of a variable, where the 'y' coordinate of a point on the curve refers to the probability that the variable takes on a value less than or equal to the 'x' coordinate of the point.

Parental Context

The parental context may refer to the genetic state of a given SNP, on each of the two relevant chromosomes for each of the two parents of the target. Note that in one embodiment, the parental context does not refer to the allelic state of the target, rather, it refers to the allelic state of the parents. The parental context for a given SNP may consist of four base pairs, two paternal and two maternal; they may be the same or different from one another. It is typically written as "$m_1 m_2 | f_1 f_2$", where $m_1$ and $m_2$ are the genetic state of the given SNP on the two maternal chromosomes, and $f_1$ and $f_2$ are the genetic state of the given SNP on the two paternal chromosomes. In some embodiments, the parental context may be written as "$f_1 f_2 | m_1 m_2$". Note that subscripts "1" and "2" refer to the genotype, at the given allele, of the first and second chromosome; also note that the choice of which chromosome is labeled "1" and which is labeled "2" is arbitrary.

Note that in this disclosure, A and B are often used to generically represent base pair identities; A or B could equally well represent C (cytosine), G (guanine), A (adenine) or T (thymine). For example, if, at a given allele, the mother's genotype was T on one chromosome, and G on the homologous chromosome, and the father's genotype at that allele is G on both of the homologous chromosomes, one may say that the target individual's allele has the parental context of AB|BB. Note that, in theory, any of the four possible alleles could occur at a given allele, and thus it is possible, for example, for the mother to have a genotype of AT, and the father to have a genotype of GC at a given allele. However, empirical data indicate that in most cases only two of the four possible base pairs are observed at a given allele. In this disclosure the discussion assumes that only two possible base pairs will be observed at a given allele, although it should be obvious to one skilled in the art how the embodiments disclosed herein could be modified to take into account the cases where this assumption does not hold.

A "parental context" may refer to a set or subset of target SNPs that have the same parental context. For example, if one were to measure 1000 alleles on a given chromosome on a target individual, then the context AA|BB could refer to the set of all alleles in the group of 1,000 alleles where the genotype of the mother of the target was homozygous, and the genotype of the father of the target is homozygous, but where the maternal genotype and the paternal genotype are dissimilar at that locus. If the parental data is not phased, and thus AB=BA, then there are nine possible parental contexts:

AA|AA, AA|AB, AA|BB, AB|AA, AB|AB, AB|BB, BB|AA, BB|AB, and BB|BB. If the parental data is phased, and thus AB BA, then there are sixteen different possible parental contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. Every SNP allele on a chromosome, excluding some SNPs on the sex chromosomes, has one of these parental contexts. The set of SNPs wherein the parental context for one parent is heterozygous may be referred to as the heterozygous context.

Hypotheses

A hypothesis may refer to a possible genetic state. It may refer to a possible ploidy state. It may refer to a possible allelic state. A set of hypotheses refers to a set of possible genetic states. In some embodiments, a set of hypotheses may be designed such that one hypothesis from the set will correspond to the actual genetic state of any given individual. In some embodiments, a set of hypotheses may be designed such that every possible genetic state may be described by at least one hypothesis from the set. In some embodiments of the present disclosure, one aspect of the method is to determine which hypothesis corresponds to the actual genetic state of the individual in question.

In another embodiment of the present disclosure, one step involves creating a hypothesis. In some embodiments it may be a copy number hypothesis. In some embodiments it may involve a hypothesis concerning which segments of a chromosome from each of the related individuals correspond genetically to which segments, if any, of the other related individuals. Creating a hypothesis may refer to the act of setting the limits of the variables such that the entire set of possible genetic states that are under consideration are encompassed by those variables.

A 'copy number hypothesis', also called a 'ploidy hypothesis', or a 'ploidy state hypothesis', may refer to a hypothesis concerning a possible ploidy state for a given chromosome, or section of a chromosome, in the target individual. It may also refer to the ploidy state at more than one of the chromosomes in the individual. A set of copy number hypotheses may refer to a set of hypotheses where each hypothesis corresponds to a different possible ploidy state in an individual. A normal individual contains one of each chromosome from each parent. However, due to errors in meiosis and mitosis, it is possible for an individual to have 0, 1, 2, or more of a given chromosome from each parent. In practice, it is rare to see more that two of a given chromosomes from a parent. In this disclosure, the embodiments only consider the possible hypotheses where 0, 1, or 2 copies of a given chromosome come from a parent. In some embodiments, for a given chromosome, there are nine possible hypotheses: the three possible hypothesis concerning 0, 1, or 2 chromosomes of maternal origin, multiplied by the three possible hypotheses concerning 0, 1, or 2 chromosomes of paternal origin. Let (m,f) refer to the hypothesis where m is the number of a given chromosome inherited from the mother, and f is the number of a given chromosome inherited from the father. Therefore, the nine hypotheses are (0,0), (0,1), (0,2), (1,0), (1,1), (1,2), (2,0), (2,1), and (2,2). The different hypotheses correspond to different ploidy states. For example, (1,1) refers to a normal disomic chromosome; (2,1) refers to a maternal trisomy, and (0,1) refers to a paternal monosomy. In some embodiments, the case where two chromosomes are inherited from one parent and one chromosomes is inherited from the other parent may be further differentiated into two cases: one where the two chromosomes are identical (matched copy error), and one where the two chromosomes are homologous but not identical (unmatched copy error). In these embodiments, there are sixteen possible hypotheses. It is possible to use other sets of hypotheses, and it should be obvious for one skilled in the art how to modify the disclosed method to take into account a different number of hypotheses.

In some embodiments of the present disclosure, the ploidy hypothesis may refer to a hypothesis concerning which chromosome from other related individuals correspond to a chromosome found in the target individual's genome. In some embodiments, a key to the method is the fact that related individuals can be expected to share haplotype blocks, and using measured genetic data from related individuals, along with a knowledge of which haplotype blocks match between the target individual and the related individual, it is possible to infer the correct genetic data for a target individual with higher confidence than using the target individual's genetic measurements alone. As such, in some embodiments, the ploidy hypothesis may concern not only the number of chromosomes, but also which chromosomes in related individuals are identical, or nearly identical, with one or more chromosomes in the target individual.

An allelic hypothesis, or an 'allelic state hypothesis' may refer to a hypothesis concerning a possible allelic state of a set of alleles. In some embodiments, a key to this method is, as described above, related individuals may share haplotype blocks, which may help the reconstruction of genetic data that was not perfectly measured. An allelic hypothesis may also refer to a hypothesis concerning which chromosomes, or chromosome segments, if any, from a related individual correspond genetically to a given chromosome from an individual. The theory of meiosis tells us that each chromosome in an individual is inherited from one of the two parents, and this is a nearly identical copy of a parental chromosome. Therefore, if the haplotypes of the parents are known, that is, the phased genotype of the parents, then the genotype of the child may be inferred as well. (The term child, here, is meant to include any individual formed from two gametes, one from the mother and one from the father.) In one embodiment of the present disclosure, the allelic hypthsis describes a possible allelic state, at a set of alleles, including the haplotypes, as well as which chromosomes from related individuals may match the chromosome(s) which contain the set of alleles.

Once the set of hypotheses have been defined, when the algorithms operate on the input genetic data, they may output a determined statistical probability for each of the hypotheses under consideration. The probabilities of the various hypotheses may be determined by mathematically calculating, for each of the various hypotheses, the value that the probability equals, as stated by one or more of the expert techniques, algorithms, and/or methods described elsewhere in this disclosure, using the relevant genetic data as input.

Once the probabilities of the different hypotheses are estimated, as determined by a plurality of techniques, they may be combined. This may entail, for each hypothesis, multiplying the probabilities as determined by each technique. The product of the probabilities of the hypotheses may be normalized. Note that one ploidy hypothesis refers to one possible ploidy state for a chromosome.

The process of 'combining probabilities', also called 'combining hypotheses', or combining the results of expert techniques, is a concept that should be familiar to one skilled in the art of linear algebra. One possible way to combine probabilities is as follows: When an expert technique is used to evaluate a set of hypotheses given a set of genetic data, the output of the method is a set of probabilities that are associated, in a one-to-one fashion, with each hypothesis in the set of hypotheses. When a set of probabilities that were determined by a first expert technique, each of which are associated with one of the hypotheses in the set, are combined with a set of probabilities that were determined by a second expert technique, each of which are associated with the same set of hypotheses, then the two sets of probabilities are multiplied. This means that, for each hypothesis in the set, the two probabilities that are associated with that hypothesis, as determined by the two expert methods, are multiplied together, and the corresponding product is the output probability. This process may be expanded to any number of expert techniques. If only one expert technique is used, then the output probabilities are the same as the input probabilities. If more than two expert techniques are used, then the relevant probabilities may be multiplied at the same time. The products may be normalized so that the probabilities of the hypotheses in the set of hypotheses sum to 100%.

In some embodiments, if the combined probabilities for a given hypothesis are greater than the combined probabilities for any of the other hypotheses, then it may be considered that that hypothesis is determined to be the most likely. In some embodiments, a hypothesis may be determined to be the most likely, and the ploidy state, or other genetic state, may be called if the normalized probability is greater than a threshold. In one embodiment, this may mean that the number and identity of the chromosomes that are associated with that hypothesis may be called as the ploidy state. In one embodiment, this may mean that the identity of the alleles that are associated with that hypothesis may be called as the allelic state. In some embodiments, the threshold may be between about 50% and about 80%. In some embodiments the threshold may be between about 80% and about 90%. In some embodiments the threshold may be between about 90% and about 95%. In some embodiments the threshold may be between about 95% and about 99%. In some embodiments the threshold may be between about 99% and about 99.9%. In some embodiments the threshold may be above about 99.9%.

Some Embodiments

In an embodiment of the present disclosure, a method for determining a ploidy state of at least one chromosome in a target individual includes obtaining genetic data from the target individual and from one or more related individuals; creating a set of at least one ploidy state hypothesis for each of the chromosomes of the target individual; using one or more expert techniques to determine a statistical probability for each ploidy state hypothesis in the set, for each expert technique used, given the obtained genetic data; combining, for each ploidy state hypothesis, the statistical probabilities as determined by the one or more expert techniques; and determining the ploidy state for each of the chromosomes in the target individual based on the combined statistical probabilities of each of the ploidy state hypotheses.

In an embodiment, determining the ploidy state of each of the chromosomes in the target individual can be performed in the context of in vitro fertilization, and where the target individual is an embryo. In an embodiment, determining the ploidy state of each of the chromosomes in the target individual can be performed in the context of non-invasive prenatal diagnosis, and where the target individual is a fetus. Determining the ploidy state of each of the chromosomes in the target individual can be performed in the context of screening for a chromosomal condition selected from the group including, but not limited to, euploidy, nullsomy, monosomy, uniparental disomy, trisomy, matching trisomy, unmatching trisomy, tetrasomy, other aneuploidy, unbalanced translocation, deletions, insertions, mosaicism, and combinations thereof. In an embodiment, determining the ploidy state of each of the chromosomes in the target individual can be carried out for a plurality of embryos and is used to select at least one embryo for insertion into a uterus. A clinical decision is made after determining the ploidy state of each of the chromosomes in the target individual.

In some embodiments of the present disclosure, a method for determining the ploidy state of one or more chromosome in a target individual may include the following steps:

First, genetic data from the target individual and from one or more related individuals may be obtained. In an embodiment, the related individuals include both parents of the target individual. In an embodiment, the related individuals include siblings of the target individual. This genetic data for individuals may be obtained in a number of ways including, but not limited to, it may be output measurements from a genotyping platform; it may be sequence data measured on the genetic material of the individual; it may be genetic data in silico; it may be output data from an informatics method designed to clean genetic data, or it may be from other sources. The genetic material used for measurements may be amplified by a number of techniques known in the art.

The target individual's genetic data can be measured using tools and or techniques taken from a group including, but not limited to, MOLECULAR INVERSION PROBES (MIP), Genotyping Microarrays, the TAQMAN SNP Genotyping Assay, the ILLUMINA Genotyping System, other genotyping assays, fluorescent in-situ hybridization (FISH), sequencing, other high through-put genotyping platforms, and combinations thereof. The target individual's genetic data can be measured by analyzing substances taken from a group including, but not limited to, one or more diploid cells from the target individual, one or more haploid cells from the target individual, one or more blastomeres from the target individual, extra-cellular genetic material found on the target individual, extra-cellular genetic material from the target individual found in maternal blood, cells from the target individual found in maternal blood, genetic material known to have originated from the target individual, and combinations thereof. The related individual's genetic data can be measured by analyzing substances taken from a group including, but not limited to, the related individual's bulk diploid tissue, one or more diploid cells from the related individual, one or more haploid cells taken from the related individual, one or more embryos created from (a) gamete(s) from the related individual, one or more blastomeres taken from such an embryo, extra-cellular genetic material found on the related individual, genetic material known to have originated from the related individual, and combinations thereof.

Second, a set of at least one ploidy state hypothesis may be created for each of the chromosomes of the target individual. Each of the ploidy state hypotheses may refer to one possible ploidy state of the chromosome of the target individual. The set of hypotheses may include all of the possible ploidy states that the chromosome of the target individual may be expected to have.

Third, using one or more of the expert techniques discussed in this disclosure, a statistical probability may be determined for each ploidy state hypothesis in the set. In some embodiments, the expert technique may involve an algorithm operating on the obtained genetic data, and the output may be a determined statistical probability for each of the hypotheses under consideration. In an embodiment, at least one of the expert techniques uses phased parental allele call data, that is, it uses, as input, allelic data from the parents of the target individual where the haplotypes of the allelic data have been determined. In an embodiment, at least one of the expert techniques is specific to a sex chromosome. The set of determined probabilities may correspond to the set of hypotheses. In an embodiment, the statistical probability for each of the ploidy state hypotheses may involve plotting a cumulative distribution function curve for one or more parental contexts. In an embodiment, determining the statistical probability for each of the ploidy state hypotheses may involve comparing the intensities of genotyping output data, averaged over a set of alleles, to expected intenities. The mathematics underlying the various expert techniques is described elsewhere in this disclosure.

Fourth, the set of determined probabilities may then be combined. This may entail, for each hypothesis, multiplying the probabilities as determined by each technique, and it also may involve normalizing the hypotheses. In some embodiments, the probabilities may be combined under the assumption that they are independent. The set of the products of the probabilities for each hypothesis in the set of hypotheses is then output as the combined probabilities of the hypotheses.

Lastly, the ploidy state for the target individual is determined to be the ploidy state that is associated with the hypothesis whose probability is the greatest. In some cases, one hypothesis will have a normalized, combined probability greater than 90%. Each hypothesis is associated with one ploidy state, and the ploidy state associated with the hypothesis whose normalized, combined probability is greater than 90%, or some other threshold value, may be chosen as the determined ploidy state.

In another embodiment of the present disclosure, a method for determining an allelic state in a set of alleles from a target individual, from one or both of the target individual's parents, and possibly from one or more related individuals, includes obtaining genetic data from the target individual, and from the one or both parents, and from any related individuals; creating a set of at least one allelic hypothesis for the target individual, and for the one or both parents, and optionally for the one or more related individuals, where the hypotheses describe possible allelic states in the set of alleles; determining a statistical probability for each allelic hypothesis in the set of hypotheses given the obtained genetic data; and determining the allelic state for each of the alleles in the set of alleles for the target individual, and for the one or both parents, and optionally for the one or more related individuals, based on the statistical probabilities of each of the allelic hypotheses. In an embodiment, the method takes into account a possibility of DNA crossovers that may occur during meiosis. In an embodiment, the method can be performed alongside or in conjunction with a method that determines a number of copies of a given chromosome segment present in the one or more target individuals, and where both methods use a same cell, or group of cells, from the one or more target individuals as a source of genetic data.

In an embodiment, allelic state determination can be performed in the context of in vitro fertilization, and where at least one of the target individuals is an embryo. In an embodiment, allelic state determination can be performed wherein at least one of the target individuals is an embryo, and wherein determining the allelic state in the set of alleles of the one or more target individuals is performed to select at least one embryo for transfer in the context of IVF, and where the target individuals are selected from the group including, but not limited to, one or more embryos that are from the same parents, one or more sperm from the father, and combinations thereof. In an embodiment, allelic state determination can be performed in the context of non-invasive prenatal diagnosis, and where at least one of the target individuals is a fetus. In an embodiment, determining the allelic state in the set of alleles of the one or more target individuals may include a phased genotype at a set of alleles for those individuals. A clinical decision can be made after determining the allelic state in the set of alleles of the one of more target individuals.

In some embodiments of the present disclosure, a method for determining the allelic data of one or more target individuals, and one or both of the target individuals' parents, at a set of alleles, may include the following steps:

First, genetic data from the target individual(s), from one or both of the parents, and from zero or more related individuals, may be obtained. This genetic data for individuals may be obtained in a number of ways including, but not limited to, output measurements from a genotyping platform; it may be sequence data measured on the genetic material of the individual; it may be genetic data in silico; it may be output data from an informatics method designed to clean genetic data, or it may be from other sources. In an embodiment, the obtained genetic data may include single nucleotide polymorphisms measured from a genotyping array. In an embodiment, the obtained genetic data may include DNA sequence data, that is, the measured genetic sequence representing the primary structure of the DNA of the individual. The genetic material used for measurements may be amplified by a number of techniques known in the art. In one embodiment, the target individuals are all siblings. In one embodiment, one or more of the genetic measurements of the target individuals were made on single cells. In an embodiment, platform response models can be used to determine a likelihood of a true genotype given observed genetic measurements and a characteristic measurement bias of the genotyping technique.

The target individual's genetic data can be measured using tools and or techniques taken from a group including, but not limited to, MOLECULAR INVERSION PROBES (MIP), Genotyping Microarrays, the TAQMAN SNP Genotyping Assay, the ILLUMINA Genotyping System, other genotyping assays, fluorescent in-situ hybridization (FISH), sequencing, other high through-put genotyping platforms, and combinations thereof. The target individual's genetic data can be measured by analyzing substances taken from a group including, but not limited to, one or more diploid cells from the target individual, one or more haploid cells from the target individual, one or more blastomeres from the target individual, extra-cellular genetic material found on the target individual, extra-cellular genetic material from the target individual found in maternal blood, cells from the target individual found in maternal blood, genetic material known to have originated from the target individual, and combinations thereof. The related individual's genetic data can be measured by analyzing substances taken from a group including, but not limited to, the related individual's bulk diploid tissue, one or more diploid cells from the related individual, one or more haploid cells taken from the related individual, one or more embryos created from (a) gamete(s) from the related individual, one or more blastomeres taken from such an embryo, extra-cellular genetic material found on the related individual, genetic material known to have originated from the related individual, and combinations thereof.

Second, a set of a plurality of allelic hypothesis may be created for the set of alleles, for each of the individuals. Each of the allelic hypotheses may refer to a possible identity for each of the alleles over the set of alleles for that individual. In one embodiment, the identity of the alleles of a target individual may include the origin of the allele, namely, the parent from which the allele genetically originated, and the specific chromosome from which the allele genetically originated. The set of hypotheses may include all of the possible allelic states that the target individual may be expected to have within that set of alleles.

Lastly, a statistical probability for each of the allelic hypotheses may be determined given the obtained genetic data. The determination of the probability of a given hypothesis may be done using any of the algorithms described in this disclosure, specifically those in the allele calling section. The set of allelic hypotheses for an individual may include all of the possible allelic states of that individual, over the set of alleles. Those hypotheses that match more closely to the noisy measured genetic data of the target individual are more likely to be correct. The hypothesis that corresponds exactly to the actual genetic data of the target individual will most likely be determined to have a very high probability. The allelic state may be determined to be the allelic state that corresponds with the hypothesis that is determined to have the highest probability. In some embodiments, the allelic state may be determined for various subsets of the set of alleles.

Parental Support

Some embodiments of the present disclosure may use the informatics based PARENTAL SUPPORT™ (PS) method. In some embodiments, the PARENTAL SUPPORT™ method is a collection of methods that may be used to determine the genetic data, with high accuracy, of one or a small number of cells, specifically to determine disease-related alleles, other alleles of interest, and/or the ploidy state of the cell(s).

The PARENTAL SUPPORT™ method makes use of known parental genetic data, i.e. haplotypic and/or diploid genetic data of the mother and/or the father, together with the knowledge of the mechanism of meiosis and the imperfect measurement of the target DNA, and possible of one or more related individuals, in order to reconstruct, in silico, the genotype at a plurality of alleles, and/or the ploidy state of an embryo or of any target cell(s), and the target DNA at the location of key loci with a high degree of confidence. The PARENTAL SUPPORT™ method can reconstruct not only single-nucleotide polymorphisms that were measured poorly, but also insertions and deletions, and SNPs or whole regions of DNA that were not measured at all. Furthermore, the PARENTAL SUPPORT™ method can both measure multiple disease-linked loci as well as screen for aneuploidy, from a single cell. In some embodiments, the PARENTAL SUPPORT™ method may be used to characterize one or more cells from embryos biopsied during an IVF cycle to determine the genetic condition of the one or more cells.

The PARENTAL SUPPORT™ method allows the cleaning of noisy genetic data. This may be done by inferring the correct genetic alleles in the target genome (embryo) using the genotype of related individuals (parents) as a reference. PARENTAL SUPPORT™ may be particularly relevant where only a small quantity of genetic material is available (e.g. PGD) and where direct measurements of the genotypes are inherently noisy due to the limited amounts of genetic material. The PARENTAL SUPPORT™ method is able to reconstruct highly accurate ordered diploid allele sequences on the embryo, together with copy number of chromosomes segments, even though the conventional, unordered diploid measurements may be characterized by high rates of allele dropouts, drop-ins, variable amplification biases and other errors. The method may employ both an underlying genetic model and an underlying model of measurement error. The genetic model may determine both allele probabilities at each SNP and crossover probabilities between SNPs. Allele probabilities may be modeled at each SNP based on data obtained from the parents and model crossover probabilities between SNPs based on data obtained from the HapMap database, as developed by the International HapMap Project. Given the proper underlying genetic model and measurement error model, maximum a posteriori (MAP) estimation may be used, with modifications for computationally efficiency, to estimate the correct, ordered allele values at each SNP in the embryo.

One aspect of the PARENTAL SUPPORT™ technology is a chromosome copy number calling algorithm that in some embodiments uses parental genotype contexts. To call the chromosome copy number, the algorithm may use the phenomenon of locus dropout (LDO) combined with distributions of expected embryonic genotypes. During whole genome amplification, LDO necessarily occurs. LDO rate is concordant with the copy number of the genetic material from which it is derived, i.e., fewer chromosome copies result in higher LDO, and vice versa. As such, it follows that loci with certain contexts of parental genotypes behave in a characteristic fashion in the embryo, related to the probability of allelic contributions to the embryo. For example, if both parents have homozygous BB states, then the embryo should never have AB or AA states. In this case, measurements on the A detection channel are expected to have a distribution determined by background noise and various interference signals, but no valid genotypes. Conversely, if both parents have homozygous AA states, then the embryo should never have AB or BB states, and measurements on the A channel are expected to have the maximum intensity possible given the rate of LDO in a particular whole genome amplification. When the underlying copy number state of the embryo differs from disomy, loci corresponding to the specific parental contexts behave in a predictable fashion, based on the additional allelic content that is contributed by, or is missing from, one of the parents. This allows the ploidy state at each chromosome, or chromosome segment, to be determined. The details of one embodiment of this method are described elsewhere in this disclosure.

Copy Number Calling Using Parental Contexts

The concept of parental contexts may be useful in the context of copy number calling (also referred to as 'ploidy determination'). When genotyped, all of the SNPs within a first parental context may be expected to statistically behave the same way when measured for a given ploidy state. In contrast, some sets of SNPs from a second parental context may be expected to statistically behave differently from those in the first parental context in certain circumstances, such as for certain ploidy states, and the difference in behavior may be characteristic of one or a set of particular ploidy states. There are many statistical techniques that could be used to analyze the measured responses at the various loci within the various parental contexts. In some embodiments of the present disclosure, statistical techniques may be used that output probabilities for each of the hypotheses. In some embodiments of the present disclosure, statistical techniques may be used that output probabilities for each of the hypotheses along with confidences in the estimated probabilities. Some techniques, when used individually, may not be adequate to determine the ploidy state of a given chromosome with a given level of confidence.

The key to one aspect of the present disclosure is the fact that some specialized expert techniques are particularly good at confirming or eliminating from contention certain ploidy states or sets of ploidy states, but may not be good at correctly determining the ploidy state when used alone. This is in contrast to some expert techniques that may be relatively good at differentiating most or all ploidy states from one another, but not with as high confidence as some specialized expert techniques may be at differentiating one particular subset of ploidy states. Some methods use one generalized technique to determine the ploidy state. However, the combination of the appropriate set of specialized expert techniques may be more accurate in making ploidy determinations than using one generalized expert technique.

For example, one expert technique may be able to determine whether or not a target is monosomic with very high confidence, a second expert technique may be able to determine whether or not a target is trisomic or tetrasomic with very high confidence, and a third technique may be able to detect uniparental disomy with very high confidence. None of these techniques may be able to make an accurate ploidy determination alone, but when these three specialized expert techniques are used in combination, they may be able to determine the ploidy call with greater accuracy than when using one expert technique that can differentiate all of the ploidy states reasonably well. In some embodiments of the present disclosure, one may combine the output probabilities from multiple techniques to arrive at a ploidy state determination with high confidence. In some embodiments of the present disclosure, the probabilities that each of the techniques predicts for a given hypothesis may be multiplied together, and that product may be taken to be the combined probability for that hypothesis. The ploidy state(s) associated with the hypothesis that has the greatest combined probability may be called as the correct ploidy state. If the set of expert techniques is chosen appropriately, then the combined product of the probabilities may allow the ploidy state to be determined more accurately than a single technique. In some embodiments of the inversion, the probabilities of the hypotheses from more than one technique may be multiplied, for example using linear algebra, and renormalized, to give the combined probabilities. In one embodiment, the confidences of the probabilities may be combined in a manner similar to the probabilities. In one embodiment of the present disclosure, the probabilities of the hypotheses may be combined under the assumption that they are independent. In some embodiments of the present disclosure, the output of one or more techniques may be used as input for other techniques. In one embodiment of the present disclosure, the ploidy call, made using one or a set of expert techniques, may be used to determine the appropriate input for the allele calling technique. In one embodiment of the present disclosure, the phased, cleaned genetic data output from the allele calling technique may be used as input for one or a set of expert ploidy calling techniques. In some embodiments of the present disclosure, the use of the various techniques may be iterated.

In some embodiments of the present disclosure, the ploidy state may be called with a confidence of greater than about 80%. In some embodiments of the present disclosure, the ploidy state may be called with a confidence of greater than about 90%. In some embodiments of the present disclosure, the ploidy state may be called with a confidence of greater than about 95%. In some embodiments of the present disclosure, the ploidy state may be called with a confidence of greater than about 99%. In some embodiments of the present disclosure, the ploidy state may be called with a confidence of greater than about 99.9%. In some embodiments of the present disclosure, one or a set of alleles may be called with a confidence of greater than about 80%. In some embodiments of the present disclosure, the allele(s) may be called with a confidence of greater than about 90%. In some embodiments of the present disclosure, the allele(s) may be called with a confidence of greater than about 95%. In some embodiments of the present disclosure, the allele(s) may be called with a confidence of greater than about 99%. In some embodiments of the present disclosure, the allele(s) may be called with a confidence of greater than about 99.9%. In some embodiments of the present disclosure, the output allele call data is phased, differentiating the genetic data from the two homologous chromosomes. In some embodiments of the present disclosure, phased allele call data is output for all of the individuals.

Below is a description of several statistical techniques that may be used in the determination of the ploidy state. This list is not meant to be an exhaustive list of possible expert techniques. It is possible to use any statistical technique that is able to place probabilities and/or confidences on the set of ploidy state hypotheses of a target. Any of the following techniques may be combined, or they may be combined with other techniques not discussed in this disclosure.

Permutation Technique

The LDO rate is concordant with the copy number of the genetic material from which it is derived, that is, fewer chromosome copies result in higher LDO, and vice versa. It follows that loci with certain contexts of parental genotypes behave in a characteristic fashion in the embryo, related to the probability of allelic contributions to the embryo. In one embodiment of the present disclosure, called the "permutation technique", it is possible to use the characteristic behavior of loci in the various parental contexts to infer the ploidy state of those loci. Specifically, this technique involves comparing the relationship between observed distributions of allele measurement data for different parent contexts, and determining which ploidy state matched the observed set of relationships between the distributions. This technique is particularly useful in determining the number of homologous chromosomes present in the sample. By plotting a cumulative distribution function (CDF) curve for each of the parental contexts, one may observe that various contexts cluster together. Note that a CDF curve is only one way to visualize and compare the observed distributions of the allele measurements data. For example, FIG. 1 shows a CDF curve for a disomic chromosome. In particular, FIG. 1 shows how allele measurement data from certain contexts of parental genotypes (MotherFather) behave in a characteristic fashion in the embryo, related to the probability of allelic contributions to the embryo. The nine parental contexts group into five clusters when the chromosome in question is disomic. On the CDF curve plot, the independent variable, along the x-axis, is the channel response, and the dependent variable, along the y-axis, is the percentage of alleles within that context whose channel response is below a threshold value.

Figure 2A:
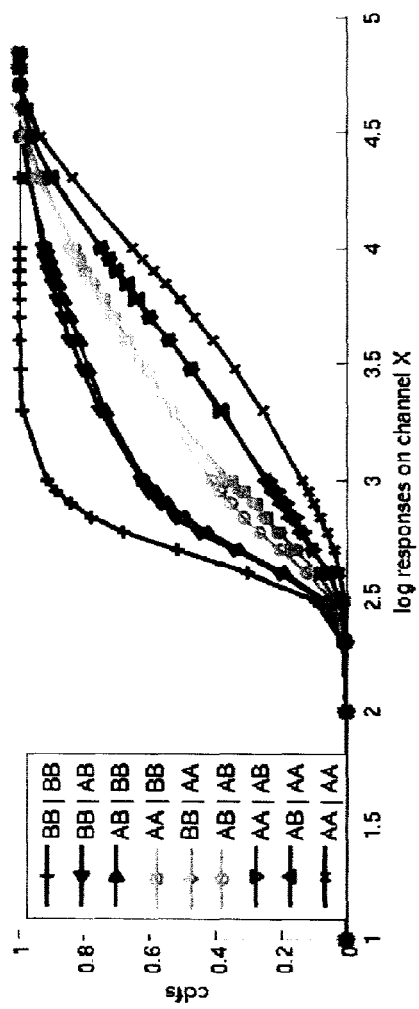
FIGS. 2A-2D show cumulative distribution function curves for chromosomes with varying ploidy states.
Figure 2B:
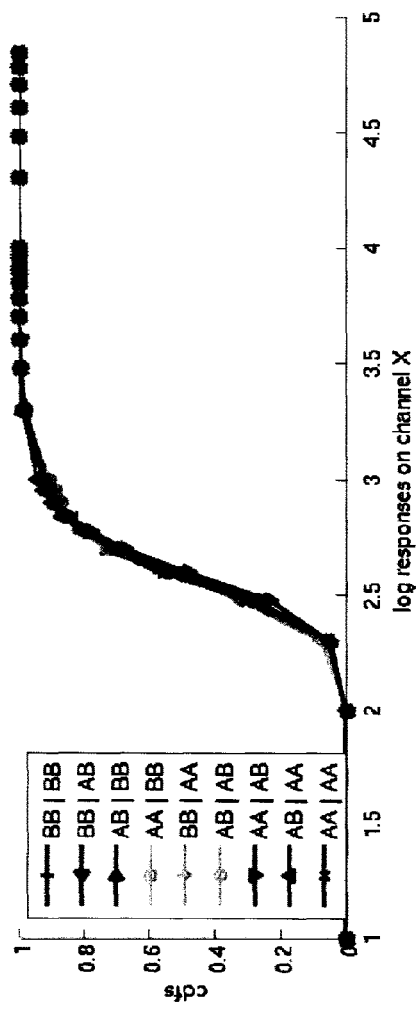
Figure 2C:
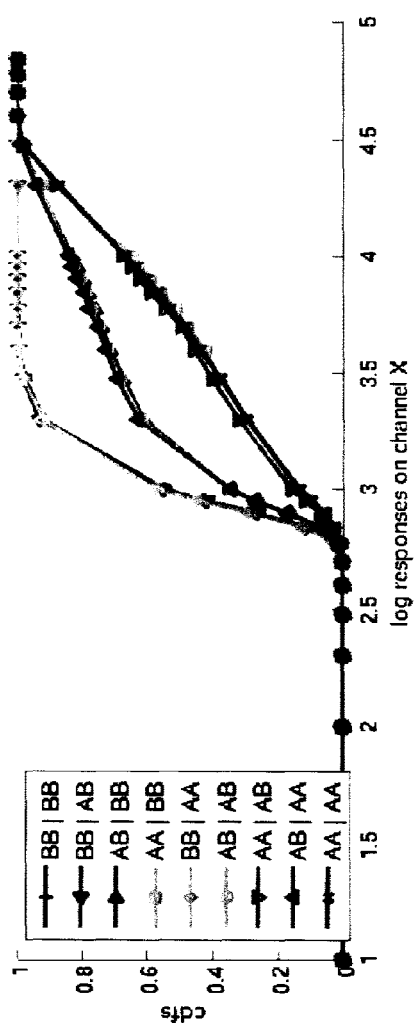
Figure 2D:
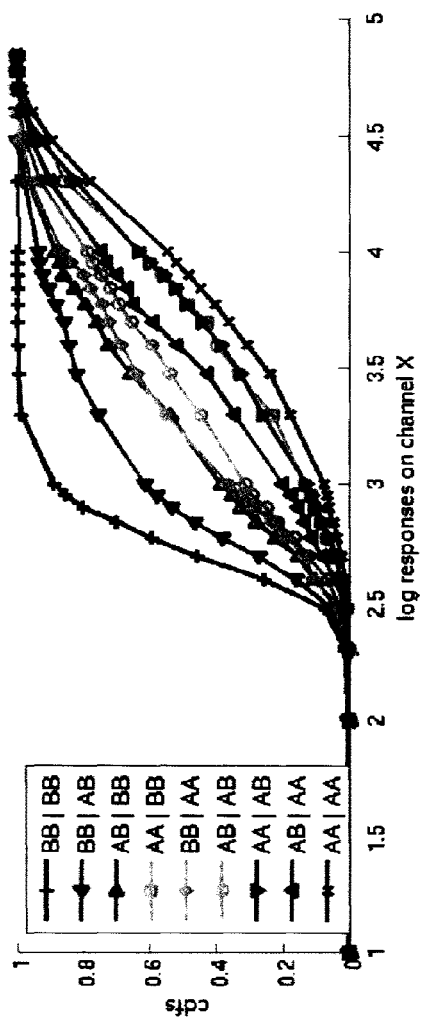

For example, if both parents have homozygous BB states, then the embryo should never have AB or AA states. In this case, measurements on the A detection channel will likely have a distribution determined by background noise and various interference signals, but no valid genotypes. Conversely, if both parents have homozygous AA states, then the embryo should never have AB or BB states, and measurements on the A channel will likely have the maximum intensity possible given the rate of LDO in a particular whole genome amplification. When the underlying copy number state of the embryo differs from disomy, loci corresponding to the specific parental contexts behave in a predictable fashion, based on the additional allelic content that is contributed or is missing from one of the parents. Cumulative density function plots of microarray probe intensity on a detection channel, segregated by parental genotype context, illustrate the concept (see FIG. 2). Specifically, FIGS. 2A-2D show how the relation between the context curves on a CDF plot changes predictably with a change in the chromosome copy number. FIG. 2A shows a cumulative distribution function curve for a disomic chromosome, FIG. 2B shows a cumulative distribution function curve for a nullisomic chromosome, FIG. 2C shows a cumulative distribution function curve for a monosomic chromosome, and FIG. 2D shows a cumulative distribution function curve for a maternal trisomic chromosome.

Each context is represented as $M_1M_2|F_1F_2$, where $M_1$ and $M_2$ are the maternal alleles, and $F_1$ and $F_2$ are the paternal alleles. There are nine possible parental contexts (see FIGS. 2A-2D legend), which, in a disomic chromosome, form five clusters on the CDF plot. In the case of nullosomies, all of the parental context curves cluster with background on the CDF plot. In the case of monosomy, one may expect to see only three context curve clusters, because the removal of one parental context results in only three possible embryonic outcomes: homozygous AA, heterozygous AB, and homozygous BB. One may expect trisomy also to have a distinct CDF-curve topology such that there are seven clusters, caused by extra alleles on a single detection channel and from only one parent.

One set of expected canonical topologies is illustrated in FIGS. 2A-2D, for which the ploidy state may be called by visual inspection of the plots. In some cases, the data from a sample may not be as easy to interpret as the data shown in FIGS. 2A-2D. Many factors may impact data clarity, including: degraded DNA of blastomeres which causes signals with very low signal-to noise ratio; partial ploidy errors which are often encountered during IVF such as translocations; and chromosome-specific and chromosome-segment specific amplification biases possibly caused by the physical positions of the chromosomes in the nucleus or epigenetic phenomenon such as different methylation levels and proteins structures around the chromosomes. These and an assortment of other phenomenon may differentially affect each chromosome of a homologous pair in which case they are difficult to distinguish from ploidy states. In one embodiment of the present disclosure, to accommodate these various affects, a statistical algorithm may be used to analyze data such as that illustrated in FIGS. 2A-2D and generate a ploidy determination together with a confidence in the correctness of that determination.

In one embodiment of the present disclosure, in order to be robust to the differences that may exist between one sample and another, or between cell line samples and blastomeres, the algorithm may be non parametric and does not depend on expected values of statistics or thresholds which are trained on certain samples and applied to others. In one embodiment of the present disclosure, the algorithm uses quantile-rank statistics (a non-parametric permutation method), which first computes the rank of the CDF curve of each context at an intensity at which the background context is within about 80% of a density of about 1. In another embodiment, the algorithm may compute the rank of the CDF curve of each context at an intensity at which the background context is within about 90% of a density of about 1. In another embodiment, the algorithm may compute the rank of the CDF curve of each context at an intensity at which the background context is within about 95% of a density of about 1. Then, the algorithm compares the rank of the data to the expected rank given various ploidy states. For example, if the AB|BB context has the same rank as the BB|AA context, this differs from the expectation under disomy, but is consistent with maternal trisomy. One then may examine the distribution of the data for each sample to determine the probability that two CDF curves could have swapped ranked by random chance, and then use this information, combined with the rank statistics, to determine copy number calls and calculate explicit confidences. The result of this statistical technique is a highly accurate diagnosis of chromosome copy number, combined with an explicit confidence in each call.

Since the permutation technique's copy number call for a given chromosome is independent of all other chromosomes, without loss of generality it is possible to focus on a single given chromosome. For a given maternal genotype gM and paternal genotype gF one may use gM|gF to denote the parental context, e.g. AB|BB refers to the SNPs where the mother's genotype is AB and the father's genotype is BB.

For a given context gM|gF, let $X_{gM|gF}$ denote the set of x-channel responses for all SNPs in the context gM|gF. Similarly, one may use $Y_{gM|gF}$ to denote the set of y-channel responses. Furthermore, for a given positive number C, one may define $I_{\{x \leq c\}} n_{gM|gF}^x(c) = \Sigma_{x \in X_{gM|gF}} I_{\{x \leq c\}}$ and $n_{gM|gF}^y(c) = \Sigma_{y \in Y_{gM|gF}} I_{\{y \leq c\}}$ One may also use $N_{gM|gF}$ to denote the number of SNPs in the context gM|gF. It is possible to define $$\hat{p}_{gM|gF}^x(c) = (n_{gM|gF}^x(c))/(N_{gM|gF}) \text{ and } \hat{p}_{gM|gF}^y(c) = (n_{gM|gF}^y(c))/N_{gM|gF})$$

One can think of $\hat{p}_{gM|gF}^x(c)$, $\hat{p}_{gM|gF}^y(c)$ as the value of the empirical CDF of the x-channel, y-channel, response of context gM|gF at the point c. One may denote the true CDFs as $p_{gM|gF}^x(c)$, and $p_{gM|gF}^y(c)$ The Algorithm The main idea behind the algorithm is that for a given positive integer c, the order $p_{AA|AA}^x(c)$, $p_{AB|AA}^x(c)$, $p_{BB|AA}^x(c)$, $p_{AA|AB}^x(c)$, $p_{AB|AB}^x(c)$, $p_{BB|AB}^x(c)$, $p_{AA|BB}^x(c)$, $p_{AB|BB}^x(c)$, and $p_{BB|BB}^x(c)$, will vary based on the chromosome copy number. The same holds for the y-channel. In one embodiment of the present disclosure, one may use this order to determine chromosome copy number. Since the x-channel and y-channel are treated independently, going forward this discussion will focus on only the x-channel.

Calculations

The first step is to pick a value for c that maximizes distinguishability between the contexts, that is, the value for c which maximizes the difference between the two extreme contexts, AA|AA and BB|BB. More precisely one may define:

$$c_x = \underset{c \in \{0, 100, \ldots, 66000\}}{\mathrm{argmax}} \hat{p}_{BB|BB}^x(c) - \hat{p}_{AA|AA}^x(c) \text{ and}$$

$$e_x = \hat{p}_{BB|BB}^x(c_x) - \hat{p}_{AA|AA}^x(c_x), \text{ and also}$$

$$c_y = \underset{c \in \{0, 100, \ldots, 66000\}}{\mathrm{argmax}} \hat{p}_{BB|BB}^y(c) - \hat{p}_{AA|AA}^y(c) \text{ and}$$

$$e_x = \hat{p}_{BB|BB}^y(c_y) - \hat{p}_{AA|AA}^y(c_y)$$

This discussion will therefore use $c_x$ as the sample point and make all order comparisons with regards to $\hat{p}_{AA|AA}^x(c_x)$, $\hat{p}_{AB|AA}^x(c_x)$, $\hat{p}_{BB|AA}^x(c_x)$, $\hat{p}_{AA|AB}^x(c_x)$, $\hat{p}_{AB|AB}^x(c_x)$, $\hat{p}_{BB|AB}^x(c_x)$, $\hat{p}_{AA|BB}^x(c_x)$, $\hat{p}_{AB|BB}^x(c_x)$, $\hat{p}_{BB|BB}^x(c_x)$. From here forward the discussion will drop the dependence on $c_x$. In order to assign a confidence to the chromosome copy number call, it is important to determine a variance for each $p_{gM|gF}{}^x$. This may be done by making use of a binomial model. In particular, one may observe that each $n_{gM|gF}{}^x$ is the sum of I.I.D. Bernoulli random variables, and hence the normalized sum, has standard deviation $$\sigma_{gM|gF}^x = \sqrt{\frac{p_{gM|gF}^x(1-p_{gM|gF}^x)}{N_{gM|gF}}}$$

Confidence Calculation

Described herein is a method to calculate a confidence on a given copy number hypothesis. Each hypothesis has a set of valid permutation of

| | | |
|---|---|---|
| $\hat{p}_{AA|AA}^x \approx p_{AA|AA}^x$ | $\hat{p}_{AA|AB}^x \approx p_{AA|AB}^x$ | $\hat{p}_{BB|AB}^x \approx p_{BB|AB}^x$ |
| $\hat{p}_{AB|AA}^x \approx p_{AB|AA}^x$ | $\hat{p}_{AB|AB}^x \approx p_{AB|AB}^x$ | $\hat{p}_{AA|BB}^x \approx p_{AA|BB}^x$ |
| $\hat{p}_{BB|AA}^x \approx p_{AB|AA}^x$ | $\hat{p}_{BB|AB}^x \approx p_{BB|AB}^x$ | $\hat{p}_{AB|BB}^x \approx p_{AB|BB}^x$ |

For example, a hypothesis of disomy would have the following set of valid permutations:

| | | |
|---|---|---|
| $\hat{p}_{AA|AA}^x \approx p_{AA|AA}^x$: 1 | $\hat{p}_{AA|AB}^x \approx p_{AA|AB}^x$: 2 | $\hat{p}_{AA|BB}^x \approx p_{AA|BB}^x$: 3 |
| $\hat{p}_{AB|AA}^x \approx p_{AB|AA}^x$: 2 | $\hat{p}_{AB|AB}^x \approx p_{AB|AB}^x$: 3 | $\hat{p}_{AB|BB}^x \approx p_{AB|BB}^x$: 4 |
| $\hat{p}_{BB|AA}^x \approx p_{AB|AA}^x$: 3 | $\hat{p}_{BB|AB}^x \approx p_{BB|AB}^x$: 4 | $\hat{p}_{BB|BB}^x \approx p_{BB|BB}^x$: 5 | where two entries are given the same value if their relative order is not specified under the hypothesis. Hence there are 12 valid permutations for disomy. Confidence for a given hypothesis is calculated by finding the valid permutation which matches the observed data. This is done by ordering the elements of the invariant groups, groups which have the same order numbers, with regards to their observed statistic.

For example, given that the following order is observed:

$$\begin{bmatrix} \hat{p}_{AA|AA}^x \\ \hat{p}_{AB|AA}^x \\ \hat{p}_{BB|AA}^x \\ \hat{p}_{AA|AB}^x \\ \hat{p}_{AB|AB}^x \\ \hat{p}_{BB|AB}^x \\ \hat{p}_{AA|BB}^x \\ \hat{p}_{AB|BB}^x \\ \hat{p}_{BB|BB}^x \end{bmatrix}$$

the permutation that is consistent with disomy and matches the data is $$\begin{bmatrix} p_{AA|AA}^x \\ p_{AB|AA}^x \\ p_{BB|AA}^x \\ p_{AA|AB}^x \\ p_{AB|AB}^x \\ p_{BB|AB}^x \\ p_{AA|BB}^x \\ p_{AB|BB}^x \\ p_{BB|BB}^x \end{bmatrix}$$

One may then calculate the probability of the observed x-channel data given a hypothesis of disomy as $\Pr\{\text{x-data}|H_{1,1}\} = \Pr\{\text{x-data best match order}\}$ $$\approx^{(a)} \Pr\{\hat{p}_{AA|AA}^x, \hat{p}_{AB|AA}^x | p_{AA|AA}^x \leq p_{AB|AA}^x\}$$

$$\Pr\{\hat{p}_{AB|AA}^x, \hat{p}_{AA|AB}^x | p_{AB|AA}^x \leq p_{AA|AB}^x\}$$

$$\Pr\{\hat{p}_{AA|AB}^x, \hat{p}_{BB|AA}^x | p_{AA|AB}^x \leq p_{BB|AA}^x\}$$

$$\Pr\{\hat{p}_{BB|AA}^x, \hat{p}_{AA|BB}^x | p_{BB|AA}^x \leq p_{AA|BB}^x\}$$

$$\Pr\{\hat{p}_{AA|BB}^x, \hat{p}_{AB|AB}^x | p_{AA|BB}^x \leq p_{AB|AB}^x\}$$

$$\Pr\{\hat{p}_{AB|AB}^x, \hat{p}_{BB|AB}^x | p_{AB|AB}^x \leq p_{BB|AB}^x\}$$

$$\Pr\{\hat{p}_{BB|AB}^x, \hat{p}_{AB|BB}^x | p_{BB|AB}^x \leq p_{AB|BB}^x\}$$

$$\Pr\{\hat{p}_{AB|BB}^x, \hat{p}_{BB|BB}^x | p_{AB|BB}^x \leq p_{BB|BB}^x\}$$

In this case, the approximation (a) is made in order to make the probability computable. Finally, for any two contexts gM1|gF1 and gM2|gF one may calculate:

$$\Pr\{\hat{p}_{gM1|gF1}^x, \hat{p}_{gM2|gF2}^x | p_{gM1|gF1}^x \leq p_{gM2|gF2}^x\} =$$

$$\frac{1}{\Pr\{p_{gM1|gF1}^x \leq p_{gM2|gF2}^x\}} \Pr\{\hat{p}_{gM1|gF1}^x, \hat{p}_{gM2|gF2}^x, p_{gM1|gF1}^x \leq p_{gM2|gF2}^x\} \stackrel{(a)}{=}$$

$$\frac{1}{\Pr\{p_{gM1|gF1}^x \leq p_{gM2|gF2}^x\}} \cdot \int_{p_{gM1|gF1}^x \leq p_{gM2|gF2}^x} \Pr\{\hat{p}_{gM1|gF1}^x,$$

$$\hat{p}_{gM2|gF2}^x, p_{gM1|gF1}^x, p_{gM2|gF2}^x\} dp_{gM1|gF1}^x dp_{gM2|gF2}^x \stackrel{(b)}{=}$$

$$\alpha \int_{p_{gM1|gF1}^x \leq p_{gM2|gF2}^x} \Pr\{\hat{p}_{gM1|gF1}^x, \hat{p}_{gM2|gF2}^x | p_{gM1|gF1}^x, p_{gM2|gF2}^x\}$$

$$dp_{gM1|gF1}^x dp_{gM2|gF2}^x \stackrel{(c)}{=} \alpha \int_{p_{gM1|gF1}^x \leq p_{gM2|gF2}^x} f p_{gM1|gF1}^x,$$

$$\sigma_{gM1|gF1}^x(\hat{p}_{gM1|gF1}^x) f p_{gM2|gF2}^x, \sigma_{gM2|gF2}^x(\hat{p}_{gM2|gF2}^x)$$

$$dp_{gM1|gF1}^x dp_{gM2|gF2}^x =$$

$$\alpha \int_{p_{gM1|gF1}^x \leq p_{gM2|gF2}^x} f \hat{p}_{gM1|gF1}^x,$$

$$\sigma_{gM1|gF1}^x(p_{gM1|gF1}^x) f \hat{p}_{gM2|gF2}^x,$$

$$\sigma_{gM2|gF2}^x(p_{gM2|gF2}^x) dp_{gM1|gF1}^x dp_{gM2|gF2}^x$$

where (a) and (b) follow from independence and an assumption of a uniform distribution on the $p_{gM|gF}^x$ and (c) follows from the use of $f_{\mu,\sigma}$ to denote the normal PDF with mean $\mu$ and standard deviation $\sigma$ and an application of the CLT.

Finally from (1) it is possible to derive:

$$Pr\{\hat{p}_{gM1|gF1}^{x}, \hat{p}_{gM2|gF2}^{x}|p_{gM1|gF1}^{x} \le p_{gM2|gF2}^{x}\} = Pr\{W_1 \le W_2\},$$
where $W_1 \sim N(p_{gM1|gF1}^{x}, \sigma_{gM1|gF1}^{x})$ and
$W_2 \sim N(p_{gF2|gF2}^{x}, \sigma_{gM2|gF2}^{x})$ The confidences from the x-channel and y-channel are combined under the assumption of independence, i.e.

$$Pr\{data|H_{1,1}\} = Pr\{x\text{-}data|H_{1,1}\}Pr\{y\text{-}data|H_{1,1}\}.$$

In this manner it is possible to calculate the probability of the data given each hypothesis. In one embodiment, Bayes' rule may be used to find the probability of each hypothesis given the data.

Nullsomy

In one embodiment of the present disclosure, when using the permutation technique, nullsomies are handled in a special way. In addition to assigning a confidence assigned to the copy number call, it is also possible to perform an envelope test. If the envelope $e_x$ or $e_y$ is less than a threshold the probability of nullsomy is set to about 1 and the probability of the other hypotheses is set to about 0. In one embodiment of the present disclosure, this threshold may be set to about 0.05. In one embodiment of the present disclosure, this threshold may be set to about 0.1. In one embodiment of the present disclosure, this threshold may be set to about 0.2. The nullsomy permutation set for the x-channel is as follows:

| | | |
|---|---|---|
| $p_{AA|AA}^{x} \ge p_{BB|BB}^{x}$ | $p_{AB|AA}^{x} \ge p_{BB|BB}^{x}$ | $p_{AA|AB}^{x} \ge p_{BB|BB}^{x}$ |
| $p_{AA|AA}^{x} \ge p_{BB|AB}^{x}$ | $p_{AB|AA}^{x} \ge p_{BB|AB}^{x}$ | $p_{AA|AB}^{x} \ge p_{BB|AB}^{x}$ |
| $p_{AA|AA}^{x} \ge p_{AB|BB}^{x}$ | $p_{AB|AA}^{x} \ge p_{BB|AB}^{x}$ | $p_{AA|AB}^{x} \ge p_{AB|BB}^{x}$ | where the order of all contexts not listed are chosen to maximize the probability. Similarly, the nullsomy permutation set for the y-channel is as follows:

| | | |
|---|---|---|
| $p_{BB|BB}^{y} \ge p_{AA|AA}^{y}$ | $p_{AB|BB}^{y} \ge p_{AA|AA}^{y}$ | $p_{BB|AB}^{y} \ge p_{AA|AA}^{y}$ |
| $p_{BB|BB}^{y} \ge p_{AA|AB}^{y}$ | $p_{AB|BB}^{y} \ge p_{AA|AB}^{y}$ | $p_{BB|AB}^{y} \ge p_{AA|AB}^{y}$ |
| $p_{BB|BB}^{y} \ge p_{AB|AA}^{y}$ | $p_{AB|BB}^{y} \ge p_{AB|AA}^{y}$ | $p_{BB|AB}^{y} \ge p_{AB|AA}^{y}$ |

Segmentation

The standard permutation algorithm described above works well in a majority of the cases and gives theoretical confidences which correspond to empirical error rates. The one issue that has arisen is regional specific behavior in a small subset of the chromosome data. This behavior may be due to proteins blocking some sections of the chromosomes, or a translocation. To handle such regional issues, it is possible to use a segmented protocol interface to the permutation method.

If a chromosome is given a confidence below a threshold, the chromosome is broken down into a number of regions and the segmentation algorithm is run on each segment. In one embodiment of the present disclosure, about five equal segments are used. In one embodiment of the present disclosure, between about two and about five segments may be used. In one embodiment between about six and about ten segments may be used. In one embodiment of the present disclosure, more than about ten segments may be used. In one embodiment of the present disclosure, this threshold may be set to about 0.6. In one embodiment of the present disclosure, this threshold may be set to about 0.8. In one embodiment of the present disclosure, this threshold may be set to about 0.9. Then, one may focus on the segments which are assigned confidences greater than a threshold and try to find a majority vote among these high confidence segments. In one embodiment of the present disclosure, this threshold may be set to about 0.5. In one embodiment of the present disclosure, this threshold may be set to about 0.7. In one embodiment of the present disclosure, this threshold may be set to about 0.8. For example, in the case where five equal segments are used, if no majority of three or greater exists the technique may output the standard permutation algorithms confidences, while if a majority of three or more high confidence segments does exist, these segments may be pooled together and the standard permutation algorithm is run on the pooled data. The technique may then output the confidences on the pooled data as the confidence for the whole chromosome.

In one embodiment of the present disclosure, if one of the minority segments has confidence greater than a threshold, that chromosome may be flagged as being segmented. In one embodiment of the present disclosure, this threshold may be set to about 0.8. In one embodiment of the present disclosure, this threshold may be set to about 0.9. In one embodiment of the present disclosure, this threshold may be set to about 0.95

Whole Chromosome Mean

In some cases, different chromosomes may have different amplification profiles. In one embodiment of the present disclosure, it is possible to use the following technique, termed the "whole chromosome mean" technique to increase the accuracy of the data by correcting or partly correct for this amplification bias. This technique also serves to correct or partly correct for any measurement or other biases that may be present in the data. This technique does not rely on the identity of any of the alleles as measured by various genotyping techniques, rather, it relies only on the overall intensity of the genotyping measurements. Typically, the raw output data from a genotyping technique, such as a genotyping array, is a set of measured intensities of the channels that correspond to each of the four base pairs, A, C, G and T. These measured intensities, taken from the channel outputs, are designed to correlate with the amount of genetic material present, thus the base pair whose measured intensity is the greatest is often taken to be the correct allele. In some embodiments, the measured internisities for certain sets of SNPs are averaged, and the characteristic behavior of those means are used to determine the ploidy state of the chromosome.

The first step is to normalize each target for variation in amplification. This is done by using an alternate method to make an initial determination of ploidy state. Then, one selects all chromosomes with a ploidy call with a confidence greater than a certain threshold. In one embodiment of the present disclosure, this threshold is set at approximately 99%. In one embodiment of the present disclosure, this threshold is set at approximately 95%. In one embodiment of the present disclosure, this threshold is set at approximately 90%. Then, the adjusted means of the selected chromosomes are used as a measure of the overall amplification of the target. In one embodiment of the present disclosure, only the intensity of the fluorescent probe, averaged over the whole chromosome, is used. In one embodiment, the intensities of the genotyping output data, averaged over a set of alleles, is used.

Then the means are adjusted with respect to the copy number call of the chromosome, normalizing with respect to a disomy, i.e. monosomies are scaled by 2, disomies by 1 and trisomies by ⅔. The means of each chromosome of the target are then divided by the mean of these high confidence adjusted means. These normalized means may be referred to as the amplification adjusted means. In one embodiment, only the channel outputs alleles from certain contexts are used. In one embodiment, only the alleles from AA|AA or BB|BB are used.

Once the targets have been normalized for amplification variations, each chromosome may be normalized for chromosome specific amplification variance. For the $k^{th}$ chromosome find all targets which have chromosome k called disomy with confidence greater than the threshold confidence. Take the mean of their amplification adjusted means. This will serve as the average amplification of chromosome k, which may be referred to as b {k}. Without loss of generality, set b{1} to 1 by dividing out all other b{k} by b{1}.

Figure 3:
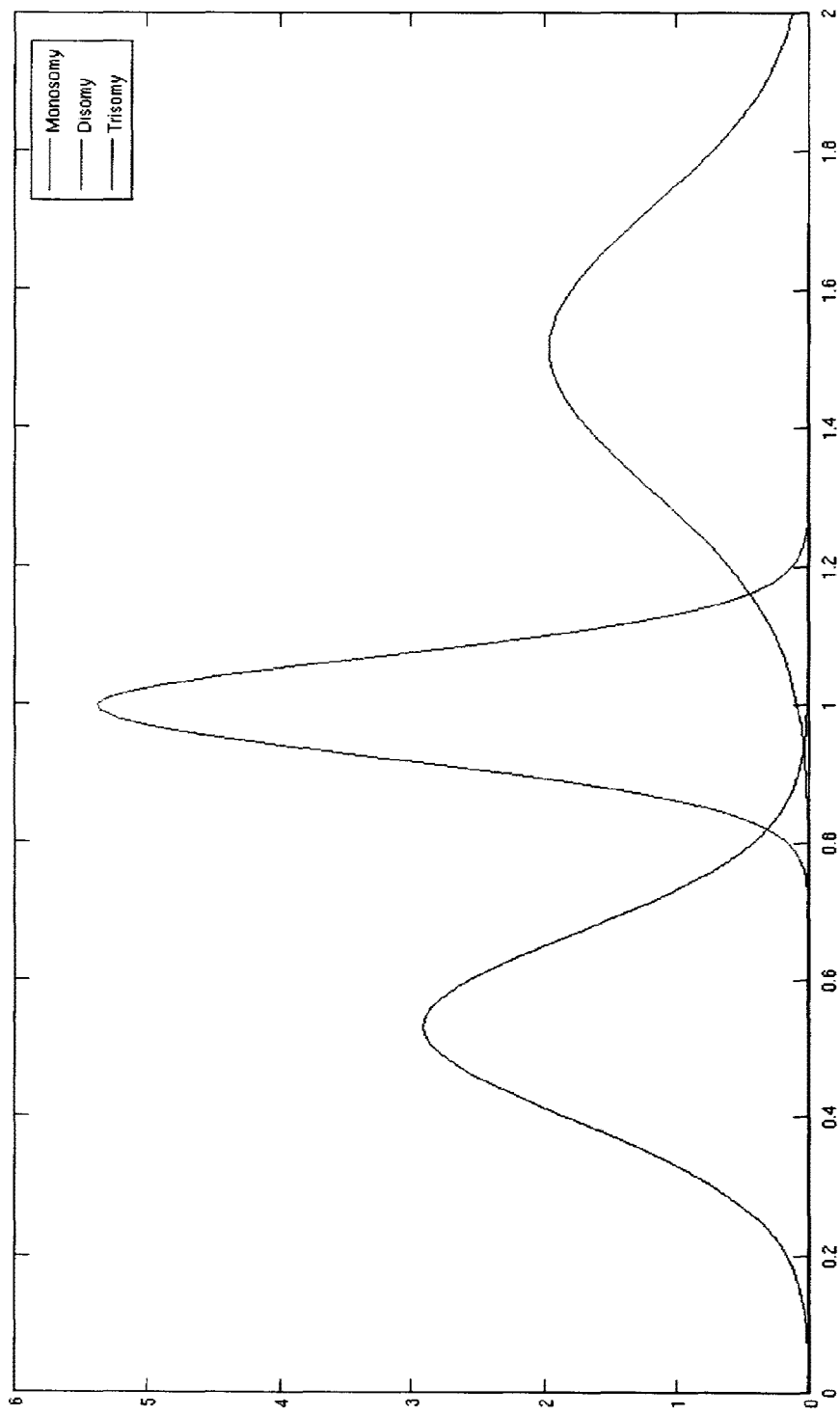
FIG. 3 shows a hypothesis distribution of various ploidy states using the Whole Chromosome Mean technique disclosed herein. Monosomic, disomic and trisomic ploidy states are shown.

The amplification normalized means may be normalized for chromosome variation by dividing out by the vector [b{1}, ..., b{24}]. These means are referred to as the standardized means. From a training set made up of historical data, it may be possible to find means and standard deviations for these standardized means under the assumptions of monosomy, disomy and trisomy. These standardized means, under the various ploidy state assumptions, may be taken to be expected intensities for comparative purposes. In one embodiment, a probability may be calculated using statistical methods known to those skilled in the art, and using the measured mean intensities of the genotyping output data, and the expected mean intensities of the genotyping output data. A probability for each of the ploidy state hypotheses may be calculated under a Gaussian hypothesis or through a non-parametric method such as a kernel method for density estimation. Then pool all data with a given ploidy call and confidence greater than a certain threshold. In one embodiment, the threshold is approximately 80%. In one embodiment, the threshold is approximately 90%. In one embodiment, the threshold is approximately 95%. Assuming Gaussian distributions, the output should be a set of hypothesis distributions. FIG. 3 shows a hypothesis distribution of monosomy (left), disomy (middle), and trisomy (right) using the Whole Chromosome Mean technique and using internal historical data as training data.

In the first step of the whole chromosome means method, each target may be normalized for amplification variation. This may be done without first normalizing for chromosome variation. In one embodiment of the present disclosure, after one calculates the [b {1}, ..., b{24}] vector from the amplification normalized means, the vector may be used to adjust the means used to determine the amplification of the target. This will result in new amplification normalized means and hence a new [b {1}, ..., b{24}] vector. One can iterate this until reaching a fixed point.

Presence of Parents Technique

In one embodiment of the present disclosure, one may use an expert statistical technique termed the "Presence of Parents" (POP) technique, described in this section, that is particularly good at differentiating any hypotheses that involve no contribution from one or more parents (i.e. nullsomy, monosomy, and uniparental disomy) from those that do. The statistical technique described in this section can detect, independently for each parent, for a given chromosome, whether or not there is a contribution from that parent's genome. The determination is made is based on distances between sets of contexts at the widest point on the CDF curves. The technique assigns probabilities to four hypotheses: {both parents present, neither parent present, only mother, only father}. The probabilities are assigned by calculating a summary statistic for each parent and comparing it to training data models for the two cases of "present" and "not present".

Calculation of Summary Statistic

The POP algorithm is based on the idea that if a certain parent has no contribution, then certain pairs of contexts should behave identically. The summary statistic $X^p$ for parent p on a single chromosome is a measure of the distance between those context pairs. In one embodiment of the present disclosure, on an arbitrary chromosome, five context distances $d_c^{p1}$ through $d_c^{p5}$ may be defined for each channel $c \in X, Y$ and each parent $p \in \{father, mother\}$. $AABB_X$ is defined as the value of the AABB context CDF curve on the X channel measured at the widest envelope width, and so on.

$$d_c^{m1} = AABB_c - BBBB_c$$

$$d_c^{m2} = AABB_c - BBBB_c$$

$$d_c^{m3} = AAAB_c - BBAB_c$$

$$d_c^{m4} = AAAA_c - BBAA_c$$

$$d_c^{m5} = AAAA_c - ABAA_c$$

When there is no contribution from the mother, all ten of $\{d_c^{mi}\}$ should be zero. When there is a contribution from the mother, the set of five $\{d_X^{mi}\}$ should be negative and the set of five $\{d_Y^{mi}\}$ should be positive. Similarly, ten distances $d_c^{f1} \ldots d_c^{f5}$ may be defined for the father, and should be zero when the father's contribution is not present.

$$d_c^{f1} = BBAB_c - BBBB_c$$

$$d_c^{f2} = BBAA_c - BBBB_c$$

$$d_c^{f3} = ABAA_c - ABBB_c$$

$$d_c^{f4} = AAAA_c - AAAB_c$$

$$d_c^{f5} = AAAA_c - AABB_c$$

Each distance may normalized by the channel envelope width to form the $i^{th}$ normalized distance $s_c^{pi}$ for parent p on channel c. The envelope width is also measured at its widest point.

$$s_c^{pi} = d_c^{pi} / abs(AAAA_c - BBBB_c)$$

A single statistic for parent p on the current chromosome is formed by summing the normalized distances over the five context pairs i and both channels.

$$X^p = \Sigma_{i=1}^{5} s_Y^{pi} - \Sigma_{i=1}^{5} s_X^{pi}$$

Training Distributions

Having calculated a statistic Xp for each parent on a given chromosome, it can be compared to distributions for the cases of "parent present" and "parent not present" to calculate the probability of each.

In one embodiment of the present disclosure, the training data distributions may be based on a set of blastomeres that have been filtered using one or a combination of other copy number calling techniques. In one embodiment of the present disclosure, hypothesis calls from both the permutation technique and the WCM are considered, with nullsomy detected using the minimum required envelope width criterion. In one embodiment, to be included in the training data, a chromosome must be called with high confidence. In one embodiment of the present disclosure, this confidence may be set at about 0.6. In one embodiment of the present disclosure, this confidence may be set at about 0.8. In one embodiment of the present disclosure, this confidence may be set at about 0.9. In one embodiment of the present disclosure, this confidence may be set at about 0.95. Chromosomes with high confidence calls of paternal monosomy or paternal uniparental disomy are included in the "mother not present" data set. Non-nullsomy chromosomes with high confidence calls on all other hypotheses are included in the "mother present" data set, and the father data sets are constructed similarly.

Figure 5:
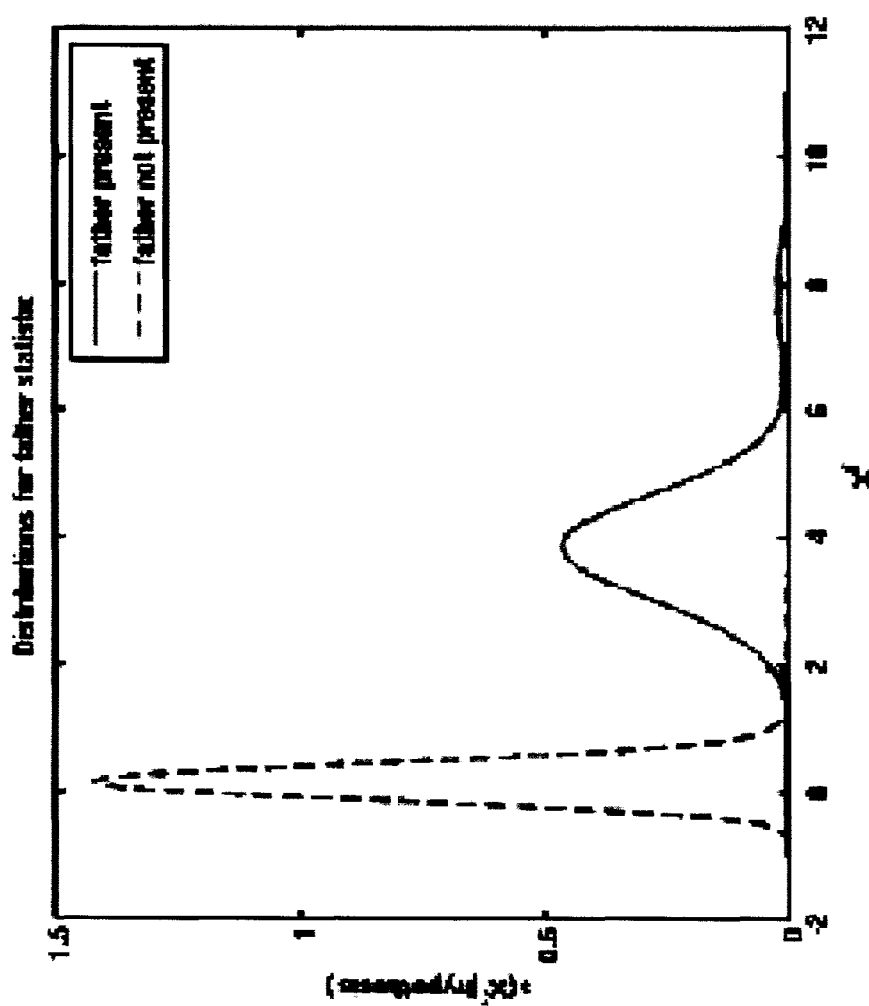
FIG. 5 shows that distributions of the genetic measurements of the father vary when genetic data is present and non-present using the Presence of Parents technique.

In one embodiment of the present disclosure, a kernel density may be formed from each data set, resulting in four distributions on X. A wide kernel width is used when the parent is present and a narrow kernel width is used when the parent is not present. In one embodiment of the present disclosure the wide kernel width may be about 0.9, 0.8 or 0.6. In one embodiment of the present disclosure, the narrow kernel width may be about 0.1, 0.2, or 0.4. Several examples of the resulting statistic distributions for the Presence of Parents techniques are shown in FIG. 4A-4B. FIG. 4A shows a distribution of genetic data of each of the parents when genetic data from the parents are present; FIG. 4B shows a distribution when genetic data from each parent is absent. Note that the "present" distributions (left) are multimodal, representing the scenarios of "one copy present" and "two copies present". The present and not-present distributions for the father statistic are shown on the same plot in FIG. 5, emphasizing that $X^f$ can be used to reliably distinguish between the two cases.

Hypothesis Probabilities

Hypothesis probabilities for a chromosome are calculated by comparing the representative statistics $X^m$ and $X^f$ to the training data distributions. The m mother-present statistic provides the likelihood functions $m=p(X^m|\text{mother present})$ and $\overline{m}=p(X^m|\text{mother not present})$ and the father-present statistic provides the likelihood functions $f=p(X^f|\text{father present})$ and $\overline{f}=p(X^f|\text{father not present})$. Considering the presence of the mother and father to be independent, the joint likelihood of a hypothesis on both parents can be calculated by multiplication of the individual parent likelihoods. Therefore, the usual hypotheses probabilities structure containing nine likelihoods p(data|hypothesis) for parent copy numbers ranging from zero to two can be constructed as shown in Table 1.

TABLE 1

Probability of data given hypothesis, combining mother and father

|  | 0 father | 1 father | 2 father |
|---|---|---|---|
| 0 mother | $\overline{mf}$ | $\overline{m}f$ | $\overline{m}f$ |
| 1 mother | $m\overline{f}$ | $mf$ | $mf$ |
| 2 mother | $m\overline{f}$ | $mf$ | $mf$ |

Presence of Homologs Technique

This algorithm, termed the "Presence of Homologs" (POH) technique, makes use of phased parent genetic information, and is able to distinguish between heterogeneous genotypes. Genotypes where there are two identical chromosomes are difficult to detect when using an expert technique that focuses on allele calls. Detection of individual homologs from the parent is only possible using phased parent information. Without phased parent information, only parent genotypes AA, BB, or AB/BA (heterozygous) can be identified. Parent phase information distinguishes between the heterozygous genotypes AB and BA. The POH algorithm is based on the examination of SNPs where the parent of interest is heterozygous and the other parent is homozygous, such as AA|AB, BB|AB, AB|AA or AB|BB. For example, the presence of a B in the blastomere on a SNP where the mother is AB and the father is AA indicates the presence of $M_2$. Because single-cell data is subject to high noise and dropout rates, the chromosome is segmented into non-overlapping regions and hypotheses are evaluated based on statistics from the SNPs in a region, rather than individually.

Mitotic trisomy is often hard to differentiate from disomy, and some types of uniparental disomy, where two identical chromosomes from one parent are present, is often difficult to differentiate from monosomy. Meiotic trisomy is distinguished by the presence of both homologs from a single parent, either over the entire chromosome in the case of meiosis-one (M1) trisomy, or over small sections of the chromosome in the case of meiosis-two (M2) trisomy. This technique is particularly useful for detecting M2 trisomy. The ability to differentiate mitotic trisomy from meiotic trisomy is useful, for example, the detection of mitotic trisomy in blastomere biopsied from an embryo indicates reasonable likelihood that the embryo is mosaic, and will develop normally, while a meiotic trisomy indicates a very low chance that the embryo is mosaic, and the likelihood that it will develop normally is lower. This technique is particularly useful in differentiating mitotic trisomy, meiotic trisomy and uniparental disomy. This technique is effective in making correct copy number calls with high accuracy.

The presence of a single parent homolog in the embryo DNA can be detected by examining that homolog's indicator contexts. A homolog's indicator contexts (one on each channel) may be defined as the contexts where a signal on that context can only come from that particular homolog. For example, the mother's homolog 1 ($M_1$) is indicated on channel X in context AB|BB and on channel Y in context BA|AA.

In one embodiment of the present disclosure, the structure of the algorithm is as follows:

(1) Phase parents and calculate noise floors per chromosome (2) Segment chromosomes (3) Calculate SNP dropout rates per segment for each context of interest (4) Calculate allele dropout rate (ADO) for each parent on each target chromosome and the hypothesis likelihoods on each segment (5) Combine across segments to produce probability of data given parent strand hypothesis for whole chromosome (6) Check for invalid calls and then calculate outputs (1) Parent Phasing and Noise Floor Calculation The phasing of the parent can be accomplished with a number of techniques. In one embodiment of the present disclosure, the parental genetic data is phased using a method disclosed in this document. In one embodiment of the present disclosure, it may require about 2, 3, 4, 5 or more embryos. In some embodiments of the present disclosure, the chromosome may be phased in segments such that phasing between one segment and another may not be consistent. The phasing method may distinguish genotypes AB and BA with a reported confidence. In one embodiment of the present disclosure, SNPs which are not phased with the required minimum confidence are not assigned to either context. In one embodiment of the present disclosure, the minimum allowed phase confidence is about 0.8. In one embodiment of the present disclosure, the minimum allowed phase confidence is about 0.9. In one embodiment of the present disclosure, the minimum allowed phase confidence is about 0.95.

The noise floor calculation may be based on a percentile specification. In one embodiment of the present disclosure, the percentile specification is about 0.90, 0.95 or 0.98. In one embodiment of the present disclosure, the noise floor on channel X is the 98th percentile value on the BBBB context, and similarly on channel Y. A SNP may be considered to have dropped out if it falls below its channel noise floor. A distinct noise floor may be calculated for each target, chromosome, and channel.

(2) Chromosome Segmentation

Segmentation of chromosomes, that is, running the algorithm on segments of a chromosome instead of a whole chromosome, is a part of this technique because the calculations are based on dropout rates, which are calculated over segments. Segments which are too small may not contain SNPs in all required contexts, especially as phasing confidence decreases. Segments which are too big are more likely to contain homolog crossovers (ie change from $M_1$ to $M_2$) which may be mistaken for trisomy. Because allele dropout rates may be as high as about 80 percent, many SNPs may be required in a segment in order to confidently distinguish allele dropout from the lack of a signal, that is, where the expected dropout rate is about or above 95 percent).

Another reason the segmentation of chromosomes may be beneficial to the technique is that it allows the technique to be executed more quickly with a given level of computational speed and power. Since the number of hypotheses, and thus the calculational needs of the technique, scale roughly as the number of alleles under consideration raised to the nth power, where n is the number of related individuals, reducing the number of alleles under consideration can significantly improve the speed of the algorithm. Relevant segments can be spliced back together after they have been phased.

In one embodiment of the present disclosure, the phasing method segments each chromosome into regions of 1000 SNPs before phasing. The resulting segments may have varying numbers of SNPs phased above a given level of confidence. In one embodiment of the present disclosure, the algorithm's segments used for calculating dropout rates may not cross boundaries of phasing segments because the strand definitions may not be consistent. Therefore, segmentation is accomplished by subdivision of the phasing segments. In one embodiment between about 2 and about 4 segments are used for a chromosome. In one embodiment between about 5 and about 10 segments are used for a chromosome. In one embodiment between about 10 and about 20 segments are used for a chromosome. In one embodiment between about 20 and about 30 segments are used for a chromosome. In one embodiment between about 30 and about 50 segments are used for a chromosome. In one embodiment more than about 50 segments are used for a chromosome.

In one embodiment of the present disclosure, approximately 20 segments are used on large chromosomes and approximately 6 segments are used on very small chromosomes. In one embodiment of the present disclosure the number of segments used is calculated for each chromosome, ranging from about 6 to 20, and varies linearly with the total number of SNPs on the chromosome. In one embodiment of the present disclosure, if the number of phasing segments is greater or equal to the desired number of segments, the phasing segments are used as is, and if not, the phasing segments are uniformly subdivided into n segments each, where n is the minimum required to reach the desired number of segments.

(3) Calculation of Dropout Rates

The data on a particular chromosome segment is summarized by the dropout rates on a set of contexts. Dropout rate may be defined, for this section, as the fraction of SNPs on the given context (with its specified channel) which measure below the noise floor. Six contexts may be measured for each parent. The dropout rates $â_x$ and $â_y$ reflect the allele dropout rate, and the dropout rates $ŝ_x^i$ and $ŝ_y^i$ may indicate the presence of homolog i. The following table shows an example of the contexts associated with each dropout rate for each parent. The measured dropout rate and the number of SNPs for each context must be stored. Note that each of the three dropout rates in the Table 2 are measured on two different contexts for each parent.

TABLE 2

Contexts for required dropout rates

|  | mom, X | mom, Y | dad, X | dad, Y |
|---|---|---|---|---|
| $â$ | AABB | BBAA | BBAA | AABB |
| $ŝ^1$ | ABBB | BAAA | BBAB | AABA |
| $ŝ^2$ | BABB | ABAA | BBBA | AAAB |

(4) Maximum Likelihood Estimation of ADO

This section contains a discussion of a method to estimate the allele dropout rate a* for each parent on each target, based on likelihoods of the form $p(D_s|M_i, a)$ and $p(D_s|F_i, a)$. The ADO may be defined as the probability of signal dropout on an AB SNP. $D_s$ may be defined as the set of context dropout rates measured on a segment of a chromosome and $M_i$, $F_i$ are the parent strand hypotheses. In one embodiment of the present disclosure, calculations are performed using log likelihoods due to the relatively small probabilities generated by multiplication across contexts and segments.

The allele dropout rate may be estimated using a maximum likelihood estimate calculated by brute force grid search over the allowable range. In one embodiment of the present disclosure, the search range $[a_{min}, a_{max}]$ may be set to about [0.4; 0.7]. At high levels of ADO, it becomes difficult to distinguish between presence and absence of a signal because the ADO approaches the noise threshold dropout rate of about 0.95.

In one embodiment of the present disclosure, the allele dropout rate is calculated for a particular target, for each parent, using the following algorithm. In one embodiment of the present disclosure, the calculation may be performed using matrix operations rather than for each target and chromosome individually.

for a ∈ $[a_{min}, a_{max}]$
   for ch ∈ [1, 22]    (22 chromosomes)
      Calculate $P(D_s|M_i, a)$ ∀I, ∀s on chromosome
      $M_s^*$ = arg max $P(D_s|M_i, a)$    (maximize over hypotheses on each segment)
      $P(D_{ch}|M_s^*, a) = \Pi_s P(D_s|M_s^*, a)$    (combine across segments on chromosome)
   $\Lambda(a) = \Pi_{ch} P(D_{ch}|M_s^*, a)$    (combine across chromosomes)
$a^*$ = arg max $\Lambda(a)$    (optimize over a)

Modeling Data Likelihoods

In one embodiment of the present disclosure, the ADO optimization may utilize a model for dropout rate on various contexts as a function of parent strand hypothesis and ADO. SNP dropouts on a single chromosome segment may be considered I.I.D. Bernoulli variables, and the dropout rate would be expected to be normally distributed with mean $\mu$ and standard deviation $\sigma=\sqrt{\mu(1-\mu)/N}$ where N is the number of SNPs measured. The dropout rate model may calculate $\mu$ as a function of the hypothesis, ADO, and context. The hypothesis and context together determine a genotype for a SNP, such as AB. The genotype and the ADO rate then determine $\mu$. In one embodiment of the present disclosure, the hypotheses for the mother are $\{M_0, M_1, M_2, M_{12}, M_{11}, M_{22}\}$. Other sets of hypotheses may be equally well used. $M_0$ means that no homolog from the mother is present. $M_{11}$ and $M_{22}$ are cases where two identical copies from the mother are present. These do not indicate meiotic trisomy. The hypotheses consistent with disomy are $M_1$ and $M_2$.

Table 3 lists $\mu$ by mother hypothesis and the various dropout rate measurements in this embodiment of the present disclosure. The identical table may be used for corresponding father strand hypotheses. Recall that p is the dropout rate which defines the noise floor, and is therefore the expected dropout rate for a channel with no allele present.

TABLE 3

Expected segment dropout rate model by strand hypothesis

|  | $M_0$ | $M_1$ | $M_2$ | $M_{12}$ | $M_{11}$ | $M_{22}$ |
|---|---|---|---|---|---|---|
| $\hat{a}$ | p | a | a | $a^2$ | $a^2$ | $a^2$ |
| $\hat{s}^1$ | p | a | p | a | $a^2$ | p |
| $\hat{s}^2$ | p | p | a | a | p | $a^2$ |

On each segment, the three dropout rates $\hat{a}$, $\hat{s}^1$ and $\hat{s}^2$ are measured on both channels. Thus, the total data $D_s$ from a segment consists of 6 dropout rate measurements, and the likelihood $P(D_s|M_i, a)$ is the product of the 6 corresponding probabilities under the normal distributions determined by $\mu$ from Table 3.

Because identification of SNPs for the $\hat{s}^1$ and $\hat{s}^2$ dropout rates depends on parent phasing, there may not be any identified SNPs in some contexts. Each of the three measured dropout rates $\hat{a}$, $\hat{s}^1$ and $\hat{s}^2$ may be measured on two different contexts corresponding to the two channels. If any of the three has no data in either of its contexts, then likelihoods for that segment may be not calculated. Chromosomes which have been called nullsomy by the standard envelope width test may be not included.

(5) Calculate Chromosome Likelihoods by Combining Segments

The likelihood calculations described above provide a data likelihood $P(D_s|M_i)$ on each segment s for each parent strand hypothesis $M_i$. The two parents may still considered independently. The strand likelihoods may then be normalized so that the sum of all likelihoods on a single segment is one. The normalized likelihoods from segment s will be referred to as $\{\Lambda_s(M_i)\}$. This process will also depend on the normalized segments lengths $\{x_s\}$, defined as the fraction of a chromosome's SNPs contained on segment s.

In one embodiment of the present disclosure, the likelihoods from all segments may now be combined to form a set of chromosome likelihoods for the number of distinct strands present. All of the data for a chromosome is combined into $D_{ch}$. The chromosome hypotheses are $S_0^m$, $S_1^m$, $S_2^m$ for the mother. $S_1^m$ is the hypotheses that only one distinct homolog is present at a time, which allows the strand hypotheses $M_1$; $M_{11}$; $M_2$; $M_{22}$. $S_2^m$ is the meiotic trisomy hypotheses, where two distinct strands have been contributed from the mother. Hypotheses on the mother's strand number will be discussed; hypotheses on the father's strand may be calculated in an analogous fashion.

$S_0^m$ corresponds one-to-one with the no-strand hypothesis $M_0$. Therefore, the likelihood of no-copies is simply the sum (weighted by segment length) of the no-strand likelihoods on each segment.

$P(D_{ch}|S_0^m)=\Sigma_s\Lambda_s(M_0)x_s$ $S_1^m$ (one copy at a time) corresponds to the strand hypotheses $M_1$; $M_{11}$; $M_2$, $M_{22}$. Without making any assumptions about recombination, one may expect that a single parent copy will be either M1 or M2 strand at all segments. In this embodiment of the present disclosure, rather than trying to detect how many copies of a single strand are present, the double-strand hypotheses $M_{11}$ and $M_{22}$ are included as well. In another embodiment of the present disclosure, $M_1$ and $M_2$ may be grouped into one hypothesis, and $M_{11}$ and $M_{22}$ may be grouped in another hypothesis. In other embodiments, other hypotheses may refer to other groupings of the actual state of the genetic material. Again, the chromosome likelihood is simply a weighted sum.

$P(D_{ch}|S_1^m)=\Sigma_s(\Lambda_s(M_1)+\Lambda_s(M_{11})+\Lambda_s(M_2)+\Lambda_s(M_{22}))x_s$ Meiotic trisomy is characterized by the presence of two non-identical chromosomes from a single parent. Depending on the type of meiotic error, these may be a complete copy of each of the parent's homologs (meiosis-1), or they may be two different recombinations of the parent's homologs (meiosis-2). The first case results in strand hypothesis $M_{12}$ on all segments, but the second case results in $M_{12}$ only where the two different combinations don't match. Therefore, the weighted sum approach used for the other hypotheses may not be appropriate.

The meiotic trisomy likelihood calculation is based on the assumption that unique recombinations will be distinct on at least one continuous region covering at least a quarter of the chromosome. In other embodiments, other sizes for the continuous region on which unique recombinations are distinct may be used. A detection threshold that is too low may result in trisomies being incorrectly called due to mid-segment recombinations and noise. Because meiosis-2 trisomy does not correspond to any whole-chromosome strand hypothesis, the likelihood may not be proportional to the sum of segment likelihoods as it is for the other two copy numbers. Instead, the confidence on the meiotic hypothesis depends on whether or not the meiotic threshold has been met, and the overall confidence of the chromosome.

In one embodiment of the present disclosure, the chromosomes may be reconstructed by recombining the segments along with their relative probabilities using the following steps:

1. Find length x of longest continuous region with $\Lambda(M_{12})>0:8$ by combining adjacent segments
2. If x>0:25 then set the meiotic flag as true. Otherwise set the flag as false.
3. Calculate general confidence on chromosome by averaging confidence on most likely hypothesis from each segment $C=\Sigma_s x_s\max\Lambda_s(M_i)4$. If the meiotic flag is true, then let the normalized $P(D_{ch}|S_2^m)=C$. Otherwise let $P(D_{ch}|S_2^m)=1-C$.

The result is that if the meiotic flag is triggered on a high confidence chromosome, the meiotic hypothesis will have correspondingly high confidence. If the meiotic flag is not triggered, the meiotic hypothesis will have low confidence.

(6) Check for Invalid Calls and Calculate CNC Outputs

The final step is to calculate likelihoods on true parent copy numbers without distinction between meiotic and mitotic error. The standard $HN_mN_f$ notation will be adapted for single parents, where $N_m$ is the number of strands from the mother present, and $N_f$ is the number of strands from the father present.

$$P(D_{ch}|H0x)=P(D_{ch}|S_0'^m)$$

$$P(D_{ch}|H1x)=P(D_{ch}|S_1'^m)$$

$$P(D_{ch}|H2x)=P(D_{ch}|S_2'^m)P(\text{meiotic})+P(D_{ch}|S_1'^m)P(\text{mitotic})$$

The final formula is explained by the fact that trisomy can arise due to two disjoint events: meiotic error and mitotic error. Meiotic error corresponds to the hypothesis $S_2'^m$ (2 different copies) and mitotic error corresponds to the hypothesis $S_1'^m$ (duplicate of the same homolog). The prior probabilities of these two events are assumed equal. As a result, a very high confidence on the $S_1'^m$ hypothesis puts approximately equal confidence on H1x and H2x, but a very high confidence on the $S_2'^m$ hypothesis favors only H2x.

This algorithm is well suited to detecting segmentation in chromosomes. A segmented disomy is characterized by the presence of a copy from each parent, where at least one parent's copy is incomplete. If one parent has greater than about 80 percent confidence on the 0 strands hypothesis ($M_0$ or $F_0$) for at least a quarter of the chromosome, this chromosome may be flagged as "segmented monosomy" even if the confidence calculations using other expert techniques result in a disomy call. This segmentation flag may be combined with the segmentation flag from the Permutation technique so that either one can independently detect an error. If the overall algorithm call is monosomy, the segmented flag may not be activated because it would be redundant.

At this point in the execution of the technique, copy hypothesis confidences have been assigned for each parent for each chromosome where dropout rates were available for at least one segment. However, some chromosomes may not have been phased with high confidence and their likelihoods may reflect dropout rates that were only available for a very small fraction of the chromosome. In one embodiment of the present disclosure, to avoid making calls based on insufficient or unclear data, checks may be performed to remove calls on chromosomes with incomplete phasing or very noisy results.

After the checks are performed, the parent copy hypotheses may be converted to the standard CNC hypotheses. For mother copies $N_m$ and father copies $N_f$, the likelihood of the CNC hypothesis $HN_mN_f$ is simply a multiplication of the independent parent copy likelihoods. If one parent was not called due to incomplete phasing or noisy data, the algorithm may output uniform likelihoods across that parent but still call the other parent.

$$P(D|HN_mN_f)=P(D|HN_mx)P(D|H\times N_f)$$

Check for Incomplete Phasing

The phasing coverage on a chromosome is the sum of segment lengths for which likelihoods were calculated. In some embodiments of the present disclosure, no likelihoods are calculated when any of the three dropout rate measurements has no data. If phasing coverage is less than half, no call is produced. In the case where meiotic trisomy is flagged by a sequence of $M_{12}$ or $F_{12}$ segments of combined length of about 0.25, any phasing coverage of less than 0.75 is not sufficient to rule out such a segment. However, if a meiotic segment of length 0.25 is detected, it may still be called. In one embodiment of the present disclosure, phasing coverage between about 0.5 and about 0.75 is dealt with as follows.

if it is flagged as trisomy, the ploidy call is as if completely phased if the call is partial or complete monosomy, the ploidy call is as if completely phased otherwise, do not call (set uniform likelihood for this parent's copies)

Check for Noisy Chromosomes

Some chromosomes may resist classification using this algorithm. In spite of high confidence phasing and segment likelihoods, whole-chromosome results are unclear. In some cases, these chromosomes are characterized by frequent switching between maximum likelihood hypothesis. Although only a few recombination events are expected per chromosome, these chromosomes may show nearly random switching between hypotheses. Because the meiotic hypothesis is triggered by a meiotic sequence of length of about 0.25, false trisomies may often be triggered on noisy chromosomes.

In some embodiments of the present disclosure, the algorithm declares a "noisy chromosome" by combining adjacent segments with the same maximum likelihood hypothesis. The average length of these new segments is compared to the average length of the set of original segments. If this ratio is less than two, then few adjacent segments may have matching hypotheses, and the chromosome may be considered noisy. This test is based on the assumption that the original segmentation is expected to be somewhat uniform and dense. A switch to an optimal segmentation algorithm would require a new criterion.

If a chromosome is declared noisy for a particular parent, then the copy hypotheses for that parent may be set as uniform and the meiotic and segmented monosomy flags are set as false.

Sex Chromosome Technique

The techniques described above are designed for autosomic chromosomes. Since the likely genetic states of the sex chromosomes (X and Y) are different, different techniques may be more appropriate. In this section several techniques are described that are designed specifically for determination of the ploidy state of the sex chromosomes.

In addition to the expected numbers of sex chromosomes being different, determination of the ploidy state of sex chromosomes is further complicated by the fact that there are regions on the X and Y chromosome that are homologous, and others that are similar but non-polymorphic. The Y chromosome may be considered to be a mosaic of different regions, and the behavior of the Y probes depends largely upon the region to which they bind on the Y chromosome. Many of the Y probes do not measure SNPs per se; instead, they bind to locations that are non-polymorphous on both the X and Y chromosomes. In some cases, a probe will bind to a location that is always AA on the X chromosome but always BB on the Y chromosome, or vice versa. These probes are termed "two-cluster" probes because when one of these probes is applied to a set of male and female samples, the resulting scatter plot always clusters into two clusters, segregated by sex. The males are always heterozygous, and the females are always homozygous.

XYZ Chromosome Technique

In one embodiment of the present disclosure the ploidy determination of sex chromosomes is handled by considering an abstract chromosome termed "chromosome 23", composed of four distinct sub-chromosomes, termed X, Y, XY, and Z. Chromosome XY corresponds to those probes that hybridize to both the X and Y chromosomes in what are known as the pseudoautosomal regions. In contrast, the probes associated with chromosome X are only expected to hybridize to chromosome X, and those probes associated with chromosome Y are only expected to hybridize to chromosome Y. Chromosome Z corresponds to those "two cluster" probes that hybridize to the Y chromosome in what is known as the X-transpose region the region that is about 99.9% concordant with a similar region on the X chromosome, and whose allele values are polar to their cognates in X. Thus, a Z probe will measure AB (disregarding noise) on a male sample, and either AA or BB on a female sample, depending on the locus.

The discussion below describes the math behind this technique. In terms of the component sex chromosomes, the goal of this technique is to distinguish the following cases: {∅, X, Y, XX, XY, YY, XXX, XXY, XYY, XXYY}. Note that, if chromosome 23 is euploid, then it must be one of {XX,XY} and hence must have a copy number of 2. In the cases of uniparental disomy: XX from mother and nothing from father, or YY from father, one may arbitrarily assign the copy number of 5, or merge them in with the monosomy hypotheses.

The linkage between the X and Y sub-chromosomes expresses itself only in the joint prior distribution $P(n_X^F, n_Y^F)$ on the number of sub-chromosomes from X and Y contributed by the father.

A Notation
1. n is the chromosome copy number for chromosome 23.
2. $n_X^M$ is the number of copies of sub-chromosome X supplied to the embryo by the mother: 0, 1, or 2. For notational purposes, it is convenient also to define $n_Y^M=0$ as the number of copies of sub-chromosome Y supplied to the embryo by the mother.
3. $(n_X^F, n_Y^F)$ are the number of copies of sub-chromosomes X and Y jointly supplied to the embryo by the father. These copy number pairs must belong to the set {(0,0), (0,1),(1,0),(2,0),(1,1),(0,2)}.

Note that the preceding three defined variables satisfy the constraint $n_X^M + n_X^F + n_Y^F = n$.

4. Define $n_{XY}^M = n_X^M$, $n_{XY}^F = n_X^F + n_Y^F$
5. Define $n_Z^M = n_X^M$, $n_Z^F = n_X^F + n_Y^F$
6. $p_d$ is the dropout rate, and $f(p_d)$ is a prior on this rate.
7. $p_a$ is dropin rate, and $f(p_a)$ is a prior on this rate.
8. c is the cutoff threshold for no-calls.
9. $D_X = \{(x_{Xk}, y_{Xk})\}$ is the set of raw platform responses on channels x and y over all SNPs k on sub-chromosome X. Similarly $D_Y = \{(x_{Yk}, y_{Yk})\}$ is the set of raw platform responses on channels x and y over all SNPs k on sub-chromosome Y, $D_{XY} = \{(x_{XYk}, y_{XYk})\}$ is the set of raw platform responses on channels x and y over all SNPs k on sub-chromosome XY, and $D_Z = \{(x_{Zk}, y_{Zk})\}$ is the set of raw platform responses on channels x and y over all SNPs k on sub-chromosome Z.
10. $D_X(c) = \{G(x_{Xk}, y_{Xk}); c\} = [\hat{g}_{Xk}^{(c)}]$ is the set of genotype calls over all SNPs k on sub-chromosome X, and similarly for sub-chromosomes Y, XY, and Z. Note that the genotype calls depend on the no-call cutoff threshold c.
11. Define a sub-chromosome index j, where j∈{X, Y, XY, Z}. In this case, we can reference $D_j(c)$ to refer to the data associated with sub-chromosome j.
12. $\hat{g}_{jk}^{(c)}$ is the genotype call on the $k^{th}$ snp (as opposed to the true value) on sub-chromosome j: one of AA, AB, BB, or NC (no-call).
13. Given a genotype call $\hat{g}$ at snp k, the variables $(\hat{g}^A, \hat{g}^B)$ are indicator variables (1 or 0). Formally, $\hat{g}^A = (A\epsilon\hat{g})$, and $\hat{g}^B = (B\epsilon\hat{g})$.
14. $M = \{g_{jk}^M\}$ is the known true sequence of genotype calls on the mother on sub-chromosome j. $g^M$ refers to the genotype value at some particular locus. Note that, for j=Y, $\{g_{Yk}^M\}$ is taken to be a sequence of no-calls: NC.
15. $F = \{g_{jk}^F\}$ is the known true sequence of genotype calls on the father on sub-chromosome j. $g^F$ refers to the genotype value at some particular locus.
16. $C_{MF}(j)$ is the class of conceivable joint parental genotypes that can occur on sub-chromosome j. Each element of $C_{MF}(j)$ is a tuple of the form $(g^M, g^F)$, e.g., (AA, AB), and describes one of the possible joint genotypes for mother and father. The sets $C_{MF}(f)$ are listed in full here:
 a. $C_{MF}(X) = \{AA, AB, BB\} \times \{AA, BB\}$
 b. $C_{MF}(Y) = \{NC\} \times \{AA, BB\}$
 c. $C_{MF}(XY) = \{AA, AB, BB\} \times \{AA, AB, BB\}$
 d. $C_{MF}(Z) = \{AA, BB\} \times \{AB\}$
17. $n_j^A, n_j^B$ are the true number of copies of A and B on the embryo (implicitly at locus k), respectively on sub-chromosome j. Values must be in 0, 1, 2, 3, 4 for j∈{X,XY,Z} and in 0, 1, 2 for j∈{Y}.
18. $c_j^{AM}, c_j^{BM}$ are the number of A alleles and B alleles respectively supplied by the mother to the embryo (implicitly at locus k) on sub-chromosome j. For j=X or XY or Z, the values must be in 0, 1, 2, and must not sum to more than 2. For j=Y, the values must be (0,0). Similarly, $c_j^{AF}, c_j^{BF}$ are the number of A alleles and B alleles respectively supplied by the father to the embryo (implicitly at locus k) on sub-chromosome j. The father has the additional constraint for j=X or j=Y that one of $c_j^{AF}, c_j^{BF}$ must be zero, reflecting the fact that the father cannot contribute heterozygous material from either individual sex chromosome. For j=XY, there is no such constraint.

For j=Z, the constraints are as follows:
1. When the locus is homo AA on the mother, then we have $c_Z^{AF} = n_X^F$ and $c_Z^{BF} = n_Y^F$.
2. When the locus is homo BB on the mother, then we have $c_Z^{BF} = n_X^F$ and $c_Z^{AF} = n_Y^F$.

Altogether, the four values $\{c_j^{AM}, c_j^{BM}, c_j^{AF}, c_j^{BM}\}$ exactly determine the true genotype of the embryo on sub-chromosome j. For example, if the values were (1,1) and (1,0), then the embryo would have type AAB.

Note also that the following constraints hold for all j:
1. $c_j^{AM} + c_j^{BM} = n_j^M$
2. $c_j^{AF} + c_j^{BF} = n_j^F$ The following solution applies just to chromosome 23 and takes into account the interrelation between sub-chromosomes X, Y, and XY.

$$P(n \mid D_x(c), D_y(c), D_{XY}(c), M, F) = \sum_{(n_X^M, n_X^F, n_Y^F) \in n} P(n_X^M, n_X^F, n_Y^F \mid D_X(c), D_y(c), D_{XY}(c), M, F)$$

$$P(n_X^M, n_X^F, n_Y^F \mid D_X(c), D_y(c), D_{XY}(c), M, F) = \frac{P(n_x^M) P(n_X^F, n_Y^F) P(D_X(c), D_Y(c), D_{XY}(c) \mid n_X^M, n_X^F, n_Y^F, M, F)}{\sum_{(n_X^M, n_X^F, n_Y^F)} P(n_x^M) P(n_X^F, n_Y^F) P(D_X(c), D_Y(c), D_{XY}(c) \mid n_X^M, n_X^F, n_Y^F, M, F)}$$

$P(n_X^F, n_Y^F)$ is a prior distribution that may be set reasonably. The probabilities of (1,0) and (0,1) may be set reasonably high, as these are the euploidy states.

$$P(D_X(c), D_Y(c), D_{XY}(c) | n_X^M, n_X^F, n_Y^F, M, F) = P(D_X(c) | n_X^M, n_X^F, M, F) \times P(D_Y(c) | n_Y^F, M, F) \times P(D_{XY}(c) | n_{XY}^M, n_{YX}^F, M, F)$$

Keep in mind in the above that $n_{XY}^M = n_X^M$ and $n_{XY}^F = n_X^F + n_Y^F$.

$$P(D_j(c) | n_j^M, n_j^F, M, F) = \iint f(p_d) f(p_a) P(D_j(c) | n_j^M, n_j^F, M, F, p_d, p_a) dp_d dp_a$$

$$(*) P(D_j(c) | n_j^M, n_j^F, M, F, p_d, p_a) = \Pi_k P(G(x_{jk}, y_{jk}; c) | n_m^M, n_j^F, g_{jk}^M, g_{jk}^F, p_d, p_a)$$ Handling (*) On XY Chromosome The case of the XY chromosome behaves similarly to any autosome. The math is discussed here.

$$P(D_x(c) | n_X^M, n_X^F, M, F, p_d, p_a) = \prod_k P(G(x_{Xk}, y_{Xk}; c) | n_X^M, n_X^F, g_{Xk}^M, g_{Xk}^F, p_d, p_a)$$

$$= \prod_{\substack{g^M \in \{AA, AB, BB\} \\ g^F \in \{AA, AB, BB\} \\ \hat{g} \in \{AA, AB, BB, NC\}}} \prod_{\{k: g_{Xk}^M = g^M, g_{Xk}^F = g^F, \hat{g}_{Xk}^{(c)} = \hat{g}\}} P(\hat{g} | n_X^M, n_X^F, g^M, g^F, p_d, p_a)$$

$$= \prod_{\substack{g^M \in \{AA, AB, BB\} \\ g^F \in \{AA, AB, BB\} \\ \hat{g} \in \{AA, AB, BB, NC\}}} P(\hat{g} | n_X^M, n_X^F, g^M, g^F, p_d, p_a)^{|\{k: g_{Xk}^M = g^M, g_{Xk}^F = g^F, \hat{g}_{Xk}^{(c)} = \hat{g}\}|}$$

$$= \exp\left( \prod_{\substack{g^M \in \{AA, AB, BB\} \\ g^F \in \{AA, AB, BB\} \\ \hat{g} \in \{AA, AB, BB, NC\}}} |\{k: g_{Xk}^M = g^M, g_{Xk}^F = g^F, \hat{g}_{Xk}^{(c)} = \hat{g}\}| \times \log P(\hat{g} | n_X^M, n_X^F, g^M, g^F, p_d, p_a) \right)$$

$$P(\hat{g} | n_X^M, n_X^F, g^M, g^F, p_d, p_a)$$

$$= \sum_{n^A, n^B} \underbrace{P(n^A, n^B | n_X^M, n_X^F, g^M, g^F,)}_{\text{genetic modeling}} \overbrace{P(\hat{g}^A | n^A, p_d, p_a) P(\hat{g}^B | n^B, p_d, p_a)}^{\text{platform modeling}}$$

Handling (*) on X Chromosome

The additional constraints here are that the father is never heterozygous on X.

$$P(D_x(c) | n_X^M, n_X^F, M, F, p_d, p_a) = \prod_k P(G(x_{Xk}, y_{Xk}; c) | n_X^M, n_X^F, g_{Xk}^M, g_{Xk}^F, p_d, p_a)$$

$$= \prod_{\substack{g^M \in \{AA, AB, BB\} \\ g^F \in \{AA, BB\} \\ \hat{g} \in \{AA, AB, BB, NC\}}} \prod_{\{k: g_{Xk}^M = g^M, g_{Xk}^F = g^F, \hat{g}_{Xk}^{(c)} = \hat{g}\}} P(\hat{g} | n_X^M, n_X^F, g^M, g^F, p_d, p_a)$$

$$= \prod_{\substack{g^M \in \{AA, AB, BB\} \\ g^F \in \{AA, BB\} \\ \hat{g} \in \{AA, AB, BB, NC\}}} P(\hat{g} | n_X^M, n_X^F, g^M, g^F, p_d, p_a)^{|\{k: g_{Xk}^M = g^M, g_{Xk}^F = g^F, \hat{g}_{Xk}^{(c)} = \hat{g}\}|}$$

$$= \exp\left( \prod_{\substack{g^M \in \{AA, AB, BB\} \\ g^F \in \{AA, BB\} \\ \hat{g} \in \{AA, AB, BB, NC\}}} |\{k: g_{Xk}^M = g^M, g_{Xk}^F = g^F, \hat{g}_{Xk}^{(c)} = \hat{g}\}| \times \log P(\hat{g} | n_X^M, n_X^F, g^M, g^F, p_d, p_a) \right)$$

$$P(\hat{g} | n_X^M, n_X^F, g^M, g^F, p_d, p_a)$$

$$= \sum_{n^A, n^B} \underbrace{P(n^A, n^B | n_X^M, n_X^F, g^M, g^F,)}_{\text{genetic modeling}} \overbrace{P(\hat{g}^A | n^A, p_d, p_a) P(\hat{g}^B | n^B, p_d, p_a)}^{\text{platform modeling}}$$

Handling (*) on Y Chromosome

The constraints here are that the mother's copy number is 0 and the father is never heterozygous on Y.

$$P(D_Y(c) \mid n_Y^F, M, F, p_d, p_a) = \prod_k P(G(x_{Yk}, y_{Yk}; c) \mid n_Y^F, g_{Yk}^F, p_d, p_a)$$

$$= \prod_{\substack{g^F \in \{AA,BB\} \\ \hat{g} \in \{AA,AB,BB,NC\}}} \prod_{\{k: g_{Yk}^F = g^F, \hat{g}_{Yk}^{(c)} = \hat{g}\}} P(\hat{g} \mid n_Y^F, g^F, p_d, p_a)$$

$$= \prod_{\substack{g^F \in \{AA,BB\} \\ \hat{g} \in \{AA,AB,BB,NC\}}} p(\hat{g} \mid n_Y^F, g^F, p_d, p_a)^{|\{k, g_{Yk}^F = g^F, \hat{g}_{Yk}^{(c)} = \hat{g}\}|}$$

$$= \exp\left( \sum_{\substack{g^F \in \{AA,BB\} \\ \hat{g} \in \{AA,AB,BB,NC\}}} |\{k : g_{Yk}^F = g^F, \hat{g}_{Yk}^{(c)} = \hat{g}\}| \times \log P(\hat{g} \mid n_Y^F, g^F, p_d, p_a) \right)$$

$$P(\hat{g} \mid n_Y^F, g^F, p_d, p_a) = \sum_{n^A, n^B} \underbrace{P(n^A, n^B \mid n_Y^F, g^F)}_{\text{genetic modeling}} \overbrace{P(\hat{g}^A \mid n^A, p_d, p_a) P(\hat{g}^B \mid n^B, p_d, p_a)}^{\text{platform modeling}}$$

$$P(n^A, n^B \mid n_Y^F, g^F,) = P(n^A, n^B \mid n_Y^F, g^F, n_Y^M = 0, g^M = NC)$$

Here the solution is continued for all sub-chromosomes. Keep in mind that when j=Y, then $n_j^M=0$ and $g_{jk}^M=NC$ for all k.

$$P(\hat{g} \mid n_j^M, n_j^F, g^M, g^F, p_a, p_a) =$$

$$\sum_{n^A, n^B} \underbrace{P(n^A, n^B \mid n_j^M, n_j^F, g^M, g^F,)}_{\text{genetic modeling}} \overbrace{P(\hat{g}^A \mid n^A, p_d, p_a) P(\hat{g}^B \mid n^B, p_d, p_a)}^{\text{platform modeling}}$$

$$P(\hat{g}^A \mid n^A, p_d, p_a) = \hat{g}^A\left((1-p_d^{n^A}) + (n^A=0)p_a\right) +$$
$$(1 - \hat{g}^A)\left((n^A > 0)p_d^{n^A} + (n^A=0)(1-p_a)\right)$$

$$P(\hat{g}^B \mid n^E, p_d, p_a) = \hat{g}^B\left((1-p_d^{n^B}) + (n^B=0)p_a\right) +$$
$$(1 - \hat{g}^B)\left((n^B > 0)p_d^{n^B} + (n^B=0)(1-p_a)\right)$$

$$P(n^A, n^B \mid n_j^M, n_j^F, g^M, g^F,) =$$

$$\sum_{\substack{c_j^{AM}+c_j^{AF}=n^A \\ c_j^{BM}+c_j^{BF}=n^B}} P(c_j^{AM}, c_j^{BM} \mid n_j^M, g^M) P(c_j^{AF} \mid n_j^F, g^F)$$

Mother Sub-Cases: for j in {X, XY}, we have $$P(c_j^{AM}, c_j^{BM} \mid n_j^M, g^M) = (c_j^{AM} + c_j^{BM} = n_j^M) \begin{cases} (c_j^{BM} = 0), & g^M = AA \\ (c_j^{AM} = 0), & g^M = BB \\ \frac{1}{n_j^M + 1}, & g^M = AB \end{cases}$$

For j=Y we have, which is degenerate for the mother, we have:

$$P(c_Y^{AM}, c_Y^{BM} \mid n_Y^M, g^M) = (c_Y^{AM} + c_{y'}^B = 0)(n_Y^M = 0)$$
$$(g^M = NC)$$

Father Sub-Cases: for j in {X,Y}, we have:

$$P(c_j^{AF}, c_j^{BF} \mid n_j^F, g^M) =$$
$$(c_j^{AF} + c_j^{BF} = n_i^F)((c_j^{AF} = 0) \cup (c_j^{BF} = 0)) \begin{cases} (c_j^{BF} = 0), & g^F = AA \\ (c_j^{AF} = 0), & g^F = BB \end{cases}$$

For j=XY, the mathematics are the same as for the mother, viz:

$$P(c_{XY}^{AF}, c_{XY}^{BF} \mid n_{XY}^F, g^F) = (c_{XY}^{AF} + c_{XY}^{BF} = n_{XY}^F) \begin{cases} (c_{XY}^{BF} = 0), & g^F = AA \\ (c_{XY}^{AF} = 0), & g^F = BB \\ \frac{1}{n_{XY}^F + 1}, & g^F = AB \end{cases}$$

X Chromosome Technique

In one embodiment of the present disclosure, the X-chromosome technique, described here, is able to determine the ploidy state of the X-chromosome with high confidence. In practice, this technique has similarities with the permutation technique, in that the determination is made by examining the characteristic CDF curves of the different contexts. This technique specifically uses the distance between certain context CDF curves to determine the copy number of the sex chromosome.

In one embodiment of the present disclosure, the algorithm may be modified in the following way to optimize for the X-chromosome. In this embodiment, slight modifications may be made in the allele distribution, the response model, and possible hypothesis. The formula is:

$$P(g_{ij} \mid D, F) = \frac{P(D_{ij}^e \mid g_{ij}, F_j^e)}{P(D \mid F)} \Sigma_{g^M, g^F} P(g^M) P(g^F) P(D_i^M \mid g^M)$$

$$P(D_i^f \mid g^F) \Sigma_h P(g_{ij} \mid g^M, g^F, h, F_j^e) * Q(h, g^M, g^F, F, D, i, j)$$

-continued where $$Q(h, g^M, g^F, F, D, i, j) = \sum_{\substack{H_i \\ H_{ij}^e = h}} \prod_{\substack{a=1, \ldots, k, \\ a \neq j}} P(D_{ia}^e \mid g^M, g^F, H_{ia}^e, F_a^e)$$

$$\prod_{a=1, \ldots, l} P(D_{ia}^e \mid g^F, H_{ia}^s, F_a^s) * W_1(H_i, D, i, F) * W_2(H_i, D, i, F)$$

In addition, some or all of the following changes may be made:

The response model $P(D_{ij}^e \mid g_{ij}, F_j^e)$ depends on $F_j^e$. If $F_j^e = 0$, 2 copies, then it may be modeled as before, if $F_j^e = 1$, use one copy and it may be modeled the same as for sperm.

$P(g^F)$ is p, (1–p), for AA, BB respectively, omitting AB.

$P(D_i^f \mid g^F)$ is same as before, since we assume 100% correct parents, just make sure to omit any snips with $D_i^f = AB$ h, the embryo hypothesis on (mother, father), previously had 4 possibilities, now only consider 2 possibilities for M1, M2, since contribution from the father either does not exist (for $F_j^e = 0$), or only has one hypothesis (for $F_j^e = 1$). This is valid for each embryo. Similarly on sperm there is only one hypothesis.

$P(g_{ij} \mid g^M, g^F, h, F_j^e)$ may be calculated slightly differently depending on $F_j^e$, i.e depending on whether we consider the father's contribution.

$Q(h, g^M, g^F, F, D, i, j)$ may be calculated the same way as before, taking into account the reduction in the hypothesis space, and above mentioned changes depending on $F_j^e$.

Context Distance: X Chromosome

In another embodiment of the present disclosure, the ploidy state of the X-chromosome may be determined as follows. The first step is to determine the distance between the following four contexts: AA|BB and BB|AA on channel X, AA|BB and BB|AA on channel Y, AB|BB and BB|AA on channel X, and AB|AA and AA|BB on channel Y. These distances may be taken at the point where AA|AA and BB|BB are furthest apart, and then normalized by the distance between AA|AA and BB|BB. This normalization serves as a way to remove any variation in the amplification process. Then distributions may be built for each of the normalized distances under the hypotheses $H_{10}$, $H_{01}$, $H_{11}$, $H_{21}$ and $H_{12}$ using high confidence ploidy calls on the autosomal chromosomes. In one embodiment of the present disclosure, the training set is restricted to chromosomes 1-15.

Figure 6:
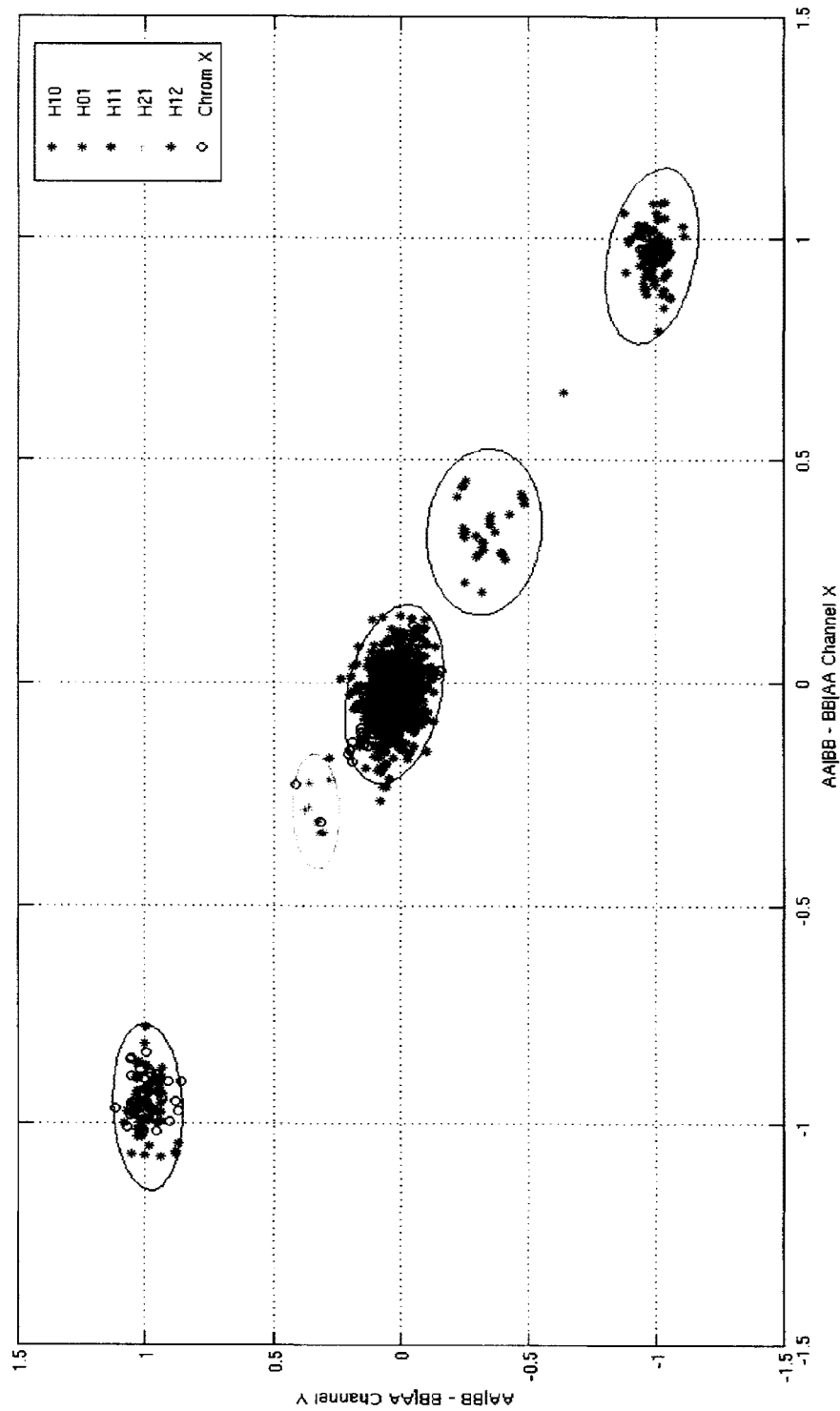
FIG. 6 shows a plot of a set of Single Nucleotide Polymorphisms. A normalized intensity of one channel output is plotted against the other.
Figure 7:
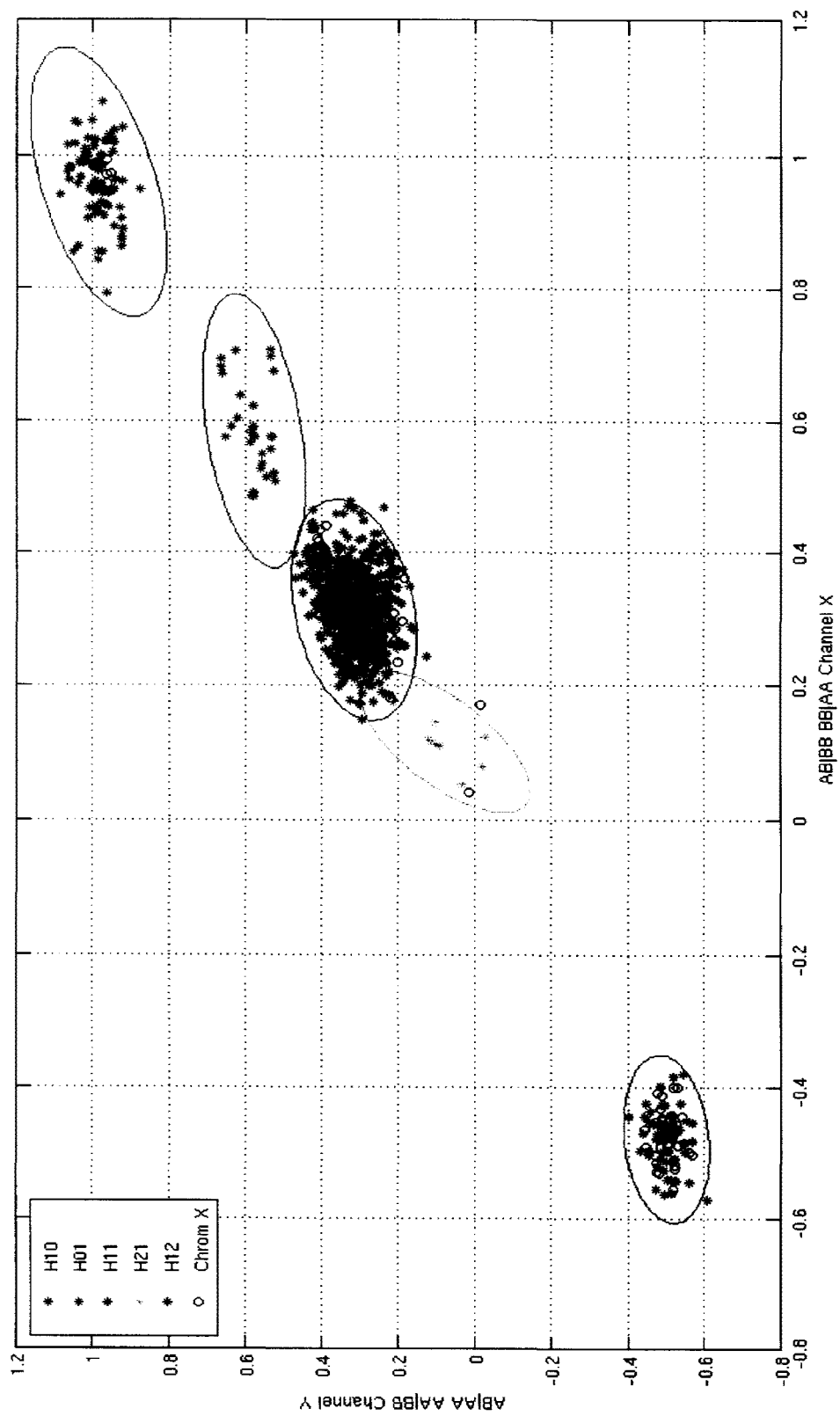
FIG. 7 shows a plot of a set of Single Nucleotide Polymorphisms. A normalized intensity of one channel output is plotted against the other.
Figure 8A:
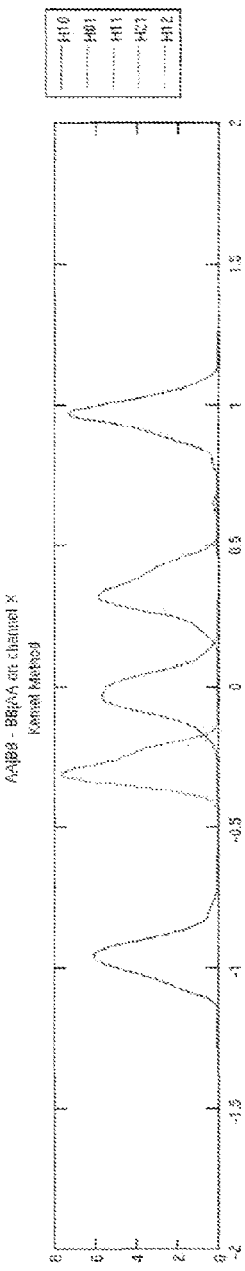
FIGS. 8A-8C show curve fits for allelic data for different ploidy hypotheses.
Figure 8B:
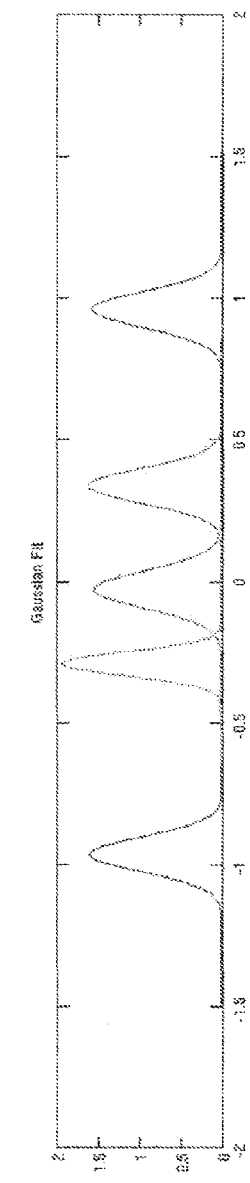
Figure 8C:
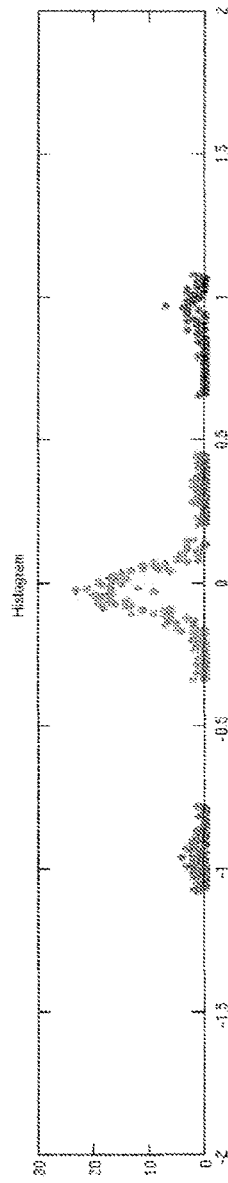

FIG. 6 and FIG. 7 present two graphs showing the clustering of the various contexts taken from actual data. FIG. 6 shows a plot of a first set of SNPs, with the normalized intensity of one channel output plotted against the other. FIG. 7 shows a plot of a second set of SNPs, with the normalized intensity of one channel output plotted against the other. The data presented in these two figures show that the data from the various contexts cluster well, and the hypotheses are clearly separable. Note that only chromosomes with confidence greater than about 0.9 were used for the training set. An example of the distribution of the distances can be seen in FIGS. 8A-8C, which show curve fits for allelic data for different ploidy hypotheses. FIG. 8A shows curve fits for allelic data for five different ploidy hypotheses using the Kernel method disclosed herein, FIG. 8B shows curve fits for allelic data for five different ploidy hypotheses using a Gaussian Fit disclosed herein, and FIG. 8C shows a histogram of the actual measured allelic data from one parental context, AA|BB–BB|AA, on channel X, as compared to the curve fits of all of the data. The ploidy state whose hypothesis best matches the actual measured allelic data is determined to be the actual ploidy state. This technique calls the ploidy state of the cell whose data is shown in FIGS. 6-8 as XX with confidence of about 0.999 or better. This method also made correct calls on single cells isolated from cell lines with known ploidy states.

Y Chromosome

In one embodiment of the present disclosure, the ploidy state of the Y chromosome may be determined as described as elsewhere in this disclosure, with the following modifications. In one embodiment it is possible to use the presence of parents technique, with appropriate modifications for the Y chromosome.

Let $F_i^e = 0$, $g_{ij} = \text{NaN}$. For $F_i^e = 1$, $g_{ij} = g^F$, i.e. the same as father. In another embodiment, it is possible to take into account possible error in father measurement:

$$P(g_{ij} \mid D, F) = P(g_{ij}) P(D_i^f \mid g_{ij}) \prod_{a=1, \ldots, k.} P(D_{ia}^e \mid g_{ij}, F_a^e) \prod_{a=1, \ldots, l} P(D_{ia}^s \mid g_{ij}, F_a^s)$$

where $P(g_{ij})$ is the population frequency on this snip, $P(D_i^f \mid g_{ij})$ is going to be 0/1. In one embodiment of the present disclosure, one may assume that there is no error on parents, in which case the Y chromosome algorithm is simple. In another embodiment, one may use an error model for the parents on Y chromosome, in which case $P(D_{ia}^e \mid g_{ij}, F_a^e)$, which is either simple if $F_a = 0$, or one may use an error model on the target, and on the Y chromosome.

XY Chromosome

For the "XY" chromosome, it is possible to use the same algorithm as for other autosomal chromosomes.

Z Chromosome

In one embodiment, the "Z" chromosome has been defined such that the alleles must be AB for males and AA/BB for females, determined by population frequency. In this embodiment, one may make the following modifications:

$$g_{ij} = \begin{cases} AB & F_j^e = 1 \\ AA & F_j^e = 0, p(A) = 1 \\ BB & F_j^e = 0, p(A) = 0 \end{cases}$$

In other respects the determination of the ploidy state of the Z chromosome may be done as described elsewhere in this disclosure.

Non-Parametric Technique

In another embodiment of the present disclosure, an approach termed the "non-parametric technique" may be used. This technique makes no assumptions on the distribution of the data. For a given set of SNPs, typically defined by a parental context, it builds the expected distribution based on hypothetical or empirical. The determination of the probabilities of the hypotheses is made by comparing the relationship between the observed distributions of the parental contexts to expected relationships between the distributions of the parental contexts. In one embodiment, the means, quartiles or quintiles of the observed distributions may be used to represent the distributions mathematically. In one embodiment, the expected relationships may be predicted using theoretical simulations, or they may be predicted by looking at empirical data from known sets of relationships for chromosomes with know ploidy states. In one embodiment, the theoretical distributions for a given parental context may be constructed by mixing the observed distributions from other parental contexts. The expected distributions for parental contexts under different hypotheses may be compared to the observed distributions of parental contexts, and only the distribution under the correct hypotheses is expected to match the observed distribution.

Outlined in this section is a method for computing posterior probabilities such as $P(H_i|\text{"data"})$ where $H_i$ is a hypothesis that is some combination of the expected sets of distributions for cases where a parent contributes 0, 1, or 2 chromosomes. For the cases where the parent contributes two chromosomes, there are two possible sub-cases: M1 copy error (unmatched copy error) (2a), or M2 copy error (matched copy error) (2b). This gives rise to 16 total hypotheses: four hypotheses for the father, multiplied by four for the mother. The case where either the mother or the father contributes at least one chromosome will be discussed first, and the case where a parent contributes no chromosomes will be discussed afterwards. Consider the following points:

(A) Under the parental contexts AB|AA and AA|AB, under the 8 parental chromosome contribution hypotheses where each parent contributes at least one chromosome, but not including the case where both parents contributed two chromosomes due to an M2 copy error, the distribution of the target genotypes can be separated into a distribution which can be computed empirically from the data. Furthermore, the distribution from the euploid state can be separated from the other hypotheses.

(B) If the distributions of the targets are different, there is a statistic T (formally here a random variable) that distinguishes them. The distribution of this statistic can be simulated by bootstrapping the distribution of the target under the parental contexts AB|AA and AA|AB. This produces an empirical p value under each hypothesis. The empirical p value for under the $i^{th}$ hypothesis will be denoted $\hat{p}_i$ and is defined as $$p_i = P(T \geq t | \text{hypothesis } i) \quad (1)$$

where T is the random variable and we see a realization of the statistic t. The distribution of T under hypothesis may be simulated with the bootstrap.

Empirical p values will produce posterior distributions of $P(H_i|\text{"data"})$ via formalizing "data" as the event (a random variable) $1_{T \geq t}$ with T defined on the joint probability space including all hypotheses and their sub hypotheses. This makes the above equation equivalent to $P(H_i|1_{T \geq t})$ which by Bayes' gives $$P(H_i | 1_{T \geq t}) = P(1_{T \geq t} | H_i) \frac{P(H_i)}{P(1_{T > t})}$$

$$= \hat{p}_i \frac{p_{H_i}}{p(T \geq t)}$$

where $\hat{p}_i$ as in Equation so that $P(I_{T \geq t}) = \Sigma_i \hat{p}_i p_{H_i}$ and $p_{H_i}$ is the prior on hypothesis i.

Denote (1,2a) as the case where the mother contributes 1 chromosome and the father contributes 2 under an m1 copy error. For the purpose of this discussion, assume an M1 copy error on a heterozygous locus implies AA, AB, and BB each occur with probability 1/3. In an M2 copy error, one chromosome is duplicated, so for a heterozygous locus, assume that AA and BB are seen each with probability 1/2.

Point (A) may be shown by investigating the distribution of the target under the different hypotheses. Note that (1,1) is the only case where $F_1 = F_2$ and both are mixtures of two different distributions. These may be simulated using polar and non-polar homozygous SNPs). This is a good technique for identifying trisomy, but it is difficult to calculate a confidence for because it is difficult to simulate its distribution. For example, consider the median statistic $T = \text{median}_{AABB}\{z_i^X - z_i^Y\} - \text{median}_{BBAA}\{w_i^X - w_i^Y\}$, which is good algorithmically at separating (1,1) from (2a/b,1) or (1,2a/b). Again, there is not a confidence associated, becuase its distribution under the hypothesis of (1,2a/b) is simulated in the same way as (1,1), namely, if there are $n_1$ cases of AA|BB and $n_2$ cases of BB|AA, the simulated distribution is a mixture distribution of AA|BB and BB|AA resampled with proportions $n_1/(n_1+n_2)$ and $n_2/(n_1+n_2)$. Thus, T compared to its simulated distribution under trisomy will be expected to be the same as T compared to its simulated distribution under euploid. The explanation below describes how to overcome this problem, with the unlikely exception of the case where each parent donates two copies of a given chromosome to the embryo.

In the explanation here, $F_1$ denotes the distribution of the target loci under the parental context AB|AA and $F_2$ the distribution of the target loci under the parental context AA|AB.

1. (1,1): the distributions $F_1 = F_2$ and $F_1$ is a mixture of ½AA and ½AB
2. (2b, 1): $F_1$ is a mixture of ½AAA and ½BBA. $F_2$ is a mixture of ½AAA and ½AAB.
3. (2a, 1): $F_1$ is a mixture of AAA ABA and BBA. I will be assuming the mixture is ⅓ for each although that may not be necessary for the method. $F_2$ is equal to a mixture of ½AAA and ½AAB.
4. (1,2b) $F_1$ is the same as $F_2$ in item 2 by symmetry and $F_2$ is the same as $F_1$ in item 2 by symmetry.
5. (1,2a) $F_1$ is the same as $F_2$ in item 3 by symmetry and $F_2$ is the same as $F_1$ in item 3 by symmetry.
6. (2a, 2b) $F_1$ is a mixture of ⅓ each of AAAA ABAA BBAA, $F_2$ is a mixture of ½ of AAAA AABB.
7. (2b, 2a) both $F_1$ is $F_2$ of the previous item and $F_2$ is $F_1$ of the previous item by symmetry.
8. (2a, 2a) $F_1$ is a mixture of ⅓ each of AAAA ABAA BBAA, $F_2$ equals $F_1$.
9. (2b, 2b) $F_1$ is a mixture of ½AAAA, ½BBAA. $F_2$ has the same distribution as $F_1$.

The algorithmic approach is as follows:

Find a good statistic $F_1$ of target channels under parent context AA|AB and a good statistic $F_2$ of target channels under parent context AB|AA. In one embodiment, let $t_1$ and $t_2$ be the means of $z_i^x - z_j^y$ under AA|AB and AB|AA, respectively.)

Under hypothesis i, produce empirical joint null distributions $(\hat{F}_1, \hat{F}_2)$ using a mixture of resampled data from polar homozygotes when possible, this is usually possible; otherwise use resampling of heterozygots.

Compare the joint distribution of $(t_1, t_2)$ to the empirical, which produces the empirical p value.

Compute the empirical p value as described in the first part of the document.

Classify according to maximum posterior probability and assign posterior probability to the call.

To increase the power of this procedure, one may include distributions $F_3$, $F_4$ which correspond to $F_1$ and $F_2$ but interchange the alleles A and B.

Now consider the cases where one parent contributes no chromosomes:
1. (0,0): $F_1$ and $F_2$ are noise, these could be simulated using any SNPs. In one embodiment, one could use the context AA|AA and BB|BB.
2. (0,1): $F_1$ is a ½ mixture of A and B $F_2$ is A
3. (0, 2a): $F_1$ is AA and $F_2$ is BB.
4. (0, 2b): $F_1$ is AA and $F_2$ is a mixture of AA AB BB.
5. (1,0) switch $F_1$ and $F_2$ from the case of (0,1) by symmetry.
6. (2a, 0) switch $F_1$ and $F_2$ from the case of (0,2a) by symmetry.
7. (2b, 0) switch $F_1$ and $F_2$ from the case of (0,2b) by symmetry.

Confidence Sketch for Non-Parametric Technique

The analysis of the algorithm is based on the idea that for the $i^{th}$ hypothesis, $H_i$, one may to compute the probability that some (another or the same) hypothesis $H_j$ is true given the data $P(H_i|data)$, which is equivalent to P("algorithm calls" $H_i$|data).:

Using priors, one may compute $P(data|H_i)$. In one embodiment, the algorithm may be simplified by using parental context 1. In another embodiment, all three contexts may be used. Therefore, one may write the analysis for the algorithm that calls euploid just when $$\frac{|\hat{p}_q - q|}{\partial_{p_q}}$$

is smaller than a threshold t where $\hat{p}_q$ is the re-estimate of q using only parental context 1 which is the polar homozygotes. Also, note the algorithm is calling ploidy state based on a modified thresholding scheme where the re-estimate $\hat{p}_q$ is compared to q and normalized based on the estimated standard error of $\sigma_{p_q}$. The algorithm works on autosomes and sex chromomomes in this way.

Fix a particular context and assume the $Z_i$ and $W_j$ have the following distribution:

$$Z_i = \mu_Z + \sigma_i^2 \epsilon_i \text{ and}$$

$$W_j = \mu_W + \sigma_j^2 \epsilon_j \quad (1)$$

where the $\epsilon_i$ and $\epsilon_j$ are assumed I.I.D., and $\{\sigma_i\}_{i=1}^n$ are constants. In practice, $z_1, \ldots z_{n_z}$ and $w_1, \ldots w_{n_w}$ are observed, realizations of the random variables $\{Z_i\}_{i=1}^{n_z}$ and $\{W_i\}_{i=1}^{n_w}$.

To analyze the quantile calling algorithm, assume the $q^{th}$ quantile of $\epsilon$ equals 0. This is without loss of generality because, for example, quantile calling is invariant under multiplicative scaling of the $Z_i$ and $W_j$ and adding a constant to all $Z_i$ and $W_j$.

Assume all $\sigma_i^2$ are equal to simplify and let $z_q$ be the $q^{th}$ quantile of the $Z_i$. Define/denote the $p_q$ by $$p_q s = P(W_j < z_q).$$

Then, under the euploid condition, since $\mu_Z = \mu_W$, for each $\epsilon_i$.

$$p_q = P(\mu_W + \epsilon_i < \mu_Z) = q.$$

where the $$P(\mu_W + \epsilon_i < \mu Z) = E(1\{\mu_W + \epsilon_i < \mu_Z\})$$

Outline of Probability Calculations

To understand the broad idea, consider a simplified case: suppose that the $\sigma_j$ are all the same and $z_q$, are known exactly. Then, the estimator of $p_q$, denoted $\hat{p}_q$ which in general is $$\hat{p}_q = \frac{1}{n_w} \sum_{i=1}^{n_w} 1_{W_i \leq \hat{z}_q}$$

would be simplified to $$\hat{p}_q = \frac{1}{n_w} \sum_{i=1}^{n_w} 1_{W_i \leq z_q}.$$

In this case, $W_i$ are i.i.d., $z_q$ is known and hence $\hat{p}_q$ is simply a mean of I.I.D. Bernouillis. This is an estimator which is simpler. The central limit theorem, which may be used to get exact information about the quality of approximation, says that $$\frac{\hat{p}_q - p_q}{\sigma_{p_q}} \quad (2)$$

has an approximate normal distribution.

This method may be used to get confidences because under euploidy, $p_q = q$ and under aneuploidy, if it is assumed that under the $j^{th}$ type aneuploidy there is a difference $\delta_j$ between $p_q$ and q, (j=1 means parental contributions (0,0), j=1 means parental contributions (1,0), ...), $p_q - q > \delta_j$. In one embodiment, the estimate of $\delta$ may be between 0 and 0.5.

Now assume, for simplicity, that all hypotheses are collapsed into $H_g$, the hypotheseis of euploidy and $H_a$ the hypotheseis of aneuploidy and denote $\delta$ as the smallest $\delta_j$.

$$\text{Define } \hat{z}_1 = \frac{\hat{p}_q - q}{\partial_{p_q}} \quad (3)$$

where $\hat{\sigma}_{p_q}$ is some estimate of $\sigma_{p_q}$, by bootstrap, or by the Bernouilli variance formula. The algorithm sets some threshold t and calls $H_e$ iff $|\hat{z}| < t$. Therefore, under euploidy, using the normal approximation, $\hat{z}$ has an approximate standard normal distribution so P($H_a$ called|euploid condition)=$P(|\hat{z}|<t) \cong P(|N(0,1)|<t) \cong 0.99$ for t=3. For t=3, this probability is approximately 0.99. Therefore: P($H_a$ called|euploid condition)$\cong 0.01$.

Conversely, under aneuploidy, $\hat{z}$ has a normal distribution with mean $$\frac{\delta}{\partial_{p_q}}$$

and a variance of 1. Typically, $\sigma_{p_q}$ is in the range of 0.01, therefore, of $\delta = (0.01)c$ for a constant c. In some embodiments c may be between about 1 and about 10, and another embodiment, c may be between about 10 and about 100.

$$P(H_a \text{ called|aneuploid condition}) = P(|\hat{z}|<t) \cong P(|N(5,1)|<t)$$

is small. For t=3, this probability is approximately (1−0.98)/2. Therefore, $$P(H_a \text{ called|aneuploid condition}) \cong 1 - 0.01.$$

Other possible expert techniques that may be used in the context of ploidy calling, and the list described in this disclosure is not meant to be exhaustive. Some further techniques are outlined below.

Allele Calling

In the context of PGD during IVF, there is a great need to determine the genome of the embryo. However, genotyping a single cell often results in a high rate of allele drop out, where many alleles give an incorrect or no reading. Accurate genetic data of the embryo is required to detect disease-linked genes with high confidence, and those determinations may then be used to select the best embryo for implantation. One embodiment of the present disclosure, described herein, involves inferring the genetic data of an embryo as accurately as possible. The obtained data may include the measured genetic data, across the same set of n SNPs, from a target individual, the father of the individual, and the mother of the individual. In one embodiment, the target individual may be an embryo. In one embodiment, the measured genetic data from one or more sperm from the father are also used. In one embodiment, the measured genetic data from one or more siblings of the target individual are also used. In one embodiment, the one or more siblings may also be considered target individuals. One way to increase the fidelity of allele calls in the genetic data of a target individual for the purposes of making clinically actionable predictions is described here. Note that the method may be modified to optimize for other contexts, such as where the target individual is not an embryo, where genetic data from only one parent is available, where neither, one or both of the parental haplotypes are known, or where genetic data from other related individuals is known and can be incorporated.

The present disclosures described in this and other sections in this document have the purpose of increasing the accuracy of the allele call at alleles of interest for a given number of SNPs, or alternately, decreasing the number of SNPs needed, and thus the cost, to achieve a given average level of accuracy for SNP calls. From these allele calls, especially those at disease linked or other phenotype linked genes, predictions can be made as to potential phenotypes. This information can be used to select (an) embryo(s) with desirable qualities for implantation. Since PGD is quite expensive, any novel technology or improvement in the PS algorithms, that allows the computation of the target genotype to be achieved at a given level of accuracy with less computing power, or fewer SNPs measured, will be a significant improvement over prior technology.

This disclosure demonstrates a number of novel methods that use measured parental and target genetic data, and in some cases sibling genetic data, to call alleles with a high degree of accuracy, where the sibling data may originate from born siblings, or other blastomeres, and where the target is a single cell. The method disclosed shows the reduction to practice, for the first time, of a method capable of accepting, as input, uncleaned genetic data measured from a plurality of related individuals, and also determining the most likely genetic state of each of the related individuals. In one embodiment, this may mean determining the identity of a plurality of alleles, as well as phasing any unordered data, while taking into account crossovers, and also the fact that all input data may contain errors.

Genetic data of a target can be described given the measured genetic data of the target, and of the parents of the target, where the genetic data of the parents is assumed to be correct. However, all measured genetic data is likely to contain errors, and a priori assumptions are likely to introduce biases and inaccuracies to the data. The method described herein shows how to determine the most likely genetic state for a set of related individuals where none of the genetic data is assumed to be true. The method disclosed herein allows the identity of each piece of measured genetic data to be influenced by the measured genetic data from each of the other related individuals. Thus, incorrectly measured parental data may be corrected if the statistical evidence indicates that it is incorrect.

In cases where the genetic data of an individual, or a set of related individuals, contains a significant amount of noise, or errors, the method disclosed herein makes use of the expected similarities between genetic data of those related individuals, and the information contained in the genetic data, to clean the noise in the target genome, along with errors that may be in the genetic data of the related individuals. This is done by determining which segments of chromosomes were involved in gamete formation and where crossovers occurred during meiosis, and therefore which segments of the genomes of related individuals are expected to be nearly identical to sections of the target genome. In certain situations this method can be used to clean noisy base pair measurements, but it also can be used to infer the identity of individual base pairs or whole regions of DNA that were not measured. In an embodiment, unordered genetic data may be used as input, for the target individual, and/or for one or more of the related individuals, and the output will contain the phased, cleaned genetic data for all of the individuals. In addition, a confidence can be computed for each reconstruction call made. Discussions concerning creating hypotheses, calculating the probabilities of the various hypotheses, and using those calculations to determine the most likely genetic state of the individual can be found elsewhere in this disclosure.

A highly simplified explanation of allele calling is presented first, making unrealistic assumptions in order to illustrate the concept of the present disclosure. A detailed statistical approach that can be applied to the technology of today is presented afterward.

A Simplified Example

Figure 9:
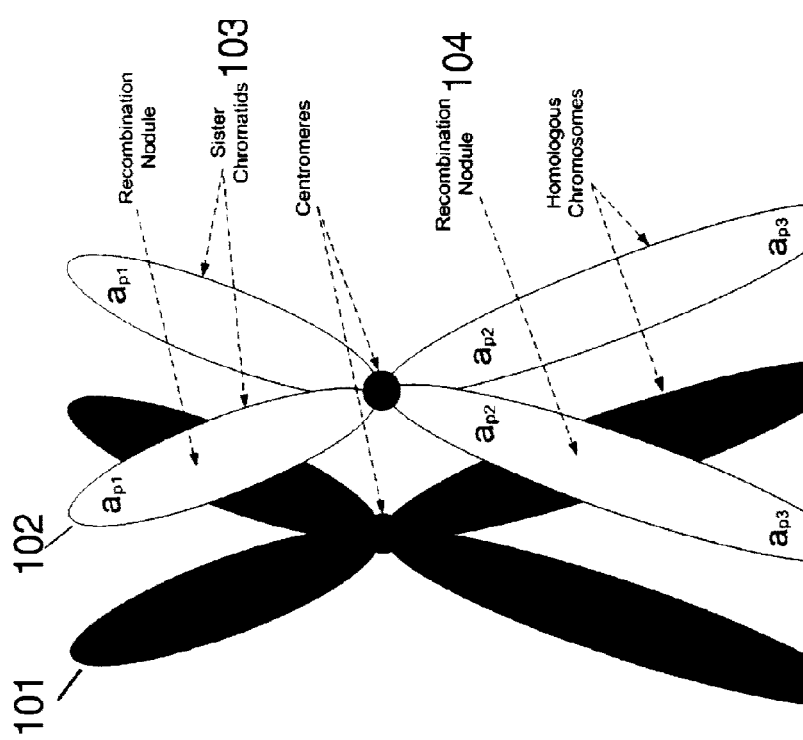
FIG. 9 shows a graphical representation of meiosis.

FIG. 9 illustrates the process of recombination that occurs during meiosis for the formation of gametes in a parent. The chromosome 101 from the individual's mother is shown in grey. The chromosome 102 from the individual's father is shown in white. During this interval, known as Diplotene, during Prophase I of Meiosis, a tetrad of four chromatids 103 is visible. Crossing over between non-sister chromatids of a homologous pair occurs at the points known as recombination nodules 104. For the purpose of illustration, the example will focus on a single chromosome, and three SNPs, which are assumed to characterize the alleles of three genes. For this discussion it is assumed that the SNPs may be measured separately on the maternal and paternal chromosomes. This concept can be applied to many SNPs, many alleles characterized by multiple SNPs, many chromosomes, and to the current genotyping technology where the maternal and paternal chromosomes cannot be individually isolated before genotyping.

Attention should be paid to the points of potential crossing over in between the SNPs of interest. The set of alleles of the three maternal genes may be described as $(a_{m1}, a_{m2}, a_{m3})$ corresponding to SNPs $(SNP_1, SNP_2, SNP_3)$. The set of alleles of the three paternal genes may be described as $(a_{p1}, a_{p2}, a_{p3})$ Consider the recombination nodules formed in FIG. 1, and assume that there is just one recombination for each pair of recombining chromatids. The set of gametes that are formed in this process will have gene alleles: $(a_{m1}, a_{m2}, a_{p3})$, $(a_{m1}, a_{p2}, a_{p3})$, $(a_{p1}, a_{m2}, a_{m3})$, $(a_{p1}, a_{p2}, a_{m3})$. In the case with no crossing over of chromatids, the gametes will have alleles $(a_{m1}, a_{m2}, a_{m3})$, $(a_{p1}, a_{p2}, a_{p3})$. In the case with two points of crossing over in the relevant regions, the gametes will have alleles $(a_{m1}, a_{p2}, a_{m3})$, $(a_{p1}, a_{m2}, a_{p3})$. These eight different combinations of alleles will be referred to as the hypothesis set of alleles, for that particular parent.

The measurement of the alleles from the embryonic DNA is typically noisy. For the purpose of this discussion take a single chromosome from the embryonic DNA, and assume that it came from the parent whose meiosis is illustrated in FIG. 9. The measurements of the alleles on this chromosome can be described in terms of a vector of indicator variables: $A = [A_1 \ A_2 \ A_3]^T$ where $A_1 = 1$ if the measured allele in the embryonic chromosome is $a_{m1}$, $A_1 = -1$ if the measured allele in the embryonic chromosome is $a_{p1}$, and $A_1 = 0$ if the measured allele is neither $a_{m1}$ or $a_{p1}$. Based on the hypothesis set of alleles for the assumed parent, a set of eight vectors may be created which correspond to all the possible gametes describe above. For the alleles described above, these vectors would be $a_1 = [1 \ 1 \ 1]^T$, $a_{2=[1\ 1\ -1]}^T$, $a_{3=[1\ -1\ 1]}^T$, $a_{4=[1\ -1\ -1]}^T$, $a_5 = [-1 \ 1 \ 1]^T$, $a_6 = [-1 \ 1 \ -1]^T$, $a_7 = [-1 \ -1 \ 1]^T$, $a_8 = [-1 \ -1 \ -1]^T$. In this highly simplified application of the system, the likely alleles of the embryo can be determined by performing a simple correlation analysis between the hypothesis set and the measured vectors:

$$i^* = \arg \max_i A^T a_i, i = 1 \ldots 8$$

Once $i^*$ is found, the hypothesis $a_i^*$ is selected as the most likely set of alleles in the embryonic DNA. This process may be repeated twice, with two different assumptions, namely that the embryonic chromosome came from the mother or the father. That assumption which yields the largest correlation $A^T a_i^*$ would be assumed to be correct. In each case a hypothesis set of alleles is used, based on the measurements of the respective DNA of the mother or the father.

Note that in one embodiment, those SNPs that are important due to their association with particular disease phenotypes may be referred to these as Phenotype-associated SNPs or PSNPs. In this embodiment, one may measure a large number of SNPs between the PSNPs, termed non-phenotype-associated SNPs (NSNPs), that are chosen a-priori (for example, for developing a specialized genotyping array) by selecting from the NCBI dbSNP database those RefSNPs that tend to differ substantially between individuals. Alternatively, the NSNPs between the PSNPs may be chosen for a particular pair of parents because the alleles for the parents are dissimilar. The use of the additional SNPs between the PSNPs enables one to determine with a higher level of confidence whether crossover occurs between the PSNPs. It is important to note that while different "alleles" are referred to in this notation, this is merely a convenience; the SNPs may not be associated with genes that encode proteins.

A More Thorough Treatment of the Allele Calling Method

In the simplified example given above, for the purpose of illustration of the concept, the assumption is made that the parental genotypes are phased and known correctly. However, in many cases, this assumption may not hold. For example, in the context of genotyping of embryos during IVF, typically the measured genetic data from the parents are uncleaned and unphased, any measured genetic data from sperm from the father are uncleaned, and the measured genetic data from one or more blastomeres, biopsied from one or more embryos are also are uncleaned and unphased. In theory, the knowledge of the uncleaned, unphased embryo derived genetic data can be used to phase and clean the parental genetic data. In addition, in theory the knowledge of the genotype of one embryo can be used to help clean and phase the genetic data of another embryo. In some cases, the measured genetic data of several sibling target individual may be correct at a given set of alleles, while the genetic data of a parent may be incorrect at those same alleles. In theory, the knowledge of the target individuals could be used to clean the data of the parent.

In some embodiments of the present disclosure disclosed herein, methods are described which allow the parental genetic data to be cleaned and phased using the knowledge of the genetic data of the target and other related individuals. In some embodiments, methods are described which allow the genetic data to be cleaned and phased also using the knowledge of the genetic data of sibling individuals. In an embodiment of the present disclosure, the genetic data of the parents, of the target individual, and of one or a plurality or related individuals, is used as input, where each piece of genetic data is associated with a confidence, and the knowledge of the expected similarities between all of the genotypes is used by an algorithm that selects the most likely genetic state of all of the related individuals, at once. The output of this algorithm, the most likely genetic state of the related individuals, may include the phased, cleaned genetic allele call data. In some embodiments of the present disclosure, there may be a plurality of target individuals, and these target individuals may be sibling embryos. In some embodiments of the present disclosure, the methods disclosed in the following section may be used to determine the statistical probability for an allelic hypothesis given the appropriate genetic data.

In some embodiments of the present disclosure, the target cell is a blastomere biopsied from an embryo in the context of preimplantation diagnosis (PGD) during in vitro fertilization (IVF). In some embodiments, the target cell may be a fetal cell, or extracellular fetal DNA in the context of non-invasive prenatal diagnosis. Note that this method may apply to situations in other contexts equally well. In some embodiments of the present disclosure, a computational device, such as a computer, is leveraged to execute any calculations that make up the method. In one embodiment of the present disclosure, the method disclosed herein uses genetic data from the target individual, from the parents of the target individual, and possibly from one or more sperm, and one or more sibling cells to recreate, with high accuracy, the genomic data on the embryo while accurately taking into account crossovers. In one embodiment of the present disclosure, the method may be used to recreate genetic data for target individuals at aneuploid, as well as euploid chromosomes. In one embodiment of the present disclosure, a method is described for determining the haplotypes of parent cells, given diploid parent data and diploid genetic data from one or more blastomeres or other sibling cells, and possibly, but not necessarily, one or more sperm cells from the father.

Practical Description of Allele Calling

In the following section, a description is given for a method for determining the genetic state of one or a series of target individuals. The description is made in the context of embryo genotype determination in the context of an IVF cycle, but it is important to note that the method described herein is equally well applicable other contexts, for other sets of related individuals, for example, in the context of non-invasive prenatal diagnosis, when the target individual is a fetus.

In the context of an IVF cycle, for a particular chromosome, the genotyping technique outputs data for n SNP locations, for k distinct targets (embryos or children) is made available by the genotyping technique. Each of the targets may have genotypes measured for one or more samples, and the measurements may be made on amplifications from a single cell, or from a small number of cells. For each SNP, each sample measurement consists of (X,Y) channel response (intensity) measurements. The X channel measures the strength of one (A) allele, and the Y channel measures the strength of the other (B) allele. If the measurements were completely accurate, on a particular SNP, an allele that is AA should have normalized (X,Y) intensities (arbitrary units are used) of (100,0), an allele that is AB should have intensities of (50,50) and an allele that is BB should have intensities of (0,100), and in this ideal case, it would be possible to derive exact allele values given the (X,Y) channel intensities. However, target single cell measurements are typically far from ideal, and it is not possible to determine, with high confidence, the true allele value given the raw channel responses.

Allele calling may be done for each chromosome separately. This discussion focuses on one particular autosomal chromosome with n SNPs. The first step is to define the nomenclature of the input data. The input data for the algorithm may be the uncleaned, unordered output data from genotyping array assays, it may be sequence data, it may be partially or fully processed genotype data, it may be known genotype data of an individual, or it may be any type of genetic data. The data may be arranged into target data, parental data, and sperm gametes, but this is not necessary. In the context of IVF, the target data would refer to genetic data measured from blastomeres biopsied from embryos, and it may also refer to genetic data measured from born siblings. The sperm data could refer to any data measured from a single set of chromosomes derived from a parent including sperm, polar bodies, unfertilized eggs or some other source of monosomic genetic matter. The data is arranged into various categories here for ease of understanding, but this is not necessary.

In this disclosure, the input data is labeled as follows: D refers to a set of genetic data from an individual. $D^T=(D^{T1}, \ldots, D^{Tk})$ refers to the genetic data from k distinct targets (embryos/children), $D^S=(D^{S1}, \ldots, D^{Sl})$ refers to the data from l distinct sperms, $(D^M)$ refers to the data from the mother, and $(D^F)$ refers to the data from the father. One may write $D=(D^T, D^S, D^M, D^F)$. Written differently, by SNPs, where the subscript i refers to the $i^{th}$ SNP in the set of data, $D=(D_1, \ldots, D_n)$, where $D_i=(D^T_i, D^S_i, D^M_i, D^F_i)$.

For k distinct targets, one may write $D^T_i=(D^{T1}_i, D^{T2}_i, \ldots, D^{Tk}_i)$. Each distinct target may have multiple resamples; a resample refers to an additional genotype reading made from a given sample. For the $j^{th}$ distinct target one may write $D^{Tj}_i=(DD^{Tj,1}_i, D^{Tj,2}_i, \ldots, D^{Tj,kj}_i)$ where kj=number of samples for target j. For $r^{th}$ resample of target j on SNP i, one will observe the set of channel intensities $D^{Tj,r}_i=(X^{Tj,r}_i, Y^{Tj,r}_i)$.

A plurality of sperm may be considered, and on SNP i one may write $D^S_i=(D^{S1}_i, D^{S2}_i, \ldots, D^{Sl}_i)$ for l distinct targets. Each distinct sperm may also have multiple resamples. Thus for jth distinct sperm $D^{Sj}_i=(D^{Sj,1}_i, D^{Sj,2}_i, \ldots, D^{Sj,lj}_i)$ where lj=number of resamples for sperm j. For the $r^{th}$ resample of sperm j on SNP i, one will observe the set of channel intensities $D^{Sj,r}_i=(X^{Sj,r}_i, Y^{Sj,r}_i)$.

The genetic data of the mother, on SNP i, is $D^M_i=(D^{M,1}_i, D^{M,2}_i, \ldots, D^{M,a}_i)$. The genetic data of the mother may also have multiple resamples, and for the $r^{th}$ resample of the mother on SNP i, one will observe the set of channel intensities $D^{M,r}_i=(X^{M,r}_i, Y^{M,r}_i)$.

The genetic data of the father, on SNP i, is $D^F_i=(D^{F,1}_i, D^{F,2}_i, \ldots, D^{F,b}_i)$ The genetic data of the father may also have multiple resamples, and for the $r^{th}$ resample of the father on SNP i, one will observe the set of channel intensities $D^{F,r}_i=(X^{F,r}_i, Y^{F,r}_i)$.

Hypothesis Nomenclature

For SNP i, and target j, the hypothesis consists of the mother and father origin hypothesis, i.e. $H^{Tj}_i=(H^{Tj}_{i,m}, H^{Tj}_{i,f})$, where $H^{Tj}_{i,m}$ in $\{1,2\}$, $H^{Tj}_{i,f}$ in $\{1,2\}$, each of which denote the parent haplotype of origin for each value. For sperm, there is only a father origin hypothesis, i.e. $H^{Sj}_i$ in $\{1,2\}$, indicating paternal origin (assuming normal sperm).

Overall, one may write:

$H=(H_1, \ldots, H_n)$, where $H_i=(H^T_i, H^S_i)$ and $H^T_i=(H^{T1}_i, H^{T2}_i, \ldots, H^{Tk}_i)$ and $H^S_i=(H^{S1}_i, H^{S2}_i, \ldots, H^{Sl}_i)$, where $H^{Tj}_i=(H^{Tj}_{i,m}, H^{Tj}_{i,f})$.

In an example with 3 embryos and 1 sperm, a particular SNP hypothesis for one chromosomal segment could be $((M_1,P_2),(M_2,P_2),(M_2,P_1)S_1)$. There are total of $2^{(2k+1)n}$ different hypotheses H.

Estimating Target Genotype Likelihood P(g|D)

For SNP i, target j, if P(g|D) is found, then the most likely $\vec{g}^j_i = \text{argmax}_g P(g|D)$, is picked as the allele call, with confidence $c^j_i = P(\vec{g}^j_i | D)$. In order to derive P(q|D), first let $g^M, g^F$ be possible ordered parents at the $i^{th}$ SNP, i.e. $g^M, g^F \in \{AA, AB, BA, BB\}$. $H_i$ is the full hypothesis on SNP i. Thus:

$$P(g^j_i | D) \sim \sum_{H_i} P(g^j_i, H_i, D) =$$

$$\sum_{H_i} P(D_{1,\ldots,i-1} | H_i) P(D_{i+1,\ldots n} | H_i) P(D_i, g^j_i, H_i)$$

Here the probability has been divided into the local probabilities of data on SNP i, $(D_i, g^j_i, H_i)$ and the probabilities for data on all other SNPs only depends on the hypothesis $H_i$:

$P(D_{1,\ldots,i-1} | H_i), P(D_{i+1,\ldots}, \vec{g}^j_i | H_i)$.

The Probability on SNP i $$P(D_i, g^j_i, H_i) = \sum_{g^M, g^F} P(D_i, g^j_i, H_i, g^M, g^F) =$$

$$= \sum_{g^M, g^F} P(D_i | g^j_i, g^M, g^F, H_i)$$

$$P(g^j_i | g^M, g^F, H^{Tj}_i) P(g^M) P(g^F) P(H_i)$$

$P(g^M), P(g^F)$ are allele frequencies of ordered parent alleles on this SNP. In particular if on this SNP P(A)=p, then $P(AA)=p^2$, $P(AB)=P(BA)=p(1-p)$, $P(BB)=(1-p)^2$. SNP allele frequencies may be estimated separately from large samples of genomic data.

$P(H_i)$ is generally same for all hypotheses $H_i$, and on all SNPs, except that for one of the SNPs (this may be chosen arbitraitly; one may choose a SNP in the middle, say on SNP n/2), the hypothesis is restricted and the first target may be called $(M_1, F_1)$ for uniqueness.

$P(g^j_i | g^M, g^F, H^{Tj}_i)$ is 1 or 0, depending on agreement of allele value $g^j_i$ and one produced by a combination of $g^M, g^F, H^{Tj}_i$, i.e. if we define $\alpha(g^M, g^F, h) =$ (an allele value uniquely defined by ordered mother allele $g^M$, an ordered father allele $g^F$, and parent hypothesis h), then:

$$P(g_i^j|g^M,g^F,H_i^{Tj})=I\{g_i^j=\alpha(g^M,g^F,H_i^{Tj})\}$$

Now $P(D_i|g_i^j,g^M,g^F,H_i)$ is the likelihood of data given particular allele values, since given parents $g^M,g^F$ and hypothesis $H_i$, allele values for all targets, sperms and parents are uniquely determined. In particular it can be rewritten as:

$$P(D_i|g_i^j,g^M,g^F,H_i)=P(D_i^T|g_i^j,g^M,g^F,H_i^T)P(D_i^S|g^F,H_i^S)$$
$$P(D_i^M|g^M)P(D_i^F|g^F)$$

For targets:

$$P(D_i^T|g_i^j,g^M,g^F,H_i^T)=P(D_i^{Tj}|g_i^j)\Pi_{u\neq j}P(D_i^{Tu}|\alpha(g^M,g^F,H_i^{Tu}))$$

For each target u, $P(D_i^{Tu}|g)$ is the product of likelihoods of all the resamples of that target $$P(D_i^{Tu}|g)=\Pi_r P^*(D_i^{Tu,r}|g).$$

Similarly for sperm:

$$P(D_i^S|g^F,H_i^S)=\Pi_u P(D_i^{Su}|\alpha(g^F,H_i^{Su}))$$

For each sperm u, $P(D_i^{Su}|g)$ is the product of likelihoods of all the resamples of that sperm $$P(D_i^{Su}|g)=\Pi_r P(D_i^{Su,r}|g).$$

For parents, one may multiply likelihoods of resamples for each parent:

$$P(D_i^M|g^M)=\Pi_r P(D_i^{M,r}|g^M), P(D_i^F|g^F)=\Pi_r P(D_i^{F,r}|g^F)$$

The piece of the likelihood P(D|g) remaining to be discussed, for each target, sperm and parent sample, is the estimated platform response model for that sample. This will be discussed later.

Probability on SNPs 1, ..., i−1

For all possible hypotheses on SNP i−1

$$P(D_{1,\ldots,i-1}|H_i) = \sum_{H_{i-1}} P(D_{1,\ldots,i-1}|H_{i-1})P(H_{i-1}|H_i)$$

$$= \sum_{H_{i-1}} P(D_{1,\ldots,i-2}|H_{i-1})P(D_{i-1}|H_{i-1})$$

$$P(H_{i-1}|H_i)$$

$P(D_1,\ldots,_{i-2}|H_{i-1})$, is i of the same format as $P(D_1,\ldots,_{i-1}|H_i)$, and can be calculated sequentially going up from SNP 1. In particular, define matrix $W^i$ as $W^i(h,1)=P(D_1,\ldots,_{i-1}|h)$ where h is the hypothesis on SNP i. Define matrix $PD^i$ as $PD^{i-1}(g,1)=P(D_{i-1}|g)$ where g is the hypothesis on SNP i−1. Define matrix $PC^i$ as $PC^i(h,g)=P(g|h)$, the probability of transition between hypotheses g to h, when going from SNP i−1 to i.

Then one may say $W^i=PC^i\times(PD^{i-1}\cdot W^{i-1})$ with the initial condition $W^1(g)=P(start@g)$. This may be an arbitrary chosen constant.

So, first find $W^2=PC^2X(PD^1\cdot W^1)$, then $W^3$, and so on, go up to $W^i$.

$PC^i(H_i,H_{i-1})=P(H_{i-1}|H_i)$ is the transition probability depending on the crossover probability between SNPs i−1, i. It is important to remember that hypothesis $H_i$ (and similarly for $H_{i-1}$) consists of the hypothesis for all targets and sperm $H_i=(H_i^T, H_i^S)$. Hypothesis $H_i^T=(H_i^{T1},H_i^{T2},\ldots,H_i^{Tk})$ are the target hypothesis for k targets, where each target hypothesis consists of the hypothesis of mother and father origin $H_i^{Tj}=(H_{i,m}^{Tj}, H_{i,f}^{Tj})$. Hypothesis $H_i^S=(H_i^{S1}, H_i^{S2}, \ldots, H_i^{Sl})$ is the father origin hypothesis for l sperms.

Then $P(H_{i-1}|H_i)=\Pi_j P(H_{i-1,m}^{Tj}|H_{i,m}^{Tj})\Pi_j P(H_{i-1,f}^{Tj}|H_{i,f}^{Tj})\Pi_j P(H_{i-1,f}^{Sj}|H_{i,f}^{Sj})$ where $P(g|h)=|_{1-cp}^{cp}{}_{g=h}^{g\neq h}$, and where cp is the crossover probability between SNPs i,i−1, and may be estimated separately from HAPMAP data.

$PD^{i-1}(H_{i-1})=P(D_{i-1}|H_{i-1})$ is the likelihood of data on SNP i−1, given this hypothesis $H_{i-1}$, and it may be calculated by summing over all the ordered parent allele values, similar to breakdown described earlier.

$$P(D_{i-1}|H_{i-1}) = \sum_{g^M,g^F} P(D_{i-1}|H_{i-1},g^M,g^F)$$

$$P(g^M)P(g^F)$$

$$= \sum_{g^M,g^F} P(D_{i-1}^T|g^M,g^F,H_{i-1}^T)P(D_{i-1}^S|g^F,H_{i-1}^S)$$

$$P(D_{i-1}^M|g^M)P(D_{i-1}^F|g^F)P(g^M)P(g^F)$$

Probability on SNPs i+1, ..., n

The derivation in this section is similar to the one above, except one goes from the other end, i.e. if we define $V^i(h,1)=P(D_{i+1},\ldots,_n|h)$, where h is the hypothesis on SNP I, then we have $V^i=PC^{i+1}\times(PD^{i+1}\cdot V^{i+1})$ With initial condition $V^n(g)=P(end@g)$ (just constant same for all, unimportant) So, first find $V^{n-1}=PC^n X(PD^n\cdot V^n)$, and so on, go down to $V^i$.

Estimating Hypothesis P(h|D)

Deriving the exact target or sperm hypothesis is not integral to allele calling, but it may be very useful for result checking and other applications. The procedure is very similar to deriving genotype probabilities, and is outlined here. In particular, for SNP i, target j, and hypothesis h defined as particular hypothesis for SNP i, target j, $$P(h|D) \sim \sum_{H_i,H_i^{T,j}=h} P(D,H_i) =$$

$$\sum_{H_i,H_i^{T,j}=h} P(D_{1,\ldots,i-1}|H_i)P(D_{i+1,\ldots,n}|H_i)P(D_i|H_i)P(H_i)$$

where all the pieces are derived as described elsewhere in this document.

Estimating Parent Genotype P(g|D)

Deriving exact parent genotype is not integral to allele calling, but it may be very useful for result checking and other applications. The procedure is very similar to deriving genotype probabilities, and is outlines here. In particular, for SNP i, target j, say mother genotype $g^M$ $$P(g^M|D) \sim \sum_{H_i,g^F} P(D,H_i,g^M,g^F) =$$

$$\sum_{H_i,g^F} P(D_{1,\ldots,i-1}|H_i)P(D_{i+1,\ldots,n}|H_i)P(D_i|H_i,g^M,g^F)P(H_i)P(g^M)P(g^F)$$

where all the pieces are derived as described elsewhere in this document.

Platform Response Model Estimating $P(D^T|g)$

The response model may be derived separately for each sample and each chromosome. The objective is to estimate of $P((X,Y)|g)$ where g=AA, AB, BB.

First make discrete the range of X,Y intensity response into T bins $B^X, B^Y$, derived as T equally spaced percentiles of data on respective channels (T<=20). Then one may estimate $P((X,Y)|g)$ as $P((X,Y)|g) \sim f(b_x, b_y, g)$ for $X \in b_x, Y \in b_y$, where $f(b_x, b_y, g)$ is estimated from data. In one embodiment the data may come from ILLUMINA SNP genotyping array output data and/or sequence data, which have different models. In other embodiments, the data may come from other genotyping arrays, from other sequencing methods, or other sources of genetic data.

Model for ILLUMINA Data

From parent data, estimate the mother genotype $G^M$, the father genotype $G^F$ and derive sample parent frequency $\hat{p}(gm, gf)$ for gm,gf=AA,AB,BB.

Estimate the allele frequency: $P(g) \sim \hat{f}(g) = \Sigma_{gm,gf} P(g|gm,gf) * \hat{p}(gm,gf)$.

Define $S^{AA}$ as the subset of SNPs of target data S for parental context AA|AA, i.e. $S^{AA} = \{S|G^M = AA, G^F = AA\}$, and $S^{BB}$ as the subset of SNPs of target data S for parental context BB|BB, i.e. $S^{BB} = \{S|G^M = BB, G^F = BB\}$. The allele value of SNPs in $S^{AA}$ has to be AA, and similarly BB for $S^{BB}$.

Joint Estimate

Define $f^{joint}(b_x, b_y, AA)$ as the joint bin sample frequency of intensities in $S^{AA}$. This is an estimate of $P((X,Y)|AA)$.

Define $f^{joint}(b_x, b_y, BB)$ as the joint bin sample frequency of intensities in $S^{BB}$. This is an estimate of $P((X,Y)|BB)$.

Define $f^{joint}(b_x, b_y, :)$ as the joint bin sample frequency of intensities in S. This is an estimate of $P((X,Y))$.

Now, it is know that $P((X,Y)) = \Sigma_{g=AA,AB,BB} P((X,Y)|g) * P(g)$ thus one may write $$P((X|Y)|AB) = \frac{P((X,Y)) - P(AA)P((X,Y)|AA) - P(BB)P((X,Y)|BB)}{1 - P(AA) - P(BB)}$$

and it is possible to estimate $P((X,Y)|AB)$ as follows:

$$f^{joint}(b_x, b_y, AB) = \frac{f^{joint}(b_x, b_y, :) - \hat{f}(AA) f^{joint}(b_x, b_y, AA) - \hat{f}(BB) f^{joint}(b_x, b_y, BB)}{1 - \hat{f}(AA) - \hat{f}(BB)}.$$

Now the function $f^{joint}(b_x, b_y, g)$ is one possible estimate of $P((X,Y)|g)$.

Marginal Estimate

Define $f^{marginal}(b_x, :, g,)$ as the marginal bin frequency of channel X intensities in $S^g$, for g=AA,BB,:. This is an estimate of $P(X|g)$.

Define $f^{marginal}(:, b_y, g)$ as the marginal bin frequency of channel Y intensities in $S^g$, for g=AA,BB,:. This is an estimate of $P(Y|g)$.

If channel responses are assumed to be independent (which they may not be), the for g=AA,BB, one may write:

$$f^{marginal}(b_x, b_y, g) = f^{marginal}(b_x, :, g) * f^{marginal}(:, b_y, g)$$

and as before:

$$f^{marginal}(b_x, b_y, AB) = \frac{f^{marginal}(b_x, b_y, :) - \hat{f}(AA) f^{marginal}(b_x, b_y, AA) - \hat{f}(BB) f^{marginal}(b_x, b_y, BB)}{1 - \hat{f}(AA) - \hat{f}(BB)}.$$

Now the function $f^{marginal}(b_x, b_y, g)$ is another possible estimate of $P((X,Y)|g)$.

Combined Estimate

In some embodiments, for example, where $f^{joint}$ is too data driven, and $f^{marginal}$ is too smooth, i.e. not taking into account channel dependency, it is possible to use the combined estimate, pooling these two to give:

$$f(b_x, b_y, g) = c * f^{joint}(b_x, b_y, g) + (1-c) * f^{marginal}(b_x, b_y, g),$$

for c=0.5 (an arbitrary constant).

Model for Sequence Data

Sequence data is different from data that originates from genotyping arrays. Each SNP is given separately, together with a plurality of locations around that SNP (typically about 400-500), by intensity for all 4 channels A,C,T,G. Sequence data also includes homozygous 'wild' call for all these locations. Typically, most of the non-SNP locations are homozygous and correspond to the wild call allele value. In one embodiment it is possible to assume that, for non-SNP locations, that wild call is the 'truth'.

Call non-SNP intensity data 'location data' may be used to help build the response model. Location data is of the format $LD = (LD_1, \ldots, LD_n)$ for n locations, where $LD_i = (L^A_i, L^C_i, L^T_i, L^G_i)$, A,C,T,G intensities on location i. Corresponding wild call data is $WD = (W_1, \ldots, W_n)$, where $W_i$ is one of the A,C,T,G. Ideally, if a particular allele, say C, is present at location i, the intensity value, $L^C_i$ should be high. If the allele value is not present, its intensity should be very low, ideally 0. So, for example for TT, one may expect to have intensities for (A, T, C, G)=(low, high, low, low)=(no, yes, no, no). For AT, one may expect to have (high, high, low, low)=(yes, yes, no, no).

With this in mind, it is possible to estimate $$f(b_x, b_y, AA) = YD(b_x) * ND(b_y), \text{(yes on } A, \text{no on } B)$$

$$f(b_x, b_y, AB) = YD(b_x) * YD(b_y), \text{(yes on } A, \text{yes on } B)$$

$$f(b_x, b_y, BB) = ND(b_x) * YD(b_y), \text{(no on } A, \text{yes on } B)$$

where YD(b) is the 'yes'/present' and ND(b) is the 'no/absent' one dimensional discrete bin distribution derived from data. YD may be derived from data in Yset={all channel intensities specified by wild call}. ND may be derived from data in Nset={all channel intensities NOT specified by wild call}. For example if the intensity at a particular location is (la, lc, lt, lg) and wild call is T, then lt will go toward Yset, and la, lc, lg will go toward Nset.

If channel independence and identical distribution (I.I.D. model) are assumed, then YD, ND distributions are just simple sample frequency of data in Yset, Nset respectively.

However, all four channels may be under- or over-amplified, and are therefore not independent. In one embodiment, it is possible to build a channel dependent and identical distribution (D.I.D. model), by scaling the intensity by maximum channel intensity on that location and applying I.I.D. model.

Results

This section discusses the results of this allele calling method, as applied to real data, operating on a set of measured genetic data from related individuals. The input data consisted of the raw output from an ILLUMINA Infinium genotyping array. The data included 22 chromosomes, of 1000 SNP each, for one set of related individuals, including:

2 children (with 2 samples for each child),
3 embryos (2 samples for each embryo), both parents (the mother and father, 2 genomic samples for each parent)

3 sperm (1 sample each)

Target Calling Results

The overall hit rates given for children, where genomic measurements made on bulk tissue samples were considered to be the 'truth', was 98.55%. The hit rate varied for different contexts, and is given in the table below:

| $(m_1m_2|f_1f_2)$ | hit rate | standard deviation |
|---|---|---|
| AA\|AA | 0.9963 | σ = 0.1822 |
| AA\|AB | 0.9363 | σ = 0.0933 |
| AA\|BB | 0.9995 | σ = 0.0365 |
| AB\|AA | 0.9665 | σ = 0.0956 |
| AB\|AB | 0.9609 | σ = 0.1313 |
| AB\|AA | 0.9635 | σ = 0.1013 |
| BB\|AA | 0.9980 | σ = 0.0337 |
| BB\|AB | 0.9940 | σ = 0.1088 |
| BB\|BB | 0.9983 | σ = 0.2112 |

The hit rate varied by chromosome, and ranged from about 99.5% to about 96.4%. Chromosomes 16, 19 and 22 were below about 98%. Note that hit rates for the father derived SNPs was about 99.82%, and the hit rates for mother derived SNPs was about 93.75%. The better hit rates for the father derived SNPs is due to better father phasing thanks to the phased genetic data available by genotyping sperm.

Figures 10A, 10B:
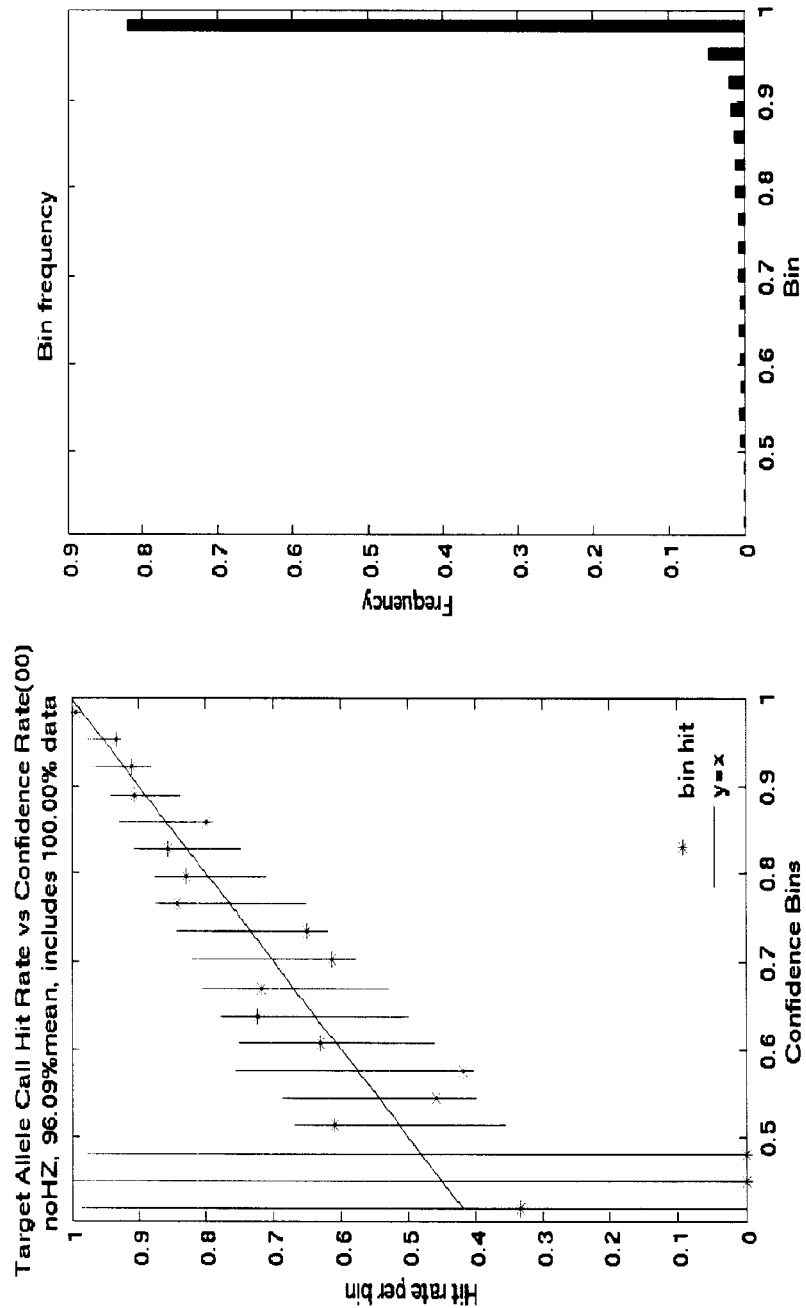
FIGS. 10A and 10B show the actual hit rate versus allele call confidence for large bins.
Figures 11A, 11B:
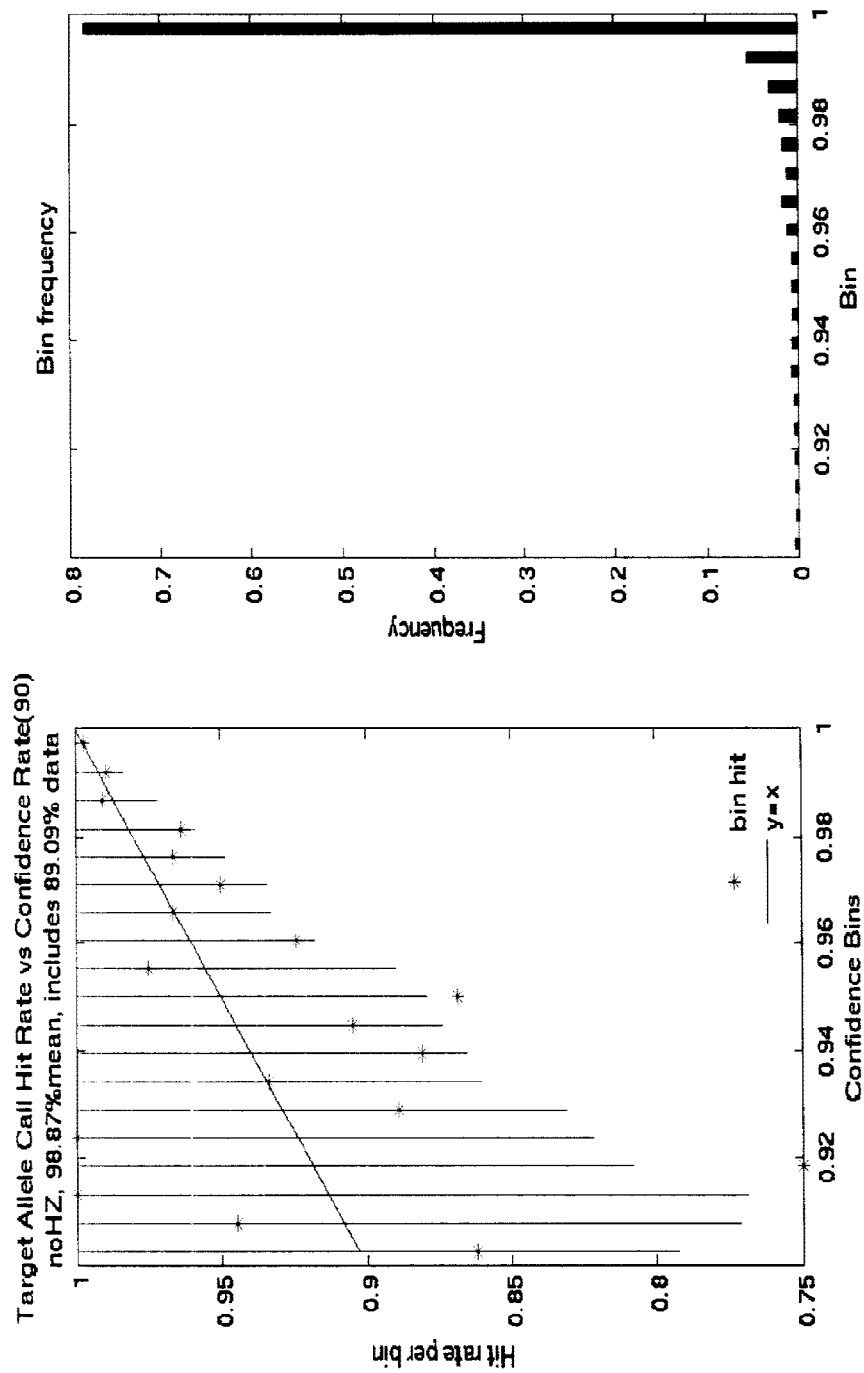
FIGS. 11A and 11B show the actual hit rate versus allele call confidence for small bins.

The hit rate by confidence bin refers to the hit rate for the set of allele calls that are predicted to have a certain confidence range. The overall hit rate for all of the data was about 98.55% hit rate. The hit rate for those allele calls which were predicted to have confidences above about 90%, which correspond to about 96.2% of all of the allele calls made, was 99.63%. The hit rate for those allele calls which were predicted to have confidences above about 99%, which corresponds to about 90.37% of the data, was about 99.9%. The hit rates for individual confidence bins indicate that the predicted confidences are quite accurate, within the limits of statistical significance. For example, for those allele calls with predicted confidences between about 80% and about 90% the actual hit rate was about 85.0%. For those allele calls with predicted confidences between about 70% and about 80% the actual hit rate was about 76.2%. For those allele calls with predicted confidences between about 96% and about 97% the actual hit rate was about 96.3%. For those allele calls with predicted confidences between about 94% and about 95% the actual hit rate was about 93.9%. For those allele calls with predicted confidences between about 99.1% and about 99.2% the actual hit rate was about 99.4%. For those allele calls with predicted confidences between about 99.8% and about 99.9% the actual hit rate was about 99.7%. FIGS. 10A and 10B and FIGS. 11A and 11B present plots of realized target hit rates, with confidence bars, versus hit rate as predicted by confidence. FIG. 10A plots the actual hit rate versus predicted confidence for bins that are three and a third percent wide, and FIG. 11A plots the actual hit rate versus predicted confidence for bins that are one half of a percent wide. The diagonal line represents the ideal case where the actual hit rate is equal to the predicted confidence. FIG. 10B shows the relative population of the various bin from FIG. 10A and FIG. 11B shows the relative population of the various bin from FIG. 11A. Bins with a higher population, or frequency, are expected to display a smaller deviation.

As a control, the same experiment was run, but genomic measurements taken on bulk data were used, instead of single cell measurements, as the measured target genetic data. In this case, the overall hit rate was about 99.88%.

Hypothesis Probability with Crossovers

The method described herein is also able to determine whether a crossover occurred in the formation of the embryos. Since the accuracy of the allele calling relies on knowing the identity of neighboring alleles, one may expect that allele calls near a crossover, where the neighboring alleles may not be from the same haplotype, the confidence of those calls may drop. This can be seen in FIGS. 12A-12B. FIG. 12A shows the plot of allele confidence averaged over the neighboring SNPs for a typical chromosome. Two different sets of data are graphed, E5 and E5GEN, obtained from the same target individual, but using different methods. A sharp drop in confidence around a certain region of a chromosome is indicative of a crossover having occurred at the location during the meiosis that gave rise to the target individual. FIG. 12B shows a line depiction of the chromosome, with a star to indicate the location where the ploidy hypothesis has determined a crossover occurred. In FIG. 12B, it is possible to observe two crossovers, a crossover on the mother homolog around SNP 350, and crossover on the father homolog around SNP 820. The line denoted "E5" was when the method is run on single cell target data, and the line denoted "E5GEN" was when the method was run on genomic data measured on bulk tissue. The fact that the lines are similar indicates that the method is accurately reconstructing the genetic data of the single cell target, specifically, the crossover location.

Varying the Number and Confidences of Input Data

In one embodiment of the present disclosure, it is possible to use genomic data from the mother and father, and single cell genetic data measured from the blastomeres and sperm. In another embodiment of the present disclosure, it is possible to also use genomic data from a born child from the same parents as additional information to help increase the accuracy of the determination of the single cell target genetic information. In one experiment, the genomic data of both parents along with the single cell genetic measurements from two embryo target cells were used, and the average hit rate on the target was about 95%. A similar experiment was run using the genomic data of both parents, the genomic data of one sibling, and the single cell target genetic information from one cell, and the added accuracy of the sibling genetic data increased the hit rate on the target cell to about 99%.

In another embodiment of the present disclosure, it is possible to use the genetic data from zero, one, two, three, four, or five or more sperm as input for the method. In some embodiments of the present disclosure is it possible to use the genetic data from one, two, three, four, five, or more than five sibling embryos as input for the method. In general, the bigger the number of inputs, the higher the accuracy of the target allele calls. Also, the higher the accuracy of the measurements of the inputs, the higher the accuracy of the target allele calls.

Another experiment was run with different sets of blastomere and sperm inputs, in the form of single cell blastomere measurements, and single cell sperm measurements. The table below shows that the higher the number of inputs, the higher the allele hit rate and hypothesis hit rate on the target. Note that "num sperms" indicates the number of sperm used in the determination; "num emb" corresponds to the total number of sibling embryos used in the determination, including the target; BK28 is a particular set of data.

|  | num sperms | | | |
|---|---|---|---|---|
| num emb | 0 | 1 | 2 | 3 |
| BK28 allele hit rate (%) | | | | |
| 3 | 93.46 | 95.18 | 95.69 | 95.86 |
| 4 | 95.06 | 96.13 | 96.59 | 96.75 |
| 5 | 95.93 | 96.67 | 97.00 | 97.15 |
| BK28 hypothesis hit rate (%) | | | | |
| 3 | 98.49 | 99.72 | 99.73 | 99.74 |
| 4 | 99.70 | 99.72 | 99.73 | 99.73 |
| 5 | 99.64 | 99.65 | 99.52 | 99.68 |

Amplification of Genomic DNA

Amplification of the genome can be accomplished by multiple methods including: ligation-mediated PCR (LM-PCR), degenerate oligonucleotide primer PCR (DOP-PCR), and multiple displacement amplification (MDA). Of the three methods, DOP-PCR reliably produces large quantities of DNA from small quantities of DNA, including single copies of chromosomes; this method may be most appropriate for genotyping the parental diploid data, where data fidelity is critical. MDA is the fastest method, producing hundred-fold amplification of DNA in a few hours; this method may be most appropriate for genotyping embryonic cells, or in other situations where time is of the essence.

Background amplification is a problem for each of these methods, since each method would potentially amplify contaminating DNA. Very tiny quantities of contamination can irreversibly poison the assay and give false data. Therefore, it is critical to use clean laboratory conditions, wherein pre- and post-amplification workflows are completely, physically separated. Clean, contamination free workflows for DNA amplification are now routine in industrial molecular biology, and simply require careful attention to detail.

Genotyping Assay and Hybridization

The genotyping of the amplified DNA can be done by many methods including MOLECULAR INVERSION PROBES (MIPs) such as AFFYMETRIX's GENFLEX TAG Array, microarrays such as AFFYMETRDCs 500K array or the ILLUMINA BEAD arrays, or SNP genotyping assays such as APPLIED BIOSCIENCE's TAQMAN assay. These are all examples of genotyping techniques. The AFFYMETRIX 500K array, MIPs/GENFLEX, TAQMAN and ILLUMINA assay all require microgram quantities of DNA, so genotyping a single cell with either workflow requires some kind of amplification.

In the context of pre-implantation diagnosis during IVF, the inherent time limitations are significant, and methods that can be run in under a day may provide a clear advantage. The standard MIPs assay protocol is a relatively time-intensive process that typically takes about 2.5 to three days to complete. Both the 500K arrays and the ILLUMINA assays have a faster turnaround: approximately 1.5 to two days to generate highly reliable data in the standard protocol. Both of these methods are optimizable, and it is estimated that the turn-around time for the genotyping assay for the 500 k array and/or the ILLUMINA assay could be reduced to less than 24 hours. Even faster is the TAQMAN assay which can be run in three hours. For all of these methods, the reduction in assay time may result in a reduction in data quality, however that is exactly what the disclosed present disclosure is designed to address.

Naturally, in situations where the timing is critical, such as genotyping a blastomere during IVF, the faster assays have a clear advantage over the slower assays, whereas in cases that do not have such time pressure, such as when genotyping the parental DNA before IVF has been initiated, other factors will predominate in choosing the appropriate method. Any techniques which are developed to the point of allowing sufficiently rapid high-throughput genotyping could be used to genotype genetic material for use with this method.

Methods for Simultaneous Targeted Locus Amplification and Whole Genome Amplification.

During whole genome amplification of small quantities of genetic material, whether through ligation-mediated PCR (LM-PCR), multiple displacement amplification (MDA), or other methods, dropouts of loci occur randomly and unavoidably. It is often desirable to amplify the whole genome nonspecifically, but to ensure that a particular locus is amplified with greater certainty. It is possible to perform simultaneous locus targeting and whole genome amplification.

In one embodiment, it is possible to combine the targeted polymerase chain reaction (PCR) to amplify particular loci of interest with any generalized whole genome amplification method. This may include, but is not limited to, preamplification of particular loci before generalized amplification by MDA or LM-PCR, the addition of targeted PCR primers to universal primers in the generalized PCR step of LM-PCR, and the addition of targeted PCR primers to degenerate primers in MDA.

Platform Response

There are many methods that may be used to measure genetic data. None of the methods currently known in the art are able to measure the genetic data with 100% accuracy, rather there are always errors, or statistical bias, in the data. It may be expected that the method of measurement will introduce certain statistically predictable biases into the measurement. It may be expected that certain sets of DNA, amplified by certain methods, and measured with certain techniques may result in measurements that are qualitatively and quantitatively different from other sets of DNA, that are amplified by other methods, and/or measured with different techniques. In some cases these errors may be due to the method of measurement. In some cases this error may be due to the state of the DNA. In some cases this bias may be due to the tendency of some types of DNA to respond differently to a given genetic measurement method. In some cases, the measurements may differ in ways that correlate with the number of cells used. In some cases, the measurements may differ based on the measurement technique, for example, which sequencing technique or array genotyping technique is used. In some cases different chromosomes may amplify to different extents. In some cases, certain alleles may be more or less likely to amplify. In some cases, the error, bias, or differential response may be due to a combination of factors. In many or all of these cases, the statistical predictability of these measurement differences, termed the 'platform response', may be used to correct for these factors, and can result in data that with an accuracy that is maximized, and where each measurement is associated with an appropriate confidence.

The platform response may be described as a mathematical characterization of the input/output characteristics of a genetic measurement platform, such as TAQMAN or Infinium. The input to the channel is the amplified genetic material with any annealed, fluorescently tagged genetic material. The channel output could be allele calls (qualitative) or raw numerical measurements (quantitative), depending on the context. For example, in the case in which the platform's raw numeric output is reduced to qualitative genotype calls, the platform response may consist of an error transition matrix that describes the conditional probability of seeing a particular output genotype call given a particular true genotype input. In one embodiment, in which the platform's output is left as raw numeric measurements, the platform response may be a conditional probability density function that describes the probability of the numerical outputs given a particular true genotype input.

In some embodiments of the present disclosure, the knowledge of the platform response may be used to statistically correct for the bias. In some embodiments of the present disclosure, the knowledge of the platform response may be used to increase the accuracy of the genetic data. This may be done by performing a statistical operation on the data that acts in the opposite manner as the biasing tendency of the measuring process. It may involve attaching the appropriate confidence to a given datum, such that when combined with other data, the hypothesis found to be most likely is indeed most likely to correspond to the actual genetic state of the individual in question.

Other Notes

As noted previously, given the benefit of this disclosure, there are more embodiments that may implement one or more of the systems, methods, and features, disclosed herein.

In some embodiments of the present disclosure, a statistical method may be used to remove the bias in the data due to the tendency for maternal alleles to amplify in a disproportionate manner to the other alleles. In some embodiments of the present disclosure, a statistical method may be used to remove the bias in the data due to the tendency for paternal alleles to amplify in a disproportionate manner to the other alleles. In some embodiments of the present disclosure, a statistical method may be used to remove the bias in the data due to the tendency for certain probes to amplify certain SNPs in a manner that is disproportionate to other SNPs.

Imagine the two dimensional space where the x-coordinate is the x channel intensity and the y-coordinate is the y channel intensity. In this space, one may expect that the context means should fall on the line defined by the means for contexts BB|BB and AA|AA. In some cases, it may be observed that the average contexts means do not fall on this lone, but are biased in a statistical manner; this may be termed "off line bias". In some embodiments of the present disclosure, a statistical method may be used to correct for the off line bias in the data.

In some cases splayed dots on the context means plot could be caused by translocation. If a translocation occurs, then one may expect to see abnormalities on the endpoints of the chromosome only. Therefore, if the chromosome is broken up into segments, and the context mean plots of each segment are plotted, then those segments that lie on the of a translocation may be expected to respond like a true trisomy or monosomy, while the remaining segments look disomic. In some embodiments of the present disclosure, a statistical method may be used to determine if translocation has occurred on a given chromosome by looking at the context means of different segments of the chromosome.

In some cases, it may be desirable to include a large number of related individuals into the calculation to determine the most likely genetic state of a target. In some cases, running the algorithm with all of the desired related individuals may not be feasible due to limits of computational power or time. The computing power needed to calculate the most likely allele values for the target increases exponentially with the number of sperm, blastomeres, and other input genotypes from related individuals. In one embodiment, these problems may be overcome by using a method termed "subsetting", where the computations may be divided into smaller sets, run separately, and then combined. In one embodiment of the present disclosure, one may have the genetic data of the parents along with that of ten embryos and ten sperm. In this embodiment, one could run several smaller sub-algorithms with, for example three embryos and three sperm, and then pool the results. In one embodiment the number of sibling embryos used in the determination may be from one to three, from three to five, from five to ten, from ten to twenty, or more than twenty. In one embodiment the number of sperm whose genetic data is known may be from one to three, from three to five, from five to ten, from ten to twenty, or more than twenty. In one embodiment each chromosome may be divided into two to five, five to ten, ten to twenty, or more than twenty subsets.

In one embodiment of the present disclosure, any of the methods described herein may be modified to allow for multiple targets to come from same target individual. This may improve the accuracy of the model, as multiple genetic measurements may provide more data with which the target genotype may be determined. In prior methods, one set of target genetic data served as the primary data which was reported, and the other served as data to double-check the primary target genetic data. This embodiment of the present disclosure is an improvement over prior methods in that a plurality of sets of genetic data, each measured from genetic material taken from the target individual, are considered in parallel, and thus both sets of target genetic data serve to help determine which sections of parental genetic data, measured with high accuracy, composes the embryonic genome. In one embodiment of the present disclosure, the target individual is an embryo, and the different genotype measurements are made on a plurality of biopsied blastomeres. In another embodiment, one could also use multiple blastomeres from different embryos, from the same embryo, cells from born children, or some combination thereof.

In some embodiments of the present disclosure, the methods described herein may be used to determine the genetic state of a developing fetus prenatally and in a non-invasive manner. The source of the genetic material to be used in determining the genetic state of the fetus may be fetal cells, such as nucleated fetal red blood cells, isolated from the maternal blood. The method may involve obtaining a blood sample from the pregnant mother. The method may involve isolating a fetal red blood cell using visual techniques, based on the idea that a certain combination of colors are uniquely associated with nucleated red blood cell, and a similar combination of colors is not associated with any other present cell in the maternal blood. The combination of colors associated with the nucleated red blood cells may include the red color of the hemoglobin around the nucleus, which color may be made more distinct by staining, and the color of the nuclear material which can be stained, for example, blue. By isolating the cells from maternal blood and spreading them over a slide, and then identifying those points at which one sees both red (from the Hemoglobin) and blue (from the nuclear material) one may be able to identify the location of nucleated red blood cells. One may then extract those nucleated red blood cells using a micromanipulator, use genotyping and/or sequencing techniques to measure aspects of the genotype of the genetic material in those cells. In one embodiment of the present disclosure, one may then use an informatics based technique such as the ones described in this disclosure to determine whether or not the cells are in fact fetal in origin. In one embodiment of the present disclosure, one may then use an informatics based technique such as the ones described in this disclosure to determine the ploidy state of one or a set of chromosomes in those cells. In one embodiment of the present disclosure, one may then use an informatics based technique such as the ones described in this disclosure to determine the genetic state of the cells. When applied to the genetic data of the cell, PARENTAL SUPPORT™ could indicate whether or not a nucleated red blood cell is fetal or maternal in origin by identifying whether the cell contains one chromosome from the mother and one from the father, or two chromosomes from the mother.

In one embodiment, one may stain the nucleated red blood cell with a die that only fluoresces in the presence of fetal hemoglobin and not maternal hemoglobin, and so remove the ambiguity between whether a nucleated red blood cell is derived from the mother or the fetus. Some embodiments of the present disclosure may involve staining or otherwise marking nuclear material. Some embodiments of the present disclosure may involve specifically marking fetal nuclear material using fetal cell specific antibodies. Some embodiments of the present disclosure may involve isolating, using a variety of possible methods, one or a number of cells, some or all of which are fetal in origin. Some embodiments of the present disclosure may involve amplifying the DNA in those cells, and using a high throughput genotyping microarray, such as the ILLUMINA INFINIUM array, to genotype the amplified DNA. Some embodiments of the present disclosure may involve using the measured or known parental DNA to infer the more accurate genetic data of the fetus. In some embodiments, a confidence may be associated with the determination of one or more alleles, or the ploidy state of the fetus. Some embodiments of the present disclosure may involve staining the nucleated red blood cell with a die that only fluoresces in the presence of fetal hemoglobin and not maternal hemoglobin, and so remove the ambiguity between whether a nucleated red blood cell is derived from the mother or the fetus.

There are many other ways to isolate fetal cells from maternal blood, or fetal DNA from maternal blood, or to enrich samples of fetal genetic material in the presence of maternal genetic material. Some of these methods are listed here, but this is not intended to be an exhaustive list. Some appropriate techniques are listed here for convenience: using fluorescently or otherwise tagged antibodies, size exclusion chromatography, magnetically or otherwise labeled affinity tags, epigenetic differences, such as differential methylation between the maternal and fetal cells at specific alleles, density gradient centrifugation succeeded by CD45/14 depletion and CD71-positive selection from CD45/14 negative-cells, single or double Percoll gradients with different osmolalities, or galactose specific lectin method.

One embodiment of the present disclosure could be as follows: a pregnant woman wants to know if her fetus is afflicted with Down Syndrome, and if it will suffer from Cystic Fibrosis. A doctor takes her blood, and stains the hemoglobin with one marker so that it appears clearly red, and stains nuclear material with another marker so that it appears clearly blue. Knowing that maternal red blood cells are typically anuclear, while a high proportion of fetal cells contain a nucleus, he is able to visually isolate a number of nucleated red blood cells by identifying those cells that show both a red and blue color. The doctor picks up these cells off the slide with a micromanipulator and sends them to a lab which amplifies and genotypes ten individual cells. By looking at the genetic measurements, the PARENTAL SUPPORT™ is able to determine that six of the ten cells are maternal blood cells, and four of the ten cells are fetal cells. If a child has already been born to a pregnant mother, PARENTAL SUPPORT™ can also be used to determine that the fetal cell is distinct from the cells of the born child by making reliable allele calls on the fetal cells and showing that they are dissimilar to those of the born child. The genetic data measured from the fetal cells is of very poor quality, containing many allele drop outs, due to the difficulty of genotyping single cells. The clinician is able to use the measured fetal DNA along with the reliable DNA measurements of the parents to infer the genome of the fetus with high accuracy using PARENTAL SUPPORT. The clinician is able to determine both the ploidy state of the fetus, and the presence or absence of a plurality of disease-linked genes of interest.

In some embodiments of the present disclosure, a plurality of parameters may be changed without changing the essence of the present disclosure. For example, the genetic data may be obtained using any high throughput genotyping platform, or it may be obtained from any genotyping method, or it may be simulated, inferred or otherwise known. A variety of computational languages could be used to encode the algorithms described in this disclosure, and a variety of computational platforms could be used to execute the calculations. For example, the calculations could be executed using personal computers, supercomputers, a massively parallel computing platform, or even non-silicon based computational platforms such as a sufficiently large number of people armed with abacuses.

Some of the math in this disclosure makes hypotheses concerning a limited number of states of aneuploidy. In some cases, for example, only zero, one or two chromosomes are expected to originate from each parent. In some embodiments of the present disclosure, the mathematical derivations can be expanded to take into account other forms of aneuploidy, such as quadrosomy, where three chromosomes originate from one parent, pentasomy, etc., without changing the fundamental concepts of the present disclosure.

In some embodiments of the present disclosure, a related individual may refer to any individual who is genetically related, and thus shares haplotype blocks with the target individual. Some examples of related individuals include: biological father, biological mother, son, daughter, brother, sister, half-brother, half-sister, grandfather, grandmother, uncle, aunt, nephew, niece, grandson, granddaughter, cousin, clone, the target individual himself/herself/itself, and other individuals with known genetic relationship to the target. The term 'related individual' also encompasses any embryo, fetus, sperm, egg, blastomere, blastocyst, or polar body derived from a related individual.

In some embodiments of the present disclosure, the target individual may refer to an adult, a juvenile, a fetus, an embryo, a blastocyst, a blastomere, a cell or set of cells from an individual, or from a cell line, or any set of genetic material. The target individual may be alive, dead, frozen, or in stasis.

In some embodiments of the present disclosure, where the target individual refers to a blastomere that is used to diagnose an embryo, there may be cases caused by mosaicism where the genome of the blastomere analyzed does not correspond exactly to the genomes of all other cells in the embryo.

In some embodiments of the present disclosure, it is possible to use the method disclosed herein in the context of cancer genotyping and/or karyotyping, where one or more cancer cells is considered the target individual, and the non-cancerous tissue of the individual afflicted with cancer is considered to be the related individual. The non-cancerous tissue of the individual afflicted with the target could provide the set of genotype calls of the related individual that would allow chromosome copy number determination of the cancerous cell or cells using the methods disclosed herein.

In some embodiments of the present disclosure, as all living or once living creatures contain genetic data, the methods are equally applicable to any live or dead human, animal, or plant that inherits or inherited chromosomes from other individuals.

It is also important to note that the embryonic genetic data that can be generated by measuring the amplified DNA from one blastomere can be used for multiple purposes. For example, it can be used for detecting aneuploidy, uniparental disomy, sexing the individual, as well as for making a plurality of phenotypic predictions based on phenotype-associated alleles. Currently, in IVF laboratories, due to the techniques used, it is often the case that one blastomere can only provide enough genetic material to test for one disorder, such as aneuploidy, or a particular monogenic disease. Since the method disclosed herein has the common first step of measuring a large set of SNPs from a blastomere, regardless of the type of prediction to be made, a physician, parent, or other agent is not forced to choose a limited number of disorders for which to screen. Instead, the option exists to screen for as many genes and/or phenotypes as the state of medical knowledge will allow. With the disclosed method, one advantage to identifying particular conditions to screen for prior to genotyping the blastomere is that if it is decided that certain loci are especially relevant, then a more appropriate set of SNPs which are more likely to co-segregate with the locus of interest, can be selected, thus increasing the confidence of the allele calls of interest.

In some embodiments, the systems, methods and techniques of the present disclosure may be used to decrease the chances that an implanted embryo, obtained by in vitro fertilization, undergoes spontaneous abortion.

In some embodiments of the present disclosure, the systems, methods, and techniques of the present disclosure may be used to in conjunction with other embyro screening or prenatal testing procedures. The systems, methods, and techniques of the present disclosure are employed in methods of increasing the probability that the embryos and fetuses obtain by in vitro fertilization are successfully implanted and carried through the full gestation period. Further, the systems, methods, and techniques of the present disclosure are employed in methods that may decrease the probability that the embryos and fetuses obtained by in vitro fertilization and that are implanted are not specifically at risk for a congenital disorder.

In some embodiments, the systems, methods, and techniques of the present disclosure are used in methods to decrease the probability for the implantation of an embryo specifically at risk for a congenital disorder by testing at least one cell removed from early embryos conceived by in vitro fertilization and transferring to the mother's uterus only those embryos determined not to have inherited the congenital disorder.

In some embodiments, the systems, methods, and techniques of the present disclosure are used in methods to decrease the probability for the implantation of an embryo specifically at risk for a chromosome abnormality by testing at least one cell removed from early embryos conceived by in vitro fertilization and transferring to the mother's uterus only those embryos determined not to have chromosome abnormalities.

In some embodiments, the systems, methods, and techniques of the present disclosure are used in methods to increase the probability of implantation of an embryo that was obtained by in vitro fertilization, is transferred, and that is at a reduced risk of carrying a congenital disorder.

In some embodiments, the congenital disorder is a malformation, neural tube defect, chromosome abnormality, Down's syndrome (or trisomy 21), Trisomy 18, spina bifida, cleft palate, Tay Sachs disease, sickle cell anemia, thalassemia, cystic fibrosis, Huntington's disease, Cri du chat syndrome, and/or fragile X syndrome. Chromosome abnormalities may include, but are not limited to, Down syndrome (extra chromosome 21), Turner Syndrome (45X0) and Klinefelter's syndrome (a male with 2X chromosomes).

In some embodiments, the malformation may be a limb malformation. Limb malformations may include, but are not limited to, amelia, ectrodactyl), phocomelia, polymelia, polydactyl), syndactyl), polysyndactyl), oligodactyl), brachydactyl), achondroplasia, congenital aplasia or hypoplasia, amniotic band syndrome, and cleidocranial dysostosis.

In some embodiments, the malformation may be a congenital malformation of the heart. Congenital malformations of the heart may include, but are not limited to, patent ductus arteriosus, atrial septal defect, ventricular septal defect, and tetralogy of fallot.

In some embodiments, the malformation may be a congenital malformation of the nervous system. Congenital malformations of the nervous system include, but are not limited to, neural tube defects (e.g., spina bifida, meningocele, meningomyelocele, encephalocele and anencephaly), Arnold-Chiari malformation, the Dandy-Walker malformation, hydrocephalus, microencephaly, megencephaly, lissencephaly, polymicrogyria, holoprosencephaly, and agenesis of the corpus callosum.

In some embodiments, the malformation may be a congenital malformation of the gastrointestinal system. Congenital malformations of the gastrointestinal system include, but are not limited to, stenosis, atresia, and imperforate anus.

In some embodiments, the systems, methods, and techniques of the present disclosure are used in methods to increase the probability of implanting an embryo obtained by in vitro fertilization that is at a reduced risk of carrying a predisposition for a genetic disease.

In some embodiments, the genetic disease is either monogenic or multigenic. Genetic diseases include, but are not limited to, Bloom Syndrome, Canavan Disease, Cystic fibrosis, Familial Dysautonomia, Riley-Day syndrome, Fanconi Anemia (Group C), Gaucher Disease, Glycogen storage disease 1a, Maple syrup urine disease, Mucolipidosis IV, Niemann-Pick Disease, Tay-Sachs disease, Beta thalessemia, Sickle cell anemia, Alpha thalessemia, Beta thalessemia, Factor XI Deficiency, Friedreich's Ataxia, MCAD, Parkinson disease-juvenile, Connexin26, SMA, Rett syndrome, Phenylketonuria, Becker Muscular Dystrophy, Duchennes Muscular Dystrophy, Fragile X syndrome, Hemophilia A, Alzheimer dementia-early onset, Breast/Ovarian cancer, Colon cancer, Diabetes/MODY, Huntington disease, Myotonic Muscular Dystrophy, Parkinson Disease-early onset, Peutz-Jeghers syndrome, Polycystic Kidney Disease, Torsion Dystonia Combinations of the Aspects of the Present Disclosure As noted previously, given the benefit of this disclosure, there are more aspects and embodiments that may implement one or more of the systems, methods, and features, disclosed herein. Below is a short list of examples illustrating situations in which the various aspects of the present disclosure can be combined in a plurality of ways. It is important to note that this list is not meant to be comprehensive; many other combinations of the aspects, methods, features and embodiments of this present disclosure are possible.

The key to one aspect of the present disclosure is the fact that ploidy determination techniques that make use of phased parental data of the target may be much more accurate than techniques that do not make use of such data. However, in the context of WF, phasing the measured genotypic data obtained from bulk parental tissue is nontrivial. One method to determine the phased parental data from the unphased parental genetic data, along with the unphased genetic data from one or more embryos, zero or more siblings, and zero or more sperm is described in this disclosure. This method for phasing parental data assumes that the embryo genetic data is euploid at a given chromosome. Of course it may not be possible to determine the ploidy state at the given chromosome, to ensure euploidy, using a method that requires phased parental data as input, before that genetic data has been phased, presenting a boot strapping problem.

In some embodiments of the present disclosure, a method is disclosed herein wherein a technique for ploidy state determination is used to make a preliminary determination as to the ploidy state at a given chromosome for a set of cells derived from one or more embryos. Then, the method described herein for determining the phased parental data may be executed, using only the data from embryonic chromosomes that have been determined, with high confidence using the preliminary method, to be euploid. Once the parental data has been phased, then the ploidy state determination method that requires phased parental data may be used to give high accuracy ploidy determinations. The output from this method may be used on its own, or it may be combined with other ploidy determination methods.

Some of the expert techniques for copy number calling described in this disclosure, for example the "presence of homologues" technique, rely on phased parental genomic data. Some methods to phase data, such as some of those described in this disclosure, operate on the assumption that the input data is from euploid genetic material. When the target is a fetus or an embryo, it is particularly likely that one or more chromosomes are not euploid. In one embodiment of the present disclosure, one or a set of ploidy determination techniques that do not rely on phased parental data may be used to determine which chromosomes are euploid, such that genetic data from those euploid chromosomes may be used as part of an allele calling algorithm that outputs phased parental data, which may then be used in the copy number calling technique that requires phased parental data.

In one embodiment of the present disclosure, a method to determine the ploidy state of at least one chromosome in a target individual includes obtaining genetic data from the target individual, and from both parent of the target individual, and from one or more siblings of the target individual, wherein the genetic data includes data relating to at least one chromosome; determining a ploidy state of the at least one chromosome in the target individual and in the one or more siblings of the target individual by using one or more expert techniques, wherein none of the expert techniques requires phased genetic data as input; determining phased genetic data of the target individual, and of the parents of the target individual, and of the one or more siblings of the target individual, using an informatics based method, and the obtained genetic data from the target individual, and from the parents of the target individual, and from the one or more siblings of the target individual that were determined to be euploid at that chromosome; and redetermining the ploidy state of the at least one chromosome of the target individual, using one or more expert techniques, at least one of which requires phased genetic data as input, and the determined phased genetic data of the target individual, and of the parents of the target individual, and of the one or more siblings of the target individual. In an embodiment, the ploidy state determination can be performed in the context of in vitro fertilization, and where the target individual is an embryo. The determined ploidy state of the chromosome on the target individual can be used to make a clinical decision about the target individual.

First, genetic data may be obtained from the target individual and from the parents of the target individual, and possibly from one or more individuals that are siblings of the target individual. This genetic data from individuals may be obtained in a number of ways, and these are described elsewhere in this disclosure. The target individual's genetic data can be measured using tools and or techniques taken from a group including, but not limited to, MOLECULAR INVERSION PROBES (MIP), Genotyping Microarrays, the TAQMAN SNP Genotyping Assay, the ILLUMINA Genotyping System, other genotyping assays, fluorescent in-situ hybridization (FISH), sequencing, other high through-put genotyping platforms, and combinations thereof. The target individual's genetic data can be measured by analyzing substances taken from a group including, but not limited to, one or more diploid cells from the target individual, one or more haploid cells from the target individual, one or more blastomeres from the target individual, extra-cellular genetic material found on the target individual, extra-cellular genetic material from the target individual found in maternal blood, cells from the target individual found in maternal blood, genetic material known to have originated from the target individual, and combinations thereof. The related individual's genetic data can be measured by analyzing substances taken from a group including, but not limited to, the related individual's bulk diploid tissue, one or more diploid cells from the related individual, one or more haploid cells taken from the related individual, one or more embryos created from (a) gamete(s) from the related individual, one or more blastomeres taken from such an embryo, extra-cellular genetic material found on the related individual, genetic material known to have originated from the related individual, and combinations thereof.

Second, a set of at least one ploidy state hypothesis may be created for one or more chromosome of the target individual and of the siblings. Each of the ploidy state hypotheses may refer to one possible ploidy state of the chromosome of the individuals.

Third, using one or more of the expert techniques, such as those discussed in this disclosure, a statistical probability may be determined for each ploidy state hypothesis in the set. In this step, the expert techniques is an expert technique that does not required phased genetic data as input. Some examples of expert techniques that do not require phased genetic data as input include, but are not limited to, the permutation technique, the whole chromosome mean technique, and the presence of parents technique. The mathematics underlying the various appropriate expert techniques is described elsewhere in this disclosure.

Fourth, if more than one expert method was used in the third step, then the set of determined probabilities may then be combined and normalized. The set of the products of the probabilities for each hypothesis in the set of hypotheses is then output as the combined probabilities of the hypotheses.

Fifth, the most likely ploidy state for the target individual, and for each of the sibling individual(s), is determined to be the ploidy state that is associated with the hypothesis whose probability is the greatest.

Sixth, an informatics based method, such as the allele calling method disclosed in this document, or other aspects of the PARENTAL SUPPORT™ method, along with unordered parental genetic data, and the genetic data of siblings that were found to be euploid in the fifth step, at that chromosome, may be used to determine the most likely allelic state of the target individual, and of the sibling individuals. In some embodiments, the target individuals may be treated the same, algorithmically, as the siblings. In some embodiments, the allelic state of a sibling may be determined by letting the target individual act as a sibling, and the sibling act as a target. In some embodiments, the informatics based method should also output the allelic state of the parents, including the haplotypic genetic data. In some embodiments of the present disclosure the informatics based method used may also determine the most likely phased genetic state of the parent(s) and of the other siblings.

Seventh, a new set of at least one ploidy state hypothesis may be created for one or more chromosome of the target individual and of the siblings. As before, each of the ploidy state hypotheses may refer to one possible ploidy state of the chromosome of the individuals.

Eighth, using one or more of the expert techniques, such as those discussed in this disclosure, a statistical probability may be determined for each ploidy state hypothesis in the set. In this step, at least one of the expert techniques is an expert technique that does require phased genetic data as input, such as the 'presence of homologs' technique.

Ninth, the set of determined probabilities may then be combined as described in the fourth step.

Lastly, the most likely ploidy state for the target individual, at that chromosome, is determined to be the ploidy state that is associated with the hypothesis whose probability is the greatest. In some embodiments, the ploidy state will only be called if the hypothesis whose probability is the greatest exceeds a certain threshold of confidence and/or probability.

In one embodiment of this method, in the third step, the following three expert techniques can be used in the initial ploidy state determination: the permutation technique, the whole chromosome mean technique, and the presence of parents technique. In one embodiment of the present disclosure, in the eighth step, the following set of expert techniques can be used in the final ploidy determination: the permutation technique, the whole chromosome mean technique, the presence of parents technique, and the presence of homologues technique. In some embodiments of the present disclosure different sets of expert techniques may be used in the third step. In some embodiments of the present disclosure different sets of expert techniques may be used in the eighth step. In one embodiment of the present disclosure, it is possible to combine several of the aspects of the present disclosure such that one could perform both allele calling as well as aneuploidy calling using one algorithm.

In an embodiment of the present disclosure, the disclosed method is employed to determine the genetic state of one or more embryos for the purpose of embryo selection in the context of IVF. This may include the harvesting of eggs from the prospective mother and fertilizing those eggs with sperm from the prospective father to create one or more embryos. It may involve performing embryo biopsy to isolate a blastomere from each of the embryos. It may involve amplifying and genotyping the genetic data from each of the blastomeres. It may include obtaining, amplifying and genotyping a sample of diploid genetic material from each of the parents, as well as one or more individual sperm from the father. It may involve incorporating the measured diploid and haploid data of both the mother and the father, along with the measured genetic data of the embryo of interest into a dataset. It may involve using one or more of the statistical methods disclosed in this patent to determine the most likely state of the genetic material in the embryo given the measured or determined genetic data. It may involve the determination of the ploidy state of the embryo of interest. It may involve the determination of the presence of a plurality of known disease-linked alleles in the genome of the embryo. It may involve making phenotypic predictions about the embryo. It may involve generating a report that is sent to the physician of the couple so that they may make an informed decision about which embryo(s) to transfer to the prospective mother.

Another example could be a situation where a 44-year old woman undergoing IVF is having trouble conceiving. The couple arranges to have her eggs harvested and fertilized with sperm from the man, producing nine viable embryos. A blastomere is harvested from each embryo, and the genetic data from the blastomeres are measured using an ILLUMINA INFINIUM BEAD array. Meanwhile, the diploid data are measured from tissue taken from both parents also using the ILLUMINA INFINIUM BEAD array. Haploid data from the father's sperm is measured using the same method. The method disclosed herein is applied to the genetic data of the nine blastomeres, of the diploid maternal and paternal genetic data, and of three sperm from the father. The methods described herein are used to clean and phase all of the genetic data used as input, plus to make ploidy calls for all of the chromosomes on all of the embryos, with high confidences. Six of the nine embryos are found to be aneuploid, and three embryos are found to be euploid. A report is generated that discloses these diagnoses, and is sent to the doctor. The doctor, along with the prospective parents, decides to transfer two of the three euploid embryos, one of which implants in the mother's uterus.

Another example may involve a pregnant woman who has been artificially inseminated by a sperm donor, and is pregnant. She is wants to minimize the risk that the fetus she is carrying has a genetic disease. She has blood drawn at a phlebotomist, and techniques described in this disclosure are used to isolate three nucleated fetal red blood cells, and a tissue sample is also collected from the mother and father. The genetic material from the fetus and from the mother and father are amplified as appropriate, and genotyped using the ILLUMINA INFINIUM BEAD array, and the methods described herein clean and phase the parental and fetal genotype with high accuracy, as well as to make ploidy calls for the fetus. The fetus is found to be euploid, and phenotypic susceptibilities are predicted from the reconstructed fetal genotype, and a report is generated and sent to the mother's physician so that they can decide what actions may be best.

Another example could be a situation where a racehorse breeder wants to increase the likelihood that the foals sired by his champion racehorse become champions themselves. He arranges for the desired mare to be impregnated by IVF, and uses genetic data from the stallion and the mare to clean the genetic data measured from the viable embryos. The cleaned embryonic genetic data allows the breeder to select the embryos for implantation that are most likely to produce a desirable racehorse.

A method for determining a ploidy state of at least one chromosome in a target individual includes obtaining genetic data from the target individual and from one or more related individuals; creating a set of at least one ploidy state hypothesis for each of the chromosomes of the target individual; determining a statistical probability for each ploidy state hypothesis in the set given the obtained genetic data and using one or more expert techniques; combining, for each ploidy state hypothesis, the statistical probabilities as determined by the one or more expert techniques; and determining the ploidy state for each of the chromosomes in the target individual based on the combined statistical probabilities of each of the ploidy state hypotheses.

A method for determining allelic data of one or more target individuals, and one or both of the target individuals' parents, at a set of alleles, includes obtaining genetic data from the one or more target individuals and from one or both of the parents; creating a set of at least one allelic hypothesis for each of the alleles of the target individuals and for each of the alleles of the parents; determining a statistical probability for each allelic hypothesis in the set given the obtained genetic data; and determining the allelic state for each of the alleles in the one or more target individuals and the one or both parents based on the statistical probabilities of each of the allelic hypothesis.

A method for determining a ploidy state of at least one chromosome in a target individual includes obtaining genetic data from the target individual, from both of the target individual's parents, and from one or more siblings of the target individual, wherein the genetic data includes data relating to at least one chromosome; determining a ploidy state of the at least one chromosome in the target individual and in the one or more siblings of the target individual by using one or more expert techniques, wherein none of the expert techniques requires phased genetic data as input; determining phased genetic data of the target individual, of the parents of the target individual, and of the one or more siblings of the target individual, using an informatics based method, and the obtained genetic data from the target individual, from the parents of the target individual, and from the one or more siblings of the target individual that were determined to be euploid at that chromosome; and redetermining the ploidy state of the at least one chromosome of the target individual, using one or more expert techniques, at least one of which requires phased genetic data as input, and the determined phased genetic data of the target individual, of the parents of the target individual, and of the one or more siblings of the target individual.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for determining a ploidy state of at least one chromosome or chromosome segment in the genome of an embryo, the method comprising:
   obtaining a biological sample
   measuring, from the biological sample, genetic data for the at least one chromosome or chromosome segment from the embryo and from one or more parents of the embryo, wherein the genetic data is the measured responses at various single nucleotide polymorphism (SNP) loci on the at least one chromosome;
   creating, on a computer, a set of at least one ploidy state hypothesis for the at least one chromosome or chromosome segment of the embryo;
   using two or more expert techniques to determine, on a computer, for each expert technique used, a statistical probability for each ploidy state hypothesis in the set given the measured genetic data, wherein the expert techniques are selected from:
   the Presence of Homologs technique, which technique uses genetic data obtained from both parents where one parent is heterozygous at a SNP and the other parent is homozygous at that SNP, wherein the Presence of Homologs technique comprises;
      (1) phasing the obtained genetic data from the parents and calculating noise floors per chromosome;
      (2) segmenting the at least one chromosome;
      (3) calculating SNP dropout rates per segment for parental genotypes of interest;
      (4) calculating SNP dropout rates for each parent on the at least one chromosome and hypothesis likelihoods on each segment;
      (5) combining the likelihoods across chromosome segments to produce a probability of data given parent strand hypothesis for whole chromosomes; and
      (6) checking for invalid calls and calculating a probability for each ploidy state hypothesis;
   the Permutation technique, which technique compares the relationship between distributions of the obtained genetic data of the embryo for different parental genotypes using a statistical algorithm to determine the probability of each ploidy state hypothesis given the obtained genetic data; and
   the Presence of Parents technique, which technique detects, independently for each parent, for a given chromosome, whether or not there is a contribution from that parent's genome based on distances between sets of parental genotypes at the widest point on cumulative distribution function curves which plot observed distributions of obtained genetic data for different parental genotypes, and assigns probabilities to each ploidy state hypothesis by calculating a summary statistic for each parent and comparing to data models for cases where a parent chromosome is present and cases where a parent chromosome is not present;
   combining, for each ploidy state hypothesis, the statistical probabilities as determined by the two or more expert techniques to determine combined statistical probabilities;
   and
   outputting the ploidy state with the greatest combined statistical probability as an indication of the ploidy state for the at least one chromosome or chromosome segment in the genome of the embryo.

2. The method of claim 1, further comprising measuring genetic data for the at least one chromosome or chromosome segment from one or more related individuals; wherein the related individuals are selected from the group consisting of one or both parents of the embryo, one or more grandparents of the embryo, one or more siblings of the embryo, and combinations thereof.

3. The method of claim 1, wherein the measured genetic data comprises single nucleotide polymorphism (SNP) data measured using a technology selected from the group consisting of genotyping arrays, DNA sequencing, and combinations thereof.

4. The method of claim 3, wherein the measured genetic data comprises data for at least 500 SNPs.

5. The method of claim 1, wherein at least one of the selected expert techniques is the Presence of Parents technique.

6. The method of claim 1, further comprising measuring genetic data for the at least one chromosome or chromosome segment from both parents of the embryo; wherein the measured genetic data is not phased, and wherein the method further comprises:
  determining phased genetic data for both parents of the fetus using an informatics based method; and
  determining phased genetic data for the embryo using an informatics based method.

7. The method of claim 1, comprising measuring phased genetic data for one or both parents of the embryo.

8. The method of claim 1, wherein the method further comprises performing amniocentesis or chorion villus biopsy.

9. The method of claim 1, wherein the at least one chromosome or chromosome segment is selected from the group consisting of chromosome 13, chromosome 18, chromosome 21, the X chromosome, the Y chromosome, and combinations thereof.

10. The method of claim 1, wherein determining the ploidy state of the at least one chromosome or chromosome segment in the embryo involves screening for a chromosomal condition selected from the group consisting of euploidy, nullsomy, monosomy, uniparental disomy, trisomy, matched copy error, unmatched copy error, tetrasomy, other aneuploidy, unbalanced translocation, deletions, insertions, mosaicism, and combinations thereof.

11. The method of claim 1, wherein the method comprises determining whether the embryo has Down syndrome, Klinefelter syndrome, Trisomy 18, or Turner syndrome.

12. The method of claim 1, wherein at least one of the selected expert techniques determines the probability that zero, one, or two copies of the parental homolog is present in the chromosome or chromosome segment.

13. The method of claim 1, wherein at least one of the selected expert techniques utilizes phased genetic information of the first parent at one or more single nucleotide polymorphic loci for which the first parent is heterozygous and the second parent is homozygous.

14. The method of claim 1, wherein at least one of the selected expert techniques differentiates between mitotic trisomy and meiotic trisomy.

15. The method of claim 10, wherein at least one of the selected expert techniques differentiates between an unmatched copy error and a matched copy error for the chromosome or chromosome segment.

16. The method of claim 1, wherein at least one of the selected expert techniques is the Presence of Homologs technique.

17. The method of claim 1, wherein at least one of the selected expert techniques is the Permutation technique.

* * * * *